(12) United States Patent
Duran et al.

(10) Patent No.: US 7,557,212 B2
(45) Date of Patent: Jul. 7, 2009

(54) TRICYCLIC DERIVATIVES AS LTD4 ANTAGONISTS

(75) Inventors: Carlos Puig Duran, Barcelona (ES); Daniel Perez Crespo, Barcelona (ES); Jordi Bach Tana, Barcelona (ES); Hamish Ryder, Barcelona (ES)

(73) Assignee: Laboratorios Almirall, S.A., Barcelona (ES)

( * ) Notice: Subject to any disclaimer, the term of this patent is extended or adjusted under 35 U.S.C. 154(b) by 5 days.

(21) Appl. No.: 10/534,487

(22) PCT Filed: Nov. 11, 2003

(86) PCT No.: PCT/EP03/12581
§ 371 (c)(1), (2), (4) Date: Jan. 9, 2006

(87) PCT Pub. No.: WO2004/043966
PCT Pub. Date: May 27, 2004

(65) Prior Publication Data
US 2006/0116363 A1    Jun. 1, 2006

(30) Foreign Application Priority Data
Nov. 12, 2002    (ES) ................. 200202590

(51) Int. Cl.
*C07D 453/04* (2006.01)
*C07D 471/00* (2006.01)
*C07D 491/00* (2006.01)

(52) U.S. Cl. .................. 546/134; 546/135; 546/80; 546/81; 546/83

(58) Field of Classification Search ............ 546/99, 546/134, 135, 80, 81, 83; 514/291, 267
See application file for complete search history.

(56) References Cited

FOREIGN PATENT DOCUMENTS

| | | | |
|---|---|---|---|
| EP | 0 685 478 | A | 2/1995 |
| EP | 1 254 897 | A1 | 11/2002 |
| WO | WO 89/10369 | A1 | 11/1989 |
| WO | 0147889 | * | 7/2001 |
| WO | WO/2004/058742 | * | 5/2004 |

OTHER PUBLICATIONS

Villani et al. Journal of Medicinal Chemistry, 1972, 15(7), 750.*
Zwaagstra et al. "Synthesis of 3- and 5'-substituted flavone-8-carboxylic acids as 'three-armed' leukotriene *CysLT1* receptor antagonists," Eur. J. Med. Chem., 33, 1998, p. 95-102.
Zhang et al. "The Role of Arginine in the Binding of $LTD_4$ Antagonists to $cysLT_1$ receptors of Guinea Pig Lung," Bioorganic & Medicinal Chemistry Letters, 7(10), 1997, p. 1331-1336.
Zhang and Zwaagstra, "Structural Requirements for Leukotriene $CysLT_1$ Receptor Ligans," Current Medicinal Chemistry, 4, 1997, p. 229-246.
Villani et al., "Derivatives of 10,11-Dihydro-5*H*-dibenzo[a,b]cycloheptene and Related Compounds V: Homologous 4-Azaketones and Derivatives," *J. Pharm. Sci.*, 60(10): 1586 (1971) (paper 5).
Villani et al., "Dialkylaminoalkyl Derivatives of 10,11-Dihydro-5H-dibenzo[a,d]cycloheptene and Related Compounds," *J. Med. Chem.*, 5, 373 (1962).
Villani et al., "Derivatives of 10,11-Dihydro-5H-dibenzo[a,d]-cycloheptene and Related Compounds. II," *J. Med. Chem.*, 7, 457 (1964).

* cited by examiner

*Primary Examiner*—D. Margaret Seaman
*Assistant Examiner*—Nizal S Chandrakumar
(74) *Attorney, Agent, or Firm*—Finnegan, Henderson, Farabow, Garrett & Dunner, LLP

(57) ABSTRACT

Compounds of formula (I) and their pharmaceutically acceptable salts are provided as well as processes for the manufacture of such compounds. The compounds are useful in the treatment or prevention of inflammatory and allergic diseases.

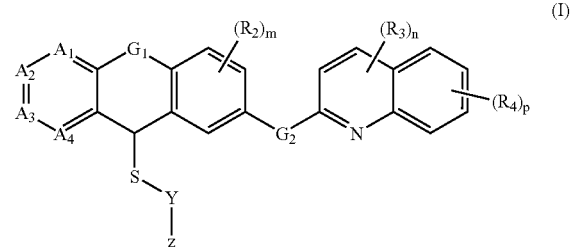

14 Claims, No Drawings

TRICYCLIC DERIVATIVES AS LTD4 ANTAGONISTS

This application is a national phase of international application number PCT/EP2003/012581, filed Nov. 11, 2003, and claims the priority of Spanish application number 200202590, filed Nov. 12, 2002.

The present invention relates to new therapeutically useful tricyclic derivatives, to processes for their preparation and to pharmaceutical compositions containing them. These compounds are potent leukotriene D4 antagonists and are thus useful in the treatment, prevention or suppression of pathological conditions, diseases and disorders known to be susceptible of being improved by inhibition of the biological effects of leukotriene D4.

Leukotrienes are compounds produced in mammals by the metabolism of arachidonic acid trough the lipoxygenase pathway. The different leukotrienes are designated by letter-number combinations, such as the non-peptide leukotriene B4 (LTB4), and the peptide-leukotrienes C4 (LTC4), D4 (LTD4) and E4 (LTE4).

Leukotrienes participate in inflammatory reactions, exhibit chemotactic activities, stimulate lysosomal enzyme release and play an important role in the intermediate hypersensitivity reaction. Their biology is described in several reviews, for example Dahlen et al., Nature, 288, 484 (1980)) describe that LTD4 is a potent bronchoconstrictor of the human bronchi and Burke et al., J. Pharmacol. And Exp. Therap., 221, 235 (1982) describe that it is a potent coronary vasoconstrictor and influences contractile force in the myocardium and coronary flow rate of the isolated heart.

In view of their physiological effects, LTD4 antagonists of varied chemical structures have been recently disclosed for the treatment or prevention of pathological conditions, diseases and disorders known to be susceptible to amelioration by inhibition of LTD4 such as bronchial asthma, allergic and perennial rhinitis, chronic obstructive pulmonary disease, urticaria, atopic dermatitis, migraine, viral broncholitis caused by RSV, cystic fibrosis, eosinophilic gastro-enteritis, fibromyalgia A and interstitial cystitis. See, for example EP 0 173 516, EP 0 463 638, EP 0 490 648, U.S. Pat. No. 5,856,322, HEADACHE, (2000 February) 40 (2) 158-63, Dermatology, (2001) 203 (4) 280-3. Ref: 51, International Journal of Clinical Pharmacology and Therapeutics, (2001 December) 39 (12) 529-33, Journal of the American Academy of Dermatology, (2001 January) 44 (1) 89-93, Annals of Pharmacotherapy, (1997 September) 31 (9) 1012-21. Ref: 43, Pulmonary Pharmacology and Therapeutics, (2000) 13 (6) 301-5, American Journal of physiology. Lung Cellular and Molecular Physiology (2002 May) 282 (5) Li 143-50, Respirology, (2000 December) 5 (4) 389-92, Thorax, (2001 March) 56 (3) 244-5, Urology, (2001 June) 57 (6 Suppl 1) 118, Journal of Urology, (2001 November) 166 (5) 1734-7, BJU International, (2001 May) 87 (7) 690-6, Current Gastroenterology Reports, (2002 October) 4 (5) 366-72, Digestive Diseases and Sciences, (2001 August) 46 (8) 1787-90, Journal of Allergy and Clinical Immunology, (1999 August) 104 (2 Pt 1) 506, Acta Odontologica Scandinavica, (2002 January) 60 (1) 29-36, Journal of Orofacial Pain, (2001 Winter) 15 (1) 9-28. Ref: 168, Acta Odontologica Scandinavica, (2001 December) 59 (6) 348-55.

A few compounds having a leukotriene D4 antagonistic action have reached the market place. For example 1-[[[(1R-1-[3-[(1E)-2-(7-chloro-2-quinolinyl) ethenyl]phenyl]-3-[2-(1-hydroxy-1-methylethyl) phenyl]propyl]thio]methyl]cyclopropaneacetic acid (Montelukast ex. Merck; Bioorg. Med. Chem. Lett. 1995, 5, 283), [3-[[2-methoxy-4-[[[(2-methylphenyl) sulfonyl]amino]carbonyl]phenyl]methyl]-1-methyl-1H-indol-5-yl]carbamic acid cyclopentyl ester (Zafirlukast ex. AstraZeneca; J. Med. Chem. 1990, 33, 1781) or N-[4-oxo-2-(1H-tetrazol-5-yl)$_4$H-1-benzopyran-8-yl]4-(4-phenylbutoxy)benzamide (Pranlukast ex. Ono; J. Med. Chem. 1988, 31, 84).

We have now found that a novel series of tricyclic derivatives are potent leukotriene D4 antagonists and are therefore useful in the treatment or prevention of pathological conditions, diseases and disorders known to be susceptible of amelioration by inhibition of LTD4, such as bronchial asthma, allergic and perennial rhinitis, chronic obstructive pulmonary disease, urticaria, atopic dermatitis, migraine, viral broncholitis caused by RSV, cystic fibrosis, eosinophilic gastro-enteritis, fibromyalgia A and interstitial cystitis.

The compounds of the present invention can also be used in combination with other drugs known to be effective in the treatment of these diseases. For example, in combination with triptans or COX-2 inhibitors in the treatment of migraine; with H1 antagonists in the treatment of allergic disorders, such as rhinitis or urticaria; or with PDE IV inhibitors in the treatment of allergic disorders, asthma or chronic obstructive pulmonary disease.

Accordingly, the present invention provides novel compounds of formula (I)

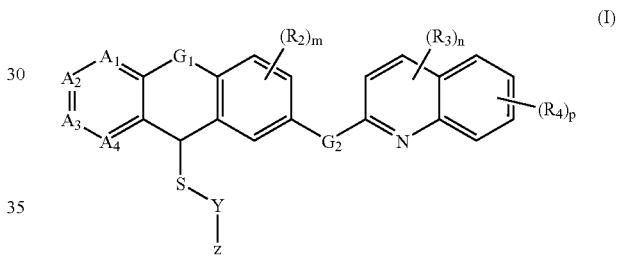

or pharmaceutically acceptable salts thereof wherein:

from one to three of $A_1$, $A_2$, $A_3$ and $A_4$ are nitrogen atoms, the others being —$CR_1$— groups;

$G_1$ represents a group selected from —$CH_2$—O—, —$CH_2$—$CH_2$—, —CH=CH—, —$CH_2$—S—, —N($C_1$-$C_4$ alkyl)-CH2;

$G_2$ represents a group selected from —O—$CH_2$—, —CH=CH—, —$CH_2$—$CH_2$—, each of $R_1$, $R_2$, $R_3$ and $R_4$ is the same or different and is selected from hydrogen or halogen atoms and hydroxy, alkyl, alkenyl, alkynyl, alkoxy, alkylthio, amino, monoalkyamino, dialkylamino, nitro, cyano, acyloxy, alkoxycarbonyl, hydroxycarbonyl and acylamino groups, the hydrocarbon chains of these groups being optionally substituted by one or more further substituents selected from halogen, hydroxy, oxo, alkoxy, alkylthio, acylamino, phenyl, alkoxycarbonyl, amino, monoalkylamino, dialkylamino and hydroxycarbonyl groups, n, m and p are independently 0, 1 or 2

Y represents an optionally substituted radical selected from alkyl, cycloalkyl, aryl, alkyl-cycloalkyl, cycloalkyl-alkyl, arylalkyl, alkylaryl, alkyl-cycloalkyl-alkyl, cycloalkyl-alkyl-cycloalkyl, alkyl-aryl-alkyl and aryl-alkyl-aryl Z represents a tetrazolyl group, a —$COOR_5$ group, a —$CONR_5R_5$ group, a $NHSO_2R_5$ group or —$CONHSO_2R_5$ group wherein $R_5$ represents a hydrogen or an optionally substituted group selected from alkyl, aryl, cycloalkyl, heterocyclyl and heteroaryl.

For the avoidance of doubt, the orientation of the group $G_2$ is such that the right hand side of the depicted moieties are attached to the quinoline moiety. Thus, for example, when $G_2$ is —O—$CH_2$—, the C atom is attached to the quinoline moiety. Similarly, the orientation of the group $G_1$ is such that the right hand side of the depicted moieties are attached to the benzene ring. Thus, for example, when $G_1$ is —$CH_2$—O—, the O atom is attached to the benzene ring.

Also, when the Y groups contain more than one moiety, the orientation of the Y groups is such that the first named moiety is attached to the S atom and the last named moiety is attached to the Z group. Thus, for example, when Y is alkyl-cycloalkyl, —SYZ is —S-alkyl-cycloalkyl-Z.

Certain LTD4 antagonists having a tricyclic core structure such as certain dibenz[b,e]oxepines have been disclosed in European patent application number 0685478A1 or PCT Application number WO 01/47889A1.

Other aspects of the present invention are: a) a process for the preparation of the compounds of formula (I), b) pharmaceutical compositions comprising an effective amount of said compounds, c) the use of said compounds in the manufacture of a medicament for the treatment of diseases susceptible of being improved by antagonism of LTD4 receptors; and d) methods of treatment of diseases susceptible to amelioration by antagonism of LTD4 receptors, which methods comprise the administration of the compounds of the invention to a subject in need of treatment.

As used herein, some of the atoms, groups, moieties, chains or cycles present in the general structures of the invention are "optionally substituted". This means that these atoms, groups, moieties, chains or cycles can be either unsubstituted or substituted in any position by one or more, for example 1, 2, 3 or 4, substituents, whereby the hydrogen atoms bound to the unsubstituted atoms, groups, moieties, chains or cycles are replaced by chemically acceptable atoms, groups, moieties, chains or cycles. When two or more substituents are present, each substituent may be the same or different.

Examples of substituent(s) are typically but not limited to halogen atoms, preferably fluoride atoms, and hydroxy or alkoxy groups. The substituents are typically themselves unsubstituted.

As used herein, an alkyl group can be an optionally substituted straight or branched alkyl, and is typically a lower alkyl group. A lower alkyl group contains 1 to 8, preferably 1 to 6 and more preferably 1 to 4 carbon atoms.

Examples include methyl, ethyl, n-propyl, i-propyl, n-butyl, sec-butyl, tert-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl groups.

In particular it is preferred that such an alkyl group is selected from the group consisting of methyl, ethyl, n-propyl, i-propyl, n-butyl, sec-butyl, tert-butyl, n-pentyl, 1-methylbutyl, 1-ethylpropyl, 1,2-dimethylpropyl, n-hexyl and 1-ethylbutyl group.

An alkyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Preferred alkyl groups are unsubstituted or substituted with 1, 2 or 3 fluorine atoms.

As used herein, an alkenyl group can be straight or branched, mono or polyunsaturated, and is typically a lower alkenyl group. A lower alkenyl group contains 2 to 8, preferably 2 to 6, more preferably 2 to 4 carbon atoms. In particular it is preferred that the alkenyl group is mono or diunsaturated.

In particular it is preferred that such an alkenyl group is selected from the group consisting of 2-vinyl, prop-1 enyl, allyl, but-1-enyl, but-2-enyl, but-3-enyl, 2-methylprop-2-enyl, 2-methylprop-1-enyl, 1-ethylvinyl, 1-methylprop-1-enyl, 1-methylprop-2-enyl and buta-1,3-dienyl.

As used herein, an alkynyl group can comprise one or more polyunsaturation, be straight or branched, and is typically a lower alkynyl group. A lower alkinyl group contains 2 to 8, preferably 2 to 6, more preferably 2 to 4 carbon atoms.

In particular it is preferred that such an alkinyl group is selected from the group consisting of 1-propynyl, 2-propynyl, 1-butynyl, 2-butynyl, 3-butynyl and 1-methyl-2-propinyl.

As used herein, the term alkoxy (or alkyloxy) embraces optionally substituted, straight or branched oxy-containing radicals each having alkyl portions of 1 to 10 carbon atoms. More preferred alkoxy radicals are "lower alkoxy" radicals having 1 to 8, preferably 1 to 6 and more preferably 1 to 4 carbon atoms.

An alkoxy group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

Preferred optionally substituted alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein, the term alkylthio embraces radicals containing an optionally substituted, straight or branched alkyl radical of 1 to 10 carbon atoms attached to a divalent sulphur atom. More preferred alkylthio radicals are "lower alkylthio" radicals having 1 to 8, preferably 1 to 6 and more preferably 1 to 4 carbon atoms.

An alkylthio group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

Preferred optionally substituted alkylthio radicals include methylthio, ethylthio, n-propylthio, i-propylthio, n-butylthio, sec-butylthio, t-butylthio, trifluoromethylthio, difluoromethylthio, hydroxymethylthio, 2-hydroxyethylthio or 2-hydroxypropylthio.

As used herein, the term monoalkylamino embraces radicals containing an optionally substituted, straight or branched alkyl radicals of 1 to 10 carbon atoms attached to a divalent —NH— radical. More preferred monoalkylamino radicals are "lower monoalkylamino" radicals having 1 to 8, preferably 1 to 6 and more preferably 1 to 4 carbon atoms.

A monoalkylamino group typically contains an alkyl group which is unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

Preferred optionally substituted monoalkylamino radicals include methylamino, ethylamino, n-propylamino, i-propylamino, n-butylamino, sec-butylamino, t-butylamino, trifluoromethylamino, difluoromethylamino, hydroxymethylamino, 2-hydroxyethylamino or 2-hydroxypropylamino.

As used herein, the term dialkylamino embraces radicals containing a trivalent nitrogen atom with two optionally substituted, straight or branched alkyl radicals of 1 to 10 carbon atoms attached thereto. More preferred dialkylamino radicals are "lower dialkylamino" radicals having 1 to 8, preferably 1 to 6 and more preferably 1 to 4 carbon atoms in each alkyl radical.

A dialkylamino group typically contains two alkyl groups, each of which is unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

Preferred optionally substituted dialkylamino radicals include dimethylamino, diethylamino, methyl(ethyl)amino, di(n-propyl)amino, n-propyl(methyl)amino, n-propyl(ethyl)amino, di(i-propyl)amino, i-propyl(methyl)amino, i-propyl(ethyl)amino, di(n-butyl)amino, n-butyl(methyl)amino, n-butyl(ethyl)amino, n-butyl(i-propyl)amino, di(sec-butyl)amino, sec-butyl(methyl)amino, sec-butyl(ethyl)amino, sec-butyl(n-propyl)amino, sec-butyl(i-propyl)amino, di(t-butyl)amino, t-butyl(methyl)amino, t-butyl(ethyl)amino, t-butyl(n-propyl)amino, t-butyl(i-propyl)amino, trifluoromethyl(methyl)amino, trifluoromethyl(ethyl)amino, trifluoromethyl(n-propyl)amino, trifluoromethyl(i-propyl)amino, trifluoromethyl(n-butyl)amino, trifluoromethyl(sec-butyl)amino, difluoromethyl(methyl)amino, difluoromethyl(ethyl)amino, difluoromethyl(n-propyl)amino, difluoromethyl(i-propyl)amino, difluoromethyl(n-butyl))amino, difluoromethyl(sec-butyl)amino, difluoromethyl(t-butyl)amino, difluoromethyl(trifluoromethyl)amino, hydroxymethyl(methyl)amino, ethyl(hydroxymethyl)amino, hydroxymethyl(n-propyl)amino, hydroxymethyl(i-propyl)amino, n-butyl(hydroxymethyl)amino, sec-butyl(hydroxymethyl)amino, t-butyl(hydroxymethyl)amino, difluoromethyl(hydroxymethyl)amino, hydroxymethyl(trifluoromethyl)amino, hydroxyethyl(methyl)amino, ethyl(hydroxyethyl)amino, hydroxyethyl(n-propyl)amino, hydroxyethyl(i-propyl)amino, n-butyl(hydroxyethyl)amino, sec-butyl(hydroxyethyl)amino, t-butyl(hydroxyethyl)amino, difluoromethyl(hydroxyethyl)amino, hydroxyethyl(trifluoromethyl)amino, hydroxypropyl(methyl)amino, ethyl(hydroxypropyl)amino, hydroxypropyl(n-propyl)amino, hydroxypropyl(i-propyl)amino, n-butyl(hydroxypropyl)amino, sec-butyl(hydroxypropyl)amino, t-butyl(hydroxypropyl)amino, difluoromethyl(hydroxypropyl)amino, hydroxypropyl(trifluoromethyl)amino.

As used herein, the term alkoxycarbonyl embraces optionally substituted, straight or branched radicals each having alkyl portions of 1 to 10 carbon atoms and attached to an oxycarbonyl radical. More preferred alkoxycarbonyl radicals are "lower alkoxycarbonyl" radicals having 1 to 8, preferably 1 to 6 and more preferably 1 to 4 carbon atoms.

An alkoxycarbonyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

Preferred optionally substituted alkoxycarbonyl radicals include methoxycarbonyl, ethoxycarbonyl, n-propoxycarbonyl, i-propoxycarbonyl, n-butoxycarbonyl, sec-butoxycarbonyl, t-butoxycarbonyl, trifluoromethoxycarbonyl, difluoromethoxycarbonyl, hydroxymethoxycarbonyl, 2-hydroxyethoxycarbonyl or 2-hydroxypropoxycarbonyl.

As used herein, the term acyl embraces optionally substituted, straight or branched radicals having 2 to 20 carbon atoms or, preferably 2 to 12 carbon atoms attached to a carbonyl radical. More preferably acyl radicals are "lower acyl" radicals having 2 to 8, preferably 2 to 6 and more preferably 2 to 4 carbon atoms. Thus, it is typically a radical of formula —COR.

An acyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms.

Preferred optionally substituted acyl radicals include acetyl, propionyl, butiryl, isobutiryl, isovaleryl, pivaloyl, valeryl, lauryl, myristyl, stearyl and palmityl, As used herein, the term cycloalkyl embraces saturated carbocyclic radicals and, unless otherwise specified, a cycloalkyl radical typically has from 3 to 7 carbon atoms. Examples include cyclopropyl, cyclobutyl, cyclopentyl, cyclohexyl and cycloheptyl. It is preferably cyclopropyl, cyclopentyl or cyclohexyl.

A cycloalkyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Preferred carbocyclyl groups are unsubstituted.

As used herein, an aryl group or moiety is typically a $C_5$-$C_{14}$ aryl group or moiety, which can be monocyclic or polycyclic, such as phenyl, naphthyl, anthranyl or phenanthryl. An aryl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Preferred aryl groups are unsubstituted.

As used herein, a heteroaryl group or moiety is typically a 5- to 10-membered ring system comprising at least one heteroaromatic ring and containing at least one heteroatom selected from O, S and N. A heteroaryl group may be a single ring or two or more fused rings wherein at least one ring contains a heteroatom.

Examples include pyridyl, pyrazinyl, pyrimidinyl, pyridazinyl, furyl, oxadiazolyl, oxazolyl, imidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, indolyl, indazolyl, purinyl, imidazolidinyl, pteridinyl and pyrazolyl groups.

Oxadiazolyl, oxazolyl, pyridyl, pyrrolyl, imidazolyl, thiazolyl, thiadiazolyl, furyl, thienyl, pyrazinyl and pyrimidinyl groups are preferred.

A heteroaryl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Preferred heteroaryl groups are unsubstituted.

As used herein, a heterocyclyl group is typically a non-aromatic, saturated or unsaturated $C_3$-$C_{10}$ cycloalkyl ring, such as a 5, 6 or 7 membered ring, in which one or more, for example 1, 2, 3 or 4, of the carbon atoms, preferably 1 or 2 of the carbon atoms are replaced by a heteroatom selected from N, O and S. Saturated heterocyclyl groups are preferred. A heterocyclic group may be a single ring or two or more fused rings wherein at least one ring contains a heteroatom.

Examples of heterocyclic radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, cromanyl, isocromanyl, imidazolidinyl, imidazolyl, oxiranyl, azaridinyl, 4,5-dihydro-oxazolyl and 3-aza-tetrahydrofuranyl.

Examples of heterocyclic groups include piperidyl, pyrrolidyl, pyrrolinyl, piperazinyl, morpholinyl, thiomorpholinyl, pyrrolyl, pyrazolyl, pirazolidinyl, quinuclidinyl, triazolyl, pyrazolyl, tetrazolyl, cromanyl, isocromanyl, imidazolidinyl, imidazolyl, oxiranyl, azaridinyl, 4,5-dihydro-oxazolyl and 3-aza-tetrahydrofuranyl.

Most preferred are examples include piperidinyl, piperazinyl, morpholinyl, 4,5-dihydro-oxazolyl, 3-aza-tetrahydrofuranyl, imidazolidinyl and pyrrolidinyl groups.

A heterocyclyl group is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Preferred heterocyclyl groups are unsubstituted.

As used herein, a halogen atom, is typically a chlorine, fluorine or bromine atom.

Compounds of formula (I) containing one or more chiral centre may be used in enantiomerically or diastereoisomerically pure form, or in the form of a mixture of isomers.

As used herein, a pharmaceutically acceptable salt is a salt with a pharmaceutically acceptable acid or base. Pharmaceutically acceptable acids include both inorganic acids, for example hydrochloric, sulphuric, phosphoric, diphosphoric, hydrobromic, hydroiodic or nitric acid and organic acids, for example citric, fumaric, maleic, malic, mandelic, ascorbic, oxalic, succinic, tartaric, benzoic, acetic, methanesulfonic, ethanesulfonic, benzenesulfonic or p-toluenesulfonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Each of $R_1$, $R_2$, $R_3$ and $R_4$ is typically unsubstituted or substituted with 1, 2 or 3 substituents which may be the same or different. Typically, when two or more substituents are present on an $R_1$, $R_2$, $R_3$ or $R_4$ group, no more than one of these substituents is a phenyl group. Preferred substituents for $R_1$, $R_2$, $R_3$ and $R_4$ are halogen atoms, in particular fluorine, hydroxy groups and alkoxy groups having from 1 to 4 carbon atoms. More preferably, $R_1$, $R_2$, $R_3$ and $R_4$ are unsubstituted.

$R_1$ is typically a hydrogen or halogen atom or an alkyl group having from 1 to 4 carbon atoms. Preferably, $R_1$ is a hydrogen atom, a halogen atom, in particular a fluorine or chlorine atom, or a methyl group.

According to one particular embodiment of the present invention in the compounds of formula (I):

from one to three of $A_1$, $A_2$, $A_3$ and $A_4$ are nitrogen atoms, the others being —$CR_1$— groups;

$G_1$ represents a group selected from —$CH_2O$—, —$CH_2$—$CH_2$—, —$CH_2$—S—, —$N(C_1$-$C_4$ alkyl)-CH2;

$G_2$ represents a group selected from —O—$CH_2$—, —CH=CH—, —$CH_2$—$CH_2$—;

each of $R_1$, $R_2$, $R_3$ and $R_4$ is the same or different and is selected from hydrogen or halogen atoms and hydroxy, alkyl, alkenyl, alkynyl, alkoxy, alkylthio, amino, monoalkyamino, dialkylamino, nitro, cyano, acyloxy, alkoxycarbonyl, hydroxycarbonyl and acylamino groups, the hydrocarbon chains of these groups being optionally substituted by one or more further substituents selected from halogen, hydroxy, oxo, alkoxy, alkylthio, acylamino, phenyl, alkoxycarbonyl, amino, monoalkylamino, dialkylamino and hydroxycarbonyl groups, n, m and p are independently 0, 1 or 2

Y represents an optionally substituted radical selected from alkyl, cycloalkyl, aryl, alkyl-cycloalkyl, cycloalkyl-alkyl, arylalkyl, alkylaryl, alkyl-cycloalkyl-alkyl, cycloalkyl-alkyl-cycloalkyl, alkyl-aryl-alkyl and aryl-alkyl-aryl Z represents a tetrazolyl group, a —$COOR_5$ group, a —$CONR_5R_5$ group, a $NHSO_2R_5$ group or —$CONHSO_2R_5$ group wherein $R_5$ represents a hydrogen or an optionally substituted group selected from alkyl, aryl, cycloalkyl, heterocyclyl and heteroaryl.

According to one embodiment of the present invention in the compounds of formula (I) one of $A_1$, $A_2$, $A_3$ and $A_4$ is a nitrogen atom, the others being —$CR_1$— groups.

More preferably $A_1$ is a nitrogen atom and $A_2$, $A_3$ and $A_4$ are —$CR_1$— groups. Still more preferably $R_1$ is a hydrogen atom.

Also preferred are compounds of formula (I) wherein $A_4$ is a nitrogen atom and $A_1$, $A_2$ and $A_3$ are —$CR_1$— groups. Still more preferably $R_1$ is a hydrogen atom.

When two or more $R_1$ groups are present, each $R_1$ is the same or different.

According to another embodiment of the present invention in the compounds of formula (I) $G_1$ is a —$CH_2O$— group.

According to still another embodiment of the present invention in the compounds of formula (I) $G_2$ is selected from the group consisting of —$OCH_2$— and —CH=CH—.

Typically, m is 0 or 1 and is preferably 0. $R_2$ is preferably a halogen atom or an alkyl group having from 1 to 4 carbon atoms. More preferably $R_2$ is methyl, fluorine or chlorine. When two or more $R_2$ groups are present, each $R_2$ is the same or different.

Typically, n is 0 or 1 and is preferably 0. $R_3$ is preferably a halogen atom or an alkyl group having from 1 to 4 carbon atoms. More preferably $R_3$ is methyl, fluorine or chlorine. When two or more $R_3$ groups are present, each $R_3$ is the same or different.

According to another embodiment of the present invention in the compounds of formula (I) p is 0, 1 or 2, preferably 2. Typically, each $R_4$ is a halogen atom or an alkyl group having from 1 to 4 carbon atoms. More preferably each $R_4$ is a halogen atom, most preferably selected from F or Cl. When two or more R groups are present, each R is the same or different.

According to still another embodiment of the present invention in the compounds of formula (I), Y represents a group selected from alkyl, alkyl-cycloalkyl-alkyl or alkylaryl, said group being optionally substituted by one or more substituents selected from halogens, hydroxy, alkoxy, amino, alkyl or haloalkyl. Typically, said Y moieties are unsubstituted or are substituted with 1, 2 or 3 substituents which may be the same or different. The substituents are preferably selected from halogen atoms, hydroxy and amino groups and $C_1$-$C_4$ alkoxy, $C_1$-$C_4$ alkyl and $C_1$-$C_4$ haloalkyl groups. Preferably, Y is unsubstituted or substituted with one or more alkyl groups having from 1 to 4 carbon atoms, more preferably Y is an unsubstituted radical.

Typically, Y represents an unsubstituted alkyl group having from 1 to 4 carbon atoms, a benzyl group or a methylcyclopropylmethyl group. Most preferably, Y represents a group selected from —$CH_2CH_2$— and 2-cyclopropylpropyl.

$R_5$ is typically unsubstituted or substituted with 1, 2 or 3 substituents which may be the same or different. The substituents are preferably selected from halogen atoms, preferably fluorine atoms, hydroxy groups and alkoxy groups having from 1 to 4 carbon atoms. Most preferred substituents are fluorine atoms. $R_5$ is preferably unsubstituted or substituted with 1, 2 or 3 halogen atoms, in particular with 1, 2 or 3 fluorine atoms.

$R_5$ is preferably a hydrogen atom or an unsubstituted or substituted alkyl group having from 1 to 4 carbon atoms. Most preferred groups $R_5$ are hydrogen, methyl, ethyl and trifluoromethyl. When two or more $R_5$ groups are present, each $R_5$ may be the same or different.

Z is typically a tetrazolyl group, a —$COOR_5$ group, a —$CONR_5R_5$ group or a —$NHSO_2R_5$ group wherein $R_5$ is as defined above. Preferably, Z is a tetrazolyl group, a —COOH group, a —COOMe group, a —COOEt group, a —$CONH_2$ group or a —$NHSO_2CF_3$ group.

Particular individual compounds of the invention include:
3-{(7-[(6,7-difluoroquinolin-2-yl)methoxy]-5,11-dihydro[1]benzoxepino[3,4-b]pyrindin-5-yl)thio}propanoic acid
{(7-[(6,7-difluoroquinolin-2-yl)methoxy]-5,11-dihydro[1]benzoxepino[3,4-b]pyrindin-5-yl)thio}acetic acid
{(7-[(7-chloro,6-fluoroquinolin-2-yl)methoxy]-5,11-dihydro[1]benzoxepino[3,4-b]pyrindin-5-yl)thio}acetic acid
3-{(7-[(7-chloro,6-fluoro-quinolin-2-yl)methoxy]-5,11-dihydro[1]benzoxepino[3,4-b]pyrindin-5-yl)thio}propanoic acid
[{(7-[(6,7-difluoroquinolin-2-yl)methoxy]-5,11-dihydro[1]benzoxepino[3,4-b]pyrindin-5-yl)thio}methyl]benzoic acid
[{(7-[(7-chloro,6-fluoro-quinolin-2-yl)methoxy]-5,11-dihydro[1]benzoxepino[3,4-b]pyrindin-5-yl)thio}methyl]benzoic acid
1-{[(7-[(6,7-difluoroquinolin-2-yl)methoxy]-5,11-dihydro[1]benzoxepino[3,4-b]pyrindin-5-yl)thio]methyl}cyclopropyl acetic acid
3-{(7-[(6,7-difluoroquinolin-2-yl)methoxy]-5,11-dihydro[1]benzoxepino[3,4-b]pyrindin-5-yl)thio}-2,2-dimethyl-propanoic acid
3-{(7-[(6,7-difluoroquinolin-2-yl)methoxy]-5,1-dihydro[1]benzoxepino[3,4-b]pyrindin-5-yl)thio}-3methylbutanoic acid
3-{(7-[(E)-2-(6,7-difluoroquinolin-2-yl)vinyl]-5,11-dihydro[1]benzoxepino[3,4-b]pyrindin-5-yl)thio}propanoic acid
1-{[(7-[(E)-2-(6,7-difluoroquinolin-2-yl)vinyl]-5,11-dihydro[1]benzoxepino[3,4-b]pyrindin-5-yl)thio]methyl}cyclopropyl acetic acid
{(7-[(E)-2-(6,7-difluoroquinolin-2-yl)vinyl]-5,11-dihydro[1]benzoxepino[3,4-b]pyrindin-5-yl)thio}acetic acid
7-[(E)-2-(6,7-difluoroquinolin-2-yl)vinyl]-5-{[2-(1H-tetrazol-5-yl)ethyl]thio}-5,11-dihydro[1]benzoxepino[3,4-b]pyridine
1,1,1-trifluoro-N-[2-({7-[(E)-2-(6,7-difluoroquinolin-2-yl)vinyl]-5,11-dihydro[1]benzoxepino[3,4-b]pyrindin-5-yl)thio}ethyl]methanesulfonamide
1,1,1-trifluoro-N-[2-({7-[(6,7-difluoroquinolin-2-yl)methoxy]-5,11-dihydro[1]benzoxepino[3,4-b]pyrindin-5-yl)thio}ethyl]methanesulfonamide
3-{(9-[(E)-2-(6,7-difluoroquinolin-2-yl)vinyl]-5,11-dihydro[1]benzoxepino[4,3-b]pyrindin-11-yl)thio}propanoic acid
3-{(9-[(6,7-difluoroquinolin-2-yl)methoxy]-5,11-dihydro[1]benzoxepino[4,3-b]pyrindin-11-yl)thio}propanoic acid
1-{[(9-[(6,7-difluoroquinolin-2-yl)methoxy]-5,11-dihydro[1]benzoxepino[4,3-b]pyrindin-11-yl)thio]methyl}cyclopropyl acetic acid
7-[(6,7-difluoroquinolin-2-yl)methoxy]-5-{[2-(1H-tetrazol-5-yl)methyl]thio}5,11-dihydro[1]benzoxepino[3,4-b]pyridine
7-[(6,7-difluoroquinolin-2-yl)methoxy]-5-[2-(1H-tetrazol-5-yl)ethyl]thio)-5,11-dihydro[1]benzoxepino[3,4-b]pyridine
3-[7-(6,7-Difluoro-quinolin-2-ylmethoxy)-11-methyl-10,11-dihydro-5H-benzo[e]pyrido[2,3-b]azepin-5-ylsulfanyl]-propionic acid
3-[7-(7-Chloro-6-fluoro-quinolin-2-ylmethoxy)-11-methyl-10,11-dihydro-5H-benzo[e]pyrido[2,3-b]azepin-5-ylsulfanyl]-propionic acid
3-[9-chloro-7-(6,7-difluoro-quinolin-2-ylmethoxy)-5,11-dihydro[1]benzoxepino[3,4-b]pyridin-5-yl)thio]propanoic acid
ethyl 3-[7-(6,7-difluoro-quinolin-2-ylmethoxy)-5,11-dihydro[1]benzoxepino[3,4-b]pyridin-5-yl)thio]propanoate
3-[7-(6,7-difluoro-quinolin-2-ylmethoxy)-5,11-dihydro[1]benzoxepino[3,4-b]pyridin-5-yl)thio]propanamide
3-[7-(6,7-difluoro-quinolin-2-ylmethoxy)-2-methyl-5,11-dihydro[1]benzoxepino[3,4-b]pyridin-5-yl)thio]propanoic acid
3-[7-(6,7-difluoro-quinolin-2-ylmethoxy)-9-fluoro-5,11-dihydro[1]benzoxepino[3,4-b]pyridin-5-yl)thio]propanoic acid
3-[7-(6,7-difluoro-quinolin-2-ylmethoxy)-9-methyl-5,11-dihydro[1]benzoxepino[3,4-b]pyridin-5-yl)thio]propanoic acid
3{(7-[(E)-2-(6,7-difluoroquinolin-2-yl)vinyl]-5,11-dihydro[1]benzoxepino[3,4-b]pyrindin-5-yl)thio}propanamide
ethyl 3{(7-[(E)-2-(6,7-difluoroquinolin-2-yl)vinyl]-5,11-dihydro[1]benzoxepino[3,4-b]pyrindin-5-yl)thio}propanoate and pharmaceutically acceptable salts thereof.

In another aspect the present invention encompasses a synthetic process for the preparation of the compounds of formula (I) which is depicted in Scheme 1 and involves the synthesis of the products of the invention through an intermediate alcohol of formula (III) which is reacted with a mercaptane compound to yield the products of formula (I).

In still another aspect the present invention encompasses intermediate compounds of formula (III) useful in the synthesis of compounds of formula (I).

SCHEME 1

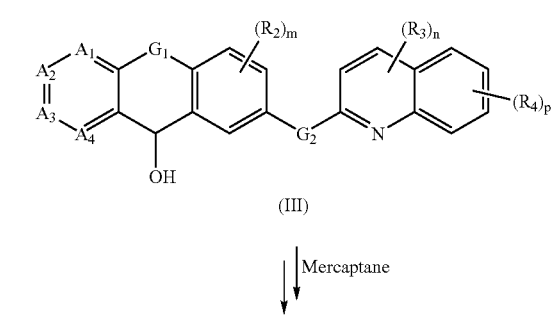

(III)

↓ Mercaptane

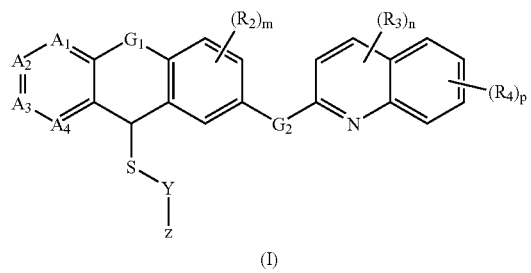

(I)

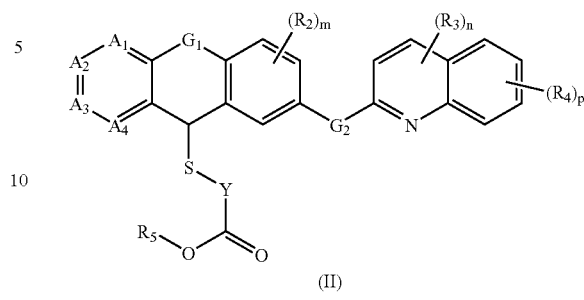

(II)

$R_5$ = H, alkyl

Particular executions of the general process depicted in Scheme 1 are depicted in Schemes 2 to 5 showing the synthesis of compounds of the invention. When Z=COOR$_5$ or CONR$_5$R$_5$ the compounds (II) can be prepared according to Schemes 2 or 12; when Z=5-tetrazolyl the route for the preparation of the compounds (V) is depicted in Scheme 3. In the case Z=NHSO$_2$R$_5$ or CONHSO$_2$R$_5$ the synthetic pathway to the compounds (VII) and (IX) is represented in Schemes 4 and 5, respectively.

Reaction Scheme 2

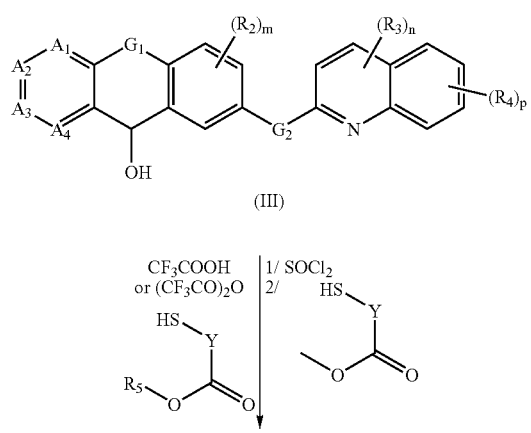

Following Scheme 2 the compounds (II) may be synthesised from the alcohols (III) via the trifluoroacetates (prepared in situ with trifluoroacetic acid or anhydride) or the chlorides (prepared with thionyl chloride). This reaction is carried at a temperature between 0° C. and 70° C. in an organic solvent, preferably a halogenated one and, more preferably, dichloromethane. The product (II) will be obtained as an ester (R$_5$=alkyl) if a mercaptoester is used and as a carboxylic acid (R$_5$=H) when a mercaptocarboxylic acid is used. Should it be desired to hydrolise the esters (II), R$_5$=alkyl to the corresponding acids (II), R=H this could be achieved preferably under alkaline conditions (i.e. using alkali hydroxides) in an organic solvent/water system at a temperature between 10° C. and 70° C. Among the organic solvents, THF, dioxane or alkanols are preferred.

Compounds in which Z is —CONR$_5$R$_5$ can be prepared by converting the corresponding acid to an acyl chloride by known techniques and subsequent reaction of the acyl chloride with an amine. For example, they can be prepared by reaction of an amine NHR$_5$R$_5$, with the acyl chloride derived from the corresponding acid (II).

Reaction Scheme 3

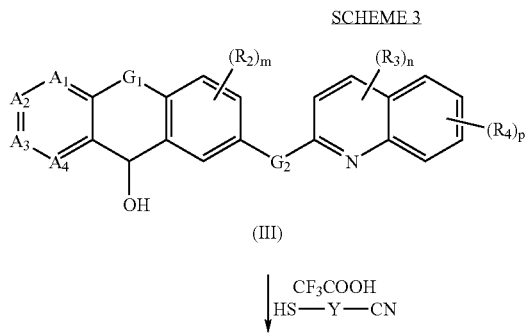

-continued

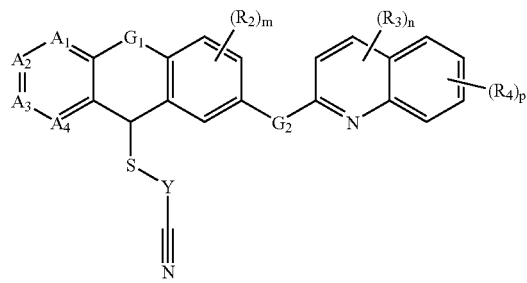

(IV)

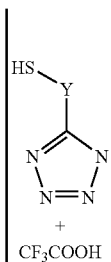

+ CF₃COOH

↓ RN₃

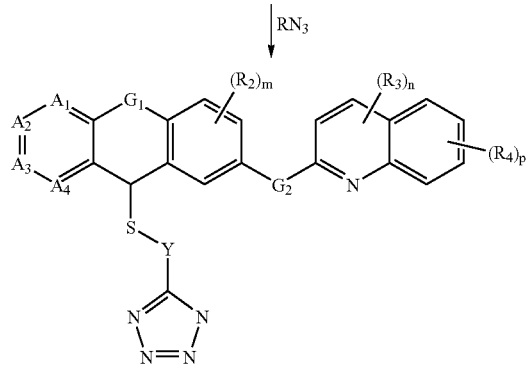

(V)

Scheme 3 shows two alternative methods for the preparation of the tetrazolyl derivatives. In a first method (shown on the left hand side of the scheme) the nitrites (IV) are prepared from the alcohols (III) in a very similar way to that described for the esters (II), but using mercaptonitriles instead of the corresponding mercaptoesters. The tetrazoles (V) are prepared from the nitrites (IV) using an azide compound such an alkali metal azide or an organotin azide, with the optional addition of an acidic compound such as a Lewis acid or an ammonium salt. This reaction can be carried with or without solvent at a temperature between 25° C. and 150° C.

In an alternative method (shown on the right hand side of the scheme) the tetrazolyl compounds (V) are obtained in a single step from the alcohols (III) by reaction with the tetrazolyl mercaptanes in conditions very similar to those described for the step leading from compounds (III) to compounds (IV).

Reaction Scheme 4

SCHEME 4

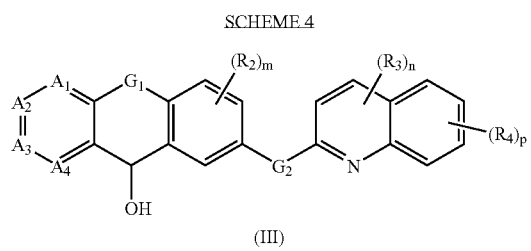

(III)

↓ (CF₃CO)₂O
  HS—Y—NH₂·HCl

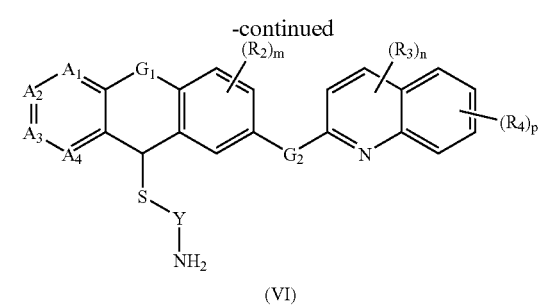

(VI)

↓ R₅SO₂X

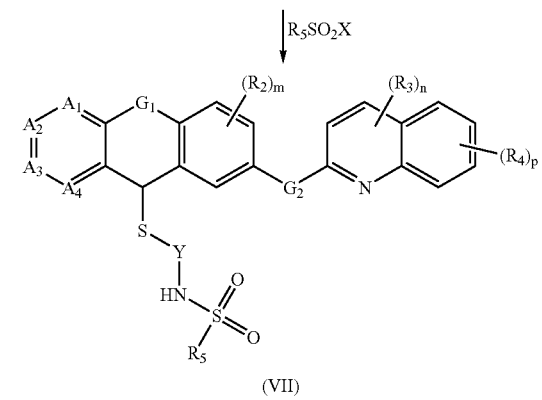

(VII)

Following the method depicted in Scheme 4, the amino compounds (VI) are prepared using a similar methodology to that described for esters (II) or nitriles (IV), but using a mercaptoamine hydrochloride instead of the corresponding mercaptoesters or mercaptonitriles. The sulfonamides (VII)

can be synthesised from the amine (VI) obtained in the previous step by direct acylation with a sulfonyl halide or anhydride in the presence of an acid scavenger such as a tertiary amine. This reaction is carried out in an inert solvent such as THF, DMF or Cl2CH2, at a temperature between 0° C. and 100° C.

Reaction Scheme 5

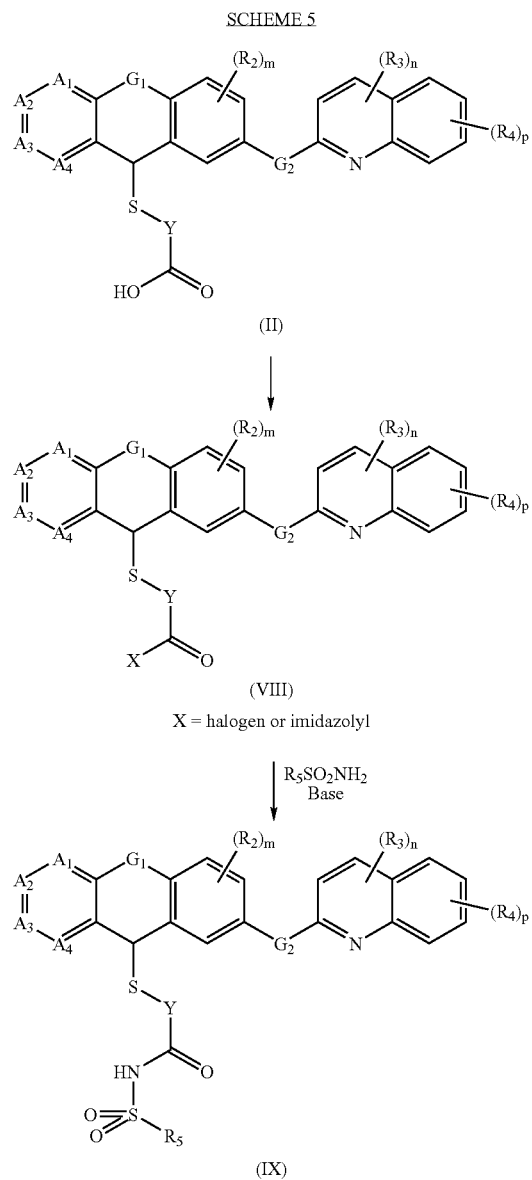

X = halogen or imidazolyl

Following the method depicted in Scheme 5, the carboxylic acids (II) are first transformed to an activated form (VII) such as an acyl halide or imidazolide. This intermediate is then reacted with a sulfonamide under alkaline conditions to yield the acylsulfonamide (IX).

The synthetic routes to the compounds (I) of the present invention presented so far make use of an alcohol of formula (III) as starting material. The alcohols of formula (III) may be synthesised following a number of alternative processes.

The alternative synthetic routes for the alcohols (III) share a step where the alcohols are obtained by reduction of the corresponding ketones (X) by means of reduction by known methods, such as treatment with sodium borohydride in lower alcohols or their mixtures with THF at temperatures between 0° C. and 25° C.

Depending on the nature of the group G2 a number of synthetic routes may be used for the preparation of the ketones (X). Schemes 6 and 7 may be followed when $G_2$ is —O—CH2, Scheme 8 may be followed when G2 is either —CH2-CH2- or —CH=CH—, Scheme 9 may be followed when G2 is —CH=CH— and finally Scheme 10 may be used when both G1 and G2 are —CH2-CH2-.

Reaction Scheme 6

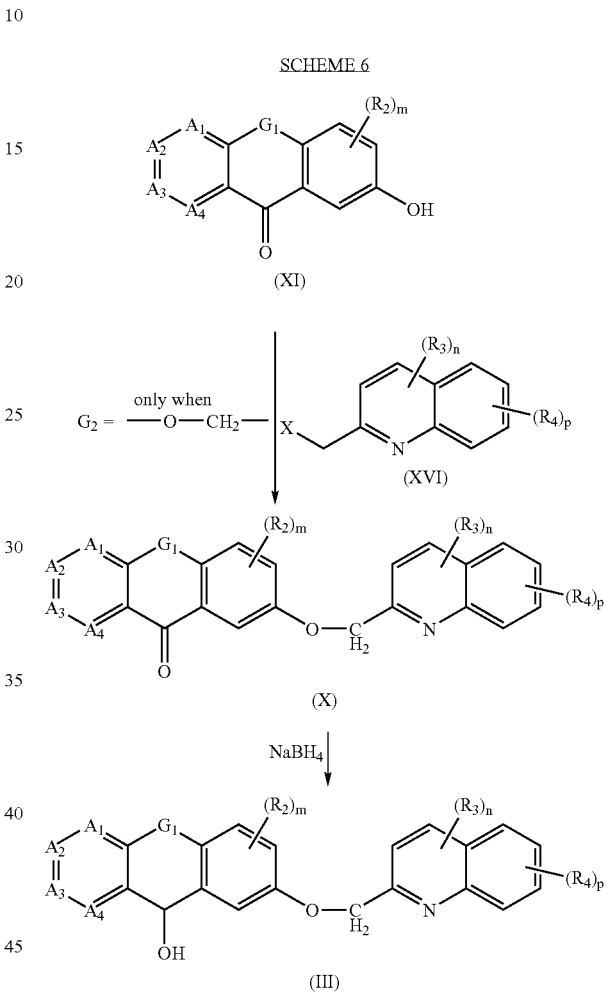

Scheme 6 may be followed when $G_2$ is —O—CH2. In this case the ketones (X) may be prepared, by alkylation of the corresponding phenols (XI) with 2-halomethylquinolines, which are obtained by halogenation of quinaldines as described in J. Med. Chem. (1992), 35, 3822-3844.

The reaction of alkylation of the phenols (XI) to give the compounds (X) is carried out in the presence of an alkali carbonate, such as potassium or caesium carbonate, or alternatively by first preparing the salt of the phenol by means of a metal alkoxide, sodium hydride or another basic agent. This reaction can be effected in a variety of solvents, such as DMF, aliphatic ketones, etc in a range of temperatures between 0° C. and 100° C.

The phenols (XI) are prepared from the corresponding methoxy derivatives (XII) by known methods such as treatment with Lewis acids as boron tribromide or protic acids such as hydrobromic acid, as showed in Scheme 7a or following the synthetic route showed in Scheme 7b.

Reaction Scheme 7a

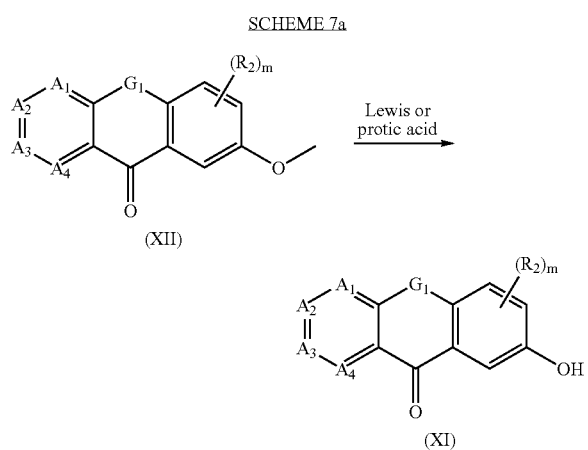

The demethylation reaction from (XII) to (XI) represented in Scheme 7 can be carried in a halogenated solvent in a range of temperatures from −60° C. to 30° C. (with Lewis acids) or with hydrobromic acid at 100-150° C.

The methoxy derivatives (XII) are prepared according to methods known in the literature; for example, in Synthesis, 1997(1), 113-116; J. Med. Chem., 1995, 38 (3), 496-507; DD 80449 (CA 76, 85803); Arzneim.-Forsch. (1972), 22(1), 133-7.

Reaction Scheme 7b

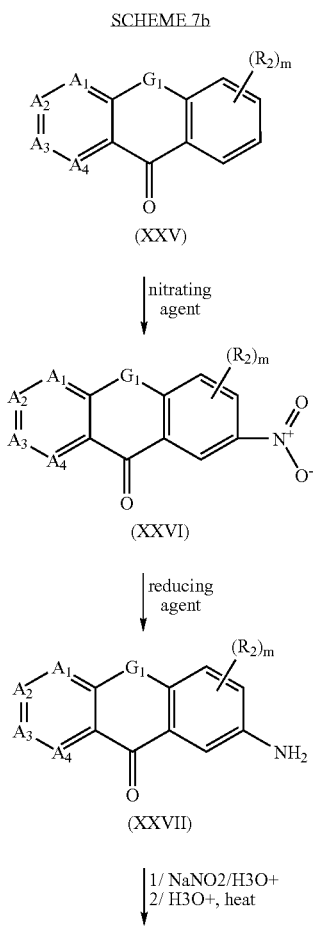

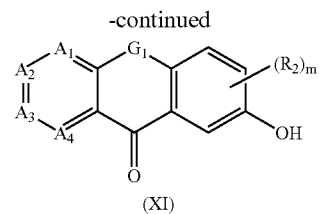

According to this synthetic scheme, compound (XXV) (which may be obtained according to DD 80449; CA 76:85803) is nitrated to the corresponding nitro derivative (XXVI) with the aid of a nitrating agent, for example with an alkali metal nitrate in sulphuric acid medium, at a temperature between −20 and 25° C. The nitro derivative (XXVI) is then reduced to the amine (XXVII) for example, with tin (II) chloride in acetic acid in a range of temperatures between 30 and 120° C. The amine (XXVII) is transformed into the phenol (XI) through the corresponding diazonium salt which is prepared by treating the amine in acidic media for example, acetic acid, with sodium nitrite, at temperatures between 5 and 40° C. The decomposition of the diazonium salt is effected 'in situ' typically at reflux temperature.

Reaction Scheme 8

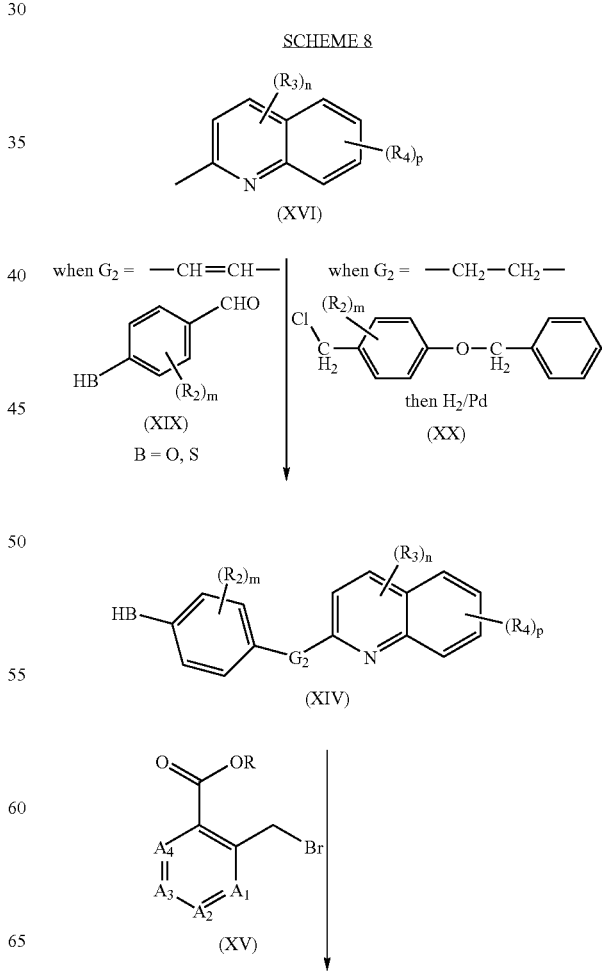

-continued

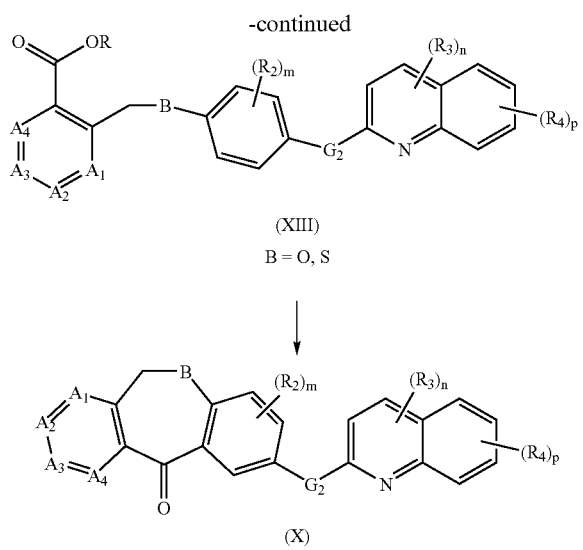

(XIII)
B = O, S (X)

The synthesis of (X) when $G_2$ is different from —O—CH2— and G1 is —CH2-O— or —CH2-S— is achieved through cyclization of the compound (XIII), as depicted in step 3 of synthetic Scheme 8. Compounds (XIII) are synthesised by reacting a phenol or thiophenol (XIV) with a benzyl halide (XV) as shown in step 2 of Scheme 8. The phenols or thiophenols (XIV), are in turn prepared from the corresponding quinaldines by reaction with 4-hydroxy benzaldehyde (XIX) (when $G_2$ is —CH=CH—) or with 4-benzyloxybenzyl chloride (XX) followed by subsequent debenzylation (when $G_2$ is —CH2-CH2-) represented in step 1 of scheme 8.

The quinaldines (XVI) are, in turn, prepared according to J. Heterocycl. Chem (1993), 301(1), 17-21.

In Scheme 8, the step involving condensation between quinaldines (XVI) and p-methoxybenzaldehyde (XIX) is carried out in xylene and acetic anhydride as condensing agent, at a range of temperatures between 100 and 200° C., and implies an ulterior alkaline hydrolysis of the phenyl acetate formed.

The reaction between the quinaldines (XVI) and the p-benzyloxybenzyl chloride (XX) involves the presence of a strong base, such as lithium diisopropylamide, and is typically carried out in THF as solvent, at a range of temperatures between −60° C. and 50° C.

The subsequent reaction involves the alkylation of the phenols or thiophenols (XIV) with the benzyl bromides (XV) and is effected in the presence of an alkali carbonate, such as potassium or caesium carbonate, or preparing first the salt of the phenol by means of a metal alkoxide, sodium hydride or another basic agent. This reaction can be effected in a variety of solvents, such as DMF, aliphatic ketones, etc in a range of temperatures between 0° C. and 100° C.

The cyclization of the acids derivatives (XIII) to the ketones (X) can also be effected in a variety of ways, for example, forming first an active anhydride with trifluoroacetic anhydride and then treating it with a Lewis acid such as boron trifluoride, or by direct treatment with a condensing agent, such as polyphosphoric acid. The reaction is carried out in halogenated solvents or without solvent, in a range of temperatures between 50° C. and 150° C.

Reaction Scheme 9

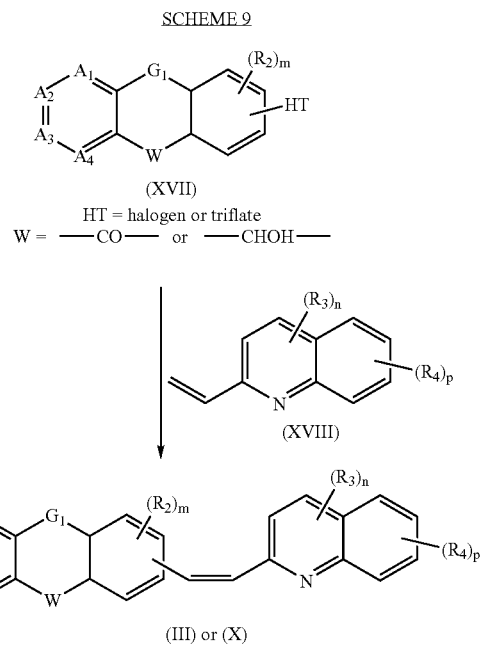

The synthesis of (III) or (X) when $G_2$ is —CH=CH— can also be achieved trough a coupling reaction between an appropriate halo or trifluoromethansulfonyl (triflate) derivative (XVII) and a 2-vinyl quinoline (XVIII), as shown in Scheme 9.

The coupling reaction shown in Scheme 9 is carried on the bromo derivatives which may be prepared according to the literature methods, like those described in WO 89/10369, J. Heterocycl. Chem. (1986), 23, 257 or J. Med. Chem. (1995), 38, 496 or on the trifluromethansulfonyl derivatives which may be prepared from the phenol derivatives (XI). The coupling reaction is catalysed with palladium salts and triarylphosphines and is run in an inert solvent such as dimethylformamide, THF or dioxane, at a temperature between 25 and 200° C.

Reaction Scheme 10

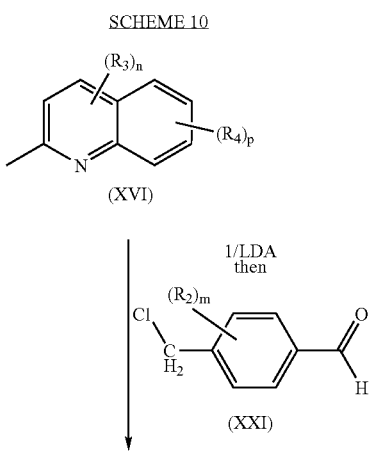

21

-continued

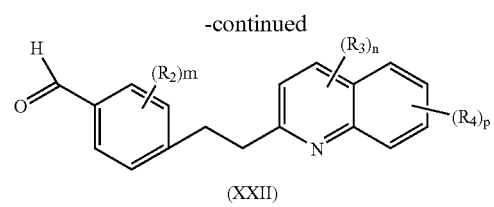

(XXII)

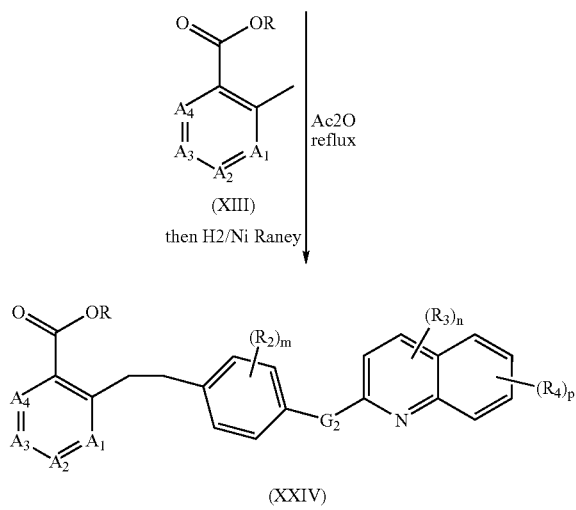

The synthesis of (X) when both G1 and G$_2$ are —CH2-CH2- is achieved through cyclization of the compound (XXIV), as depicted in step 3 of synthetic Scheme 10. Compounds (XXIV) are synthesised by reacting an aldehyde (XXII) with an o-methyl (aza)benzoate (XXIII) as shown in step 2 of Scheme 10. The aldehydes (XXII), are in turn prepared from the corresponding quinaldines (XVI) by reaction with o-chloromethyl benzaldehides (XXI) as represented in step 1 of scheme 10.

The quinaldines (XVI) are, in turn, prepared according to J. Heterocycl. Chem (1993), 301(1), 17-21.

In Scheme 10, the step involving condensation between quinaldines (XVI) and o-chloromethyl benzaldehides (XXI) is carried out in the presence of a strong base, such as lithium diisopropylamine, and is typically carried out in THF as solvent, at a range of temperatures between –60° C. and 50° C.

The subsequent reaction involves the condensation of the aldehydes (XXII) with an o-methyl (aza)benzoate (XXIII) and is effected in the presence of acetic anhydride at a temperature range between 100° C. and 200° C., typically at reflux temperature.

The cyclization of the acid derivatives (XXIV) to the ketones (X) can also be effected in a variety of ways, for example, forming first an active anhydride with trifluoroacetic anhydride and then treating it with a Lewis acid such as

22 boron trifluoride, or by direct treatment with a condensing agent, such as polyphosphoric acid. The reaction is carried out in halogenated solvents or without solvent, in a range of temperatures between 50° C. and 150° C.

Reaction Scheme 11

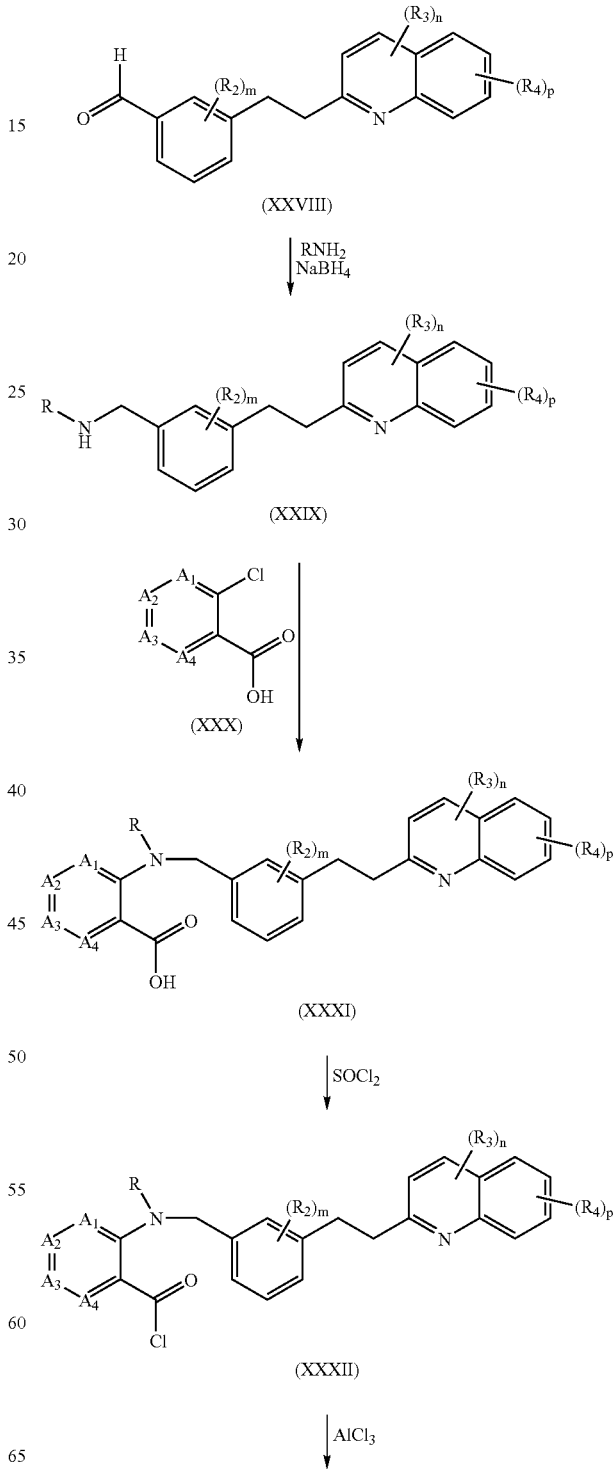

-continued

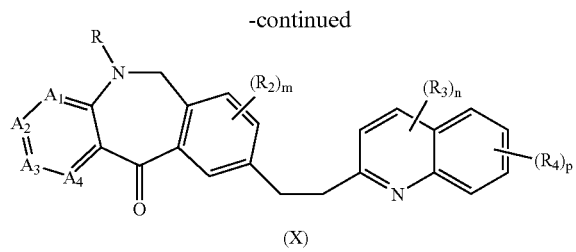

(X)

The synthesis of (X) when $G_2$ is —$CH_2$—$CH_2$— and G1 is —NR—$CH_2$— is achieved through the synthetic route showed in Scheme 11.

The aldehydes (XXVIII) are prepared according to J. Med. Chem., 1992, 35(21), 3832.

These aldehydes are transformed into the amines (XXIX) via reductive alkylation in alcoholic medium (typically methanol or ethanol) using sodium borohydride as reducing agent at a range of temperatures between 5 and 30° C.

The reaction of the amines (XXIX) with the chlorinated carboxylic acids (XXX) in a high boiling solvent as chlorobenzene at a range of temperatures between 100 and 140° C. gives the intermediate carboxylic acids (XXXI).

The carboxylic acids (XXXI) are reacted with a chlorinating agent such as thionyl chloride or oxalyl chloride with or without solvent (typically a chlorinated solvent) at a range of temperatures between 10 and 50° C. to yield the corresponding acyl chlorides (XXXII).

Finally the acyl chlorides (XXXII) are cyclized to the ketones (X) with the aid of a Lewis acid catalyst, typically aluminium chloride, in a usual solvent for the Friedel-Crafts reaction, as carbon disulfide or a chlorinated one, in a range of temperatures between 0 and 50° C.

Reaction Scheme 12

Scheme 12

As it has been said, the compounds of the present invention can exist in two enantiomeric forms. The processes described in Schemes 2 to 4 can be modified to allow the synthesis of the enantiomeric forms. The modification consists in that a mercaptan compound having a chiral centre is used to thioetherify the hydroxyl group of the tricyclic alcohols (III). The compound having a chiral centre has the general formula (XXXV)

(XXXV)

where Y' stands for a radical as defined under Y in which one hydrogen atom from one of the carbon atoms has been replaced by an amino group to yield a compound having a specific stereoisomery at the carbon atom whose hydrogen has been replaced. The use of compound (XXXV) having a chiral centre allows the preparation of compounds (II), (V), (VII), (IX) having two chiral centres: one at the carbon bearing the sulphur atom of the tricyclic ring system and another at the chiral carbon atom of the radical Y' as shown below:

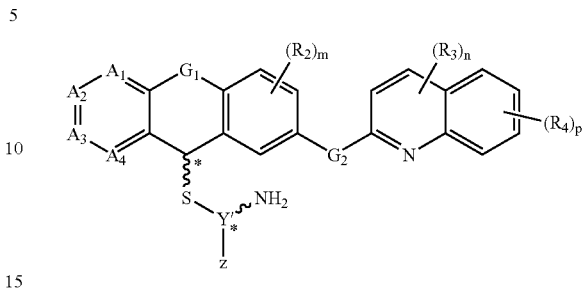

The co-existence of the two chiral centres generates four different diastereomers that can be separated by conventional physical techniques such as crystallization or chromatography. After separation, the amino group is removed by deamination using techniques known in the art.

This yields the chiral compounds:

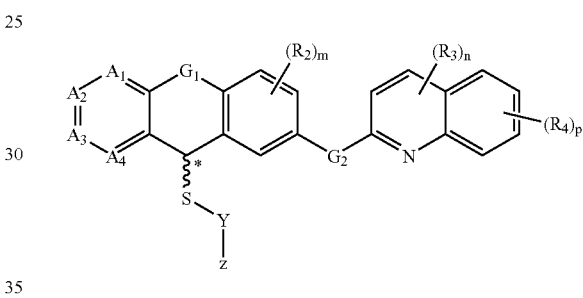

An example of this synthetic route for the case where $Z=COOR_5$ is depicted in Scheme 12. In this case deamination can be effected by direct deamination of the amino group with hydroxylamine O-sulphonic acid in basic aqueous medium as described in J. Am. Chem. Soc. 1978, 341-2 or with samarium (II) iodide as described in Chem. Commun. 1999, 1065-6. The deamination can also be run through reduction of the corresponding diazo derivative by means of hydroiodic acid (J. Am. Chem. Soc. 1943, 65, 1516; J. Chem. Soc. 1964, 3617) or tributyltin hydride (Tetrahedron 2000, 56(38), 7457-7461; Bull. Korean Chem. Soc. 1993, 14(6), 664-5). Another strategy consists in the reduction of the diazo derivative to the corresponding hydrazone by means of sodium borohydride in an organic solvent, preferably THF, and its posterior reduction of the methylene by treatment with a base, preferably a tertiary amine like DBU or N-methylmorpholine. The diazo derivative is prepared from the corresponding amino compound (XXXIII) by treatment with an alkyl nitrite, preferably isoamyl nitrite, in an inert solvent, preferably chloroform or dichloromethane, and in the presence of an organic acid, preferentially acetic acid, as described in Tetrahedron Lett. 1971, 47, 4495-8. Alternatively, the amino derivatives (XXXIII) can be converted to the corresponding isonitriles via formamides with phosphorus oxychloride or diphosgene (J. Chem. Research 1982, 79-80; J. Org. Chem. 1972 (3712), 187-190) and be subsequently reduced with tributyltin hydride as described in Synthesis 1980, 68-70.

SCHEME 12
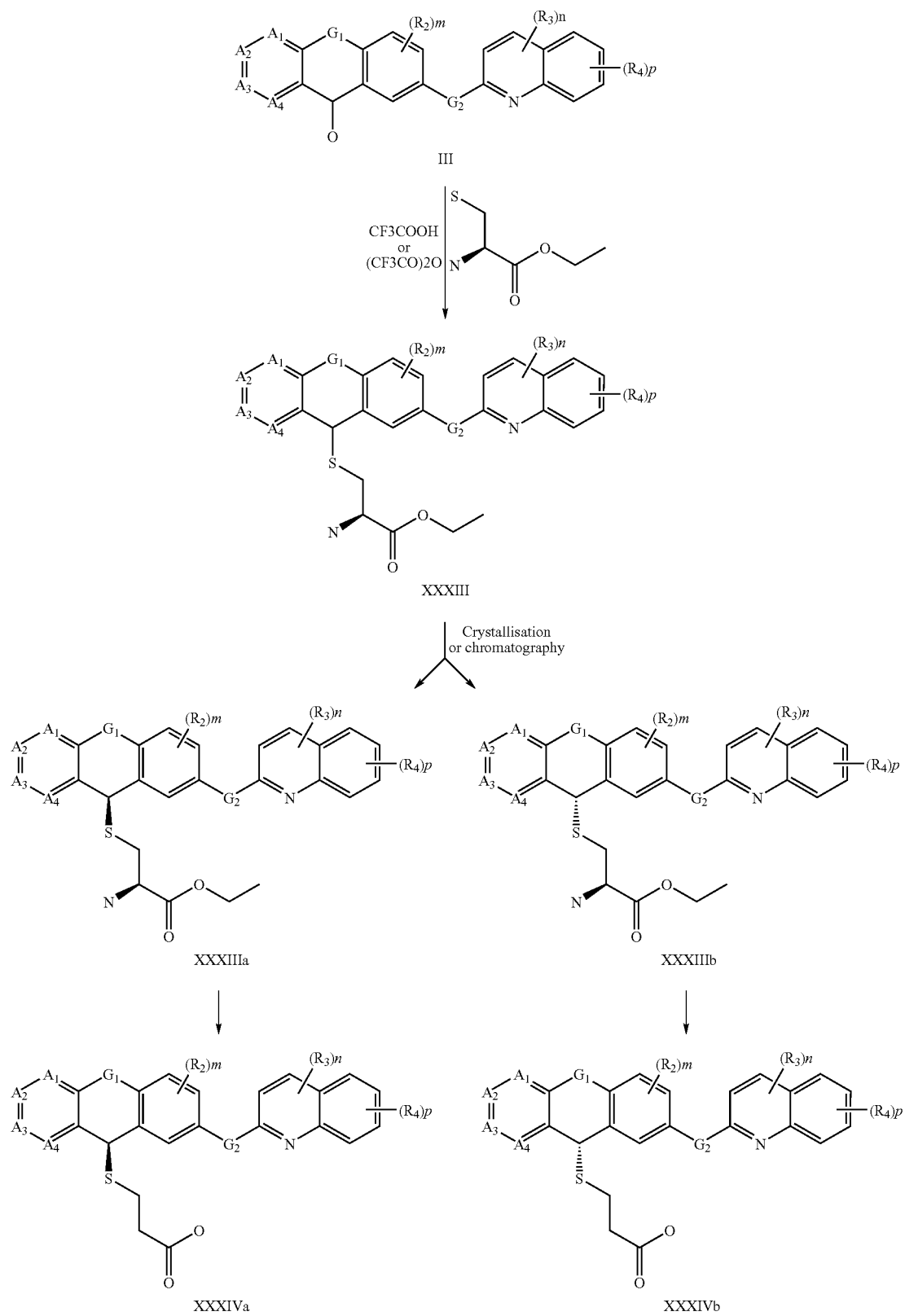

The L-cysteinyl derivative (XXXIII) is prepared from alcohols (III) and L-cysteine ethyl ester hydrochloride in acidic medium. This reaction is carried in very similar conditions to that described for Synthetic Scheme I (trifluoroacetic acid or anhydride or through the corresponding chloro derivative). The corresponding diastereomers of compound (XXXIII) are split by means of crystallisation in a variety of solvents of different range of polarities or through column chromatography on silica gel. The deamination of both isomers of (XXXIII) to the enantiomers (XXXIV) is achieved through any of the alternative routes described above.

Pharmacological Activity

CysLT1/LTD$_4$ Binding Protocol (Guinea-Pig Lung Membrane Preparation)

Guinea pigs were sacrificed and lung tissues removed. Connective tissue, trachea, large blood vessels and major airways were removed and the remaining tissue, primarily parenchyma, was homogenised in 20 volumes of 10 mM TRIS pH 7.4 containing 0.25M sucrose, 0.25 mM phenylmethylsulfonyl fluoride, 155 µg/ml benzenecarboximide, 5 µg/ml soybean trypsin inhibitor and 100 µg/ml bacitracin (Work Buffer), in a ULTRA-TURRAX T25 at 13500 rpm. The homogenate was centrifuged at 1000×g for 10 minutes at 4° C. The resulting supernatant was filtered through a sterile cloth and further centrifuged for 15 minutes at 40000×g at 4° C. The pellet obtained was resuspended in 10 volumes of Work Buffer, homogenised using a Potter (1100 rpm) and subjected to a final centrifugation step for 30 minutes at 40000×g at 4° C. This membrane pellet was finally resuspended in 10 volumes of 10 mM TRIS and 10 mM PIPES pH 7.4, and homogenised using a Potter (1100 rpm). Protein concentration was determined by the BRADFORD method using the Bio-Rad Protein Assay kit with BSA as standard. Protein aliquots were kept frozen at −80° C.

Radioligand Binding Assay

[$^3$H]LTD$_4$ (136.9 Ci/mmol) was obtained from NEN.

The assays were performed in a final volume of 250 µl of 10 mM PIPES pH 7.5 containing 10 mM CaCl$_2$, 10 mM MgCl$_2$, 50 mM NaCl, 2 mM L-Cysteine, 2 mM Glycine and 300 pM [$^3$H]LTD$_4$. The assay mixture also contained 200 µg of lung membrane protein/plate well. Non-specific binding was determined in the presence of zafirlukast 10 µM.

The assays were performed directly on Millipore Multiscreen GF/B plates, presoaked with 200 µl/well of assay buffer at room temperature. Incubations were conducted for 30 minutes at room temperature with continuous shaking. Separation of bound and free [$^3$H]LTD$_4$ was done by filtration through the plates that were then washed three times with 175 µl/wash of 10 mM TRIS containing 100 mM NaCl at 4° C. The plates were dried and counted in a TRILUX Microbeta Liquid Scintillation Counter of Wallac.

Specific binding routinely represented 80-90% of the total binding.

The results are shown in table I.

TABLE I

| Example | IC$_{50}$ nM |
|---|---|
| 1 | 0.38 |
| 3 | 0.27 |
| 4 | 0.28 |
| 7 | 0.14 |
| 8 | 0.50 |
| 9 | 0.59 |

TABLE I-continued

| Example | IC$_{50}$ nM |
|---|---|
| 11 | 0.27 |
| 12 | 0.35 |
| 18 | 0.33 |
| 23 | 0.34 |
| 24 | 0.60 |
| 25 | 0.67 |
| 28 | 2.00 |
| 33 | 0.50 |
| 34 | 1.20 |
| 35 | 0.35 |
| 40 | 0.50 |
| 43 | 3.40 |
| 44 | 0.20 |
| Compound A | 0.51 |
| Compound B | 0.52 |

Compound A is 3-[2-(7-chloro-6-fluoro-quinolin-2-ylmethoxy)-6,11-dihydro[1]dibenzoxepin-11-yl)thio]propanoic acid described in EP 0 685 478 A1.
Compound B is (1-{1-{3-[2-(7-Chloro-quinolin-2-yl)-vinyl]-phenyl}-3-[2-(1-hydroxy-1-methyl-ethyl)-phenyl]-propylsulfanylmethyl}-cyclopropyl)-acetic acid LTD4-Induced Microvascular Permeability in Guinea-Pigs Male Dunkin-Hartey guinea pigs (450-500 g) fasted for 18 hours were administered the test compounds by oral gavage 4 hours before being anesthetized with urethane (15%, i.p. 10 ml/kg). The left jugular vein was canulated under anaesthesia. Five minutes afterwards, Evans blue dye (40 mg/Kg) was injected intravenously. After five more minutes, LTD4 was administered (1 µg/kg, i.v.) to the animals in order to induce airway microvascular leakage. After yet another period of 5 minutes, animals were exsanguinated by cutting the right atria and the vascular bed was rinsed by perfusing 50 ml of saline solution through the left ventricle at a pressure of 150 cmH$_2$O. Then the trachea was excised and incubated in formamide for 20 hours at 55° C. to extract the Evans blue dye from the tissue. Microvascular permeability was determined by light spectrophotometry at 620 nm of the extravasated dye.

The results are shown in table II.

TABLE II

| Example | ED$_{50}$ mg/kg |
|---|---|
| 1 | 0.009 |
| 4 | 0.030 |
| 7 | 0.013 |
| 9 | 0.018 |
| 11 | 0.0013 |
| 23 | 0.002 |
| 24 | 0.010 |
| 34 | 0.018 |
| 35 | 0.009 |
| Compound A | 0.010 |
| Compound B | 0.008 |

Compound A is 3-[2-(7-chloro-6-fluoro-quinolin-2-ylmethoxy)-6,11-dihydro[1]dibenzoxepin-11-yl)thio]propanoic acid described in EP 0 685 478 A1.
Compound B is the commercially available LTD4 inhibitor Montelukast: 1-[[[(1R-1-[3-[(1E)-2-(7-chloro-2-quinolinyl)ethenyl]phenyl]-3-[2-(1-hydroxy-1-methylethyl)phenyl]propyl]thio]methyl]cyclopropaneacetic acid.

The results of tables I and II show that the compounds of formula (I) are potent leukotriene D4 antagonists and are therefore useful in the treatment or prevention of pathological conditions, diseases and disorders known to be susceptible of amelioration by inhibition of LTD4, such as bronchial asthma, allergic, and perennial rhinitis, chronic obstructive pulmonary disease, urticaria, atopic dermatitis, migraine, viral broncholitis caused by RSV, cystic fibrosis, eosinophilic, gastro-enteritis, fibromyalgia A and interstitial cystitis.

The compounds of the present invention can also be used in combination with other drugs known to be effective in the treatment of these diseases. For example, in combination with triptans or COX-2 inhibitors in the treatment of migraine; with H1 antagonists in the treatment of allergic disorders, such as rhinitis or urticaria; or with PDE IV inhibitors in the treatment of allergic disorders, asthma or chronic obstructive pulmonary disease.

Accordingly, another embodiment of the invention is the use of the compounds of formula (I) in the manufacture of a medicament for treatment or prevention of pathological conditions, diseases and disorders known to be susceptible of amelioration by inhibition of LTD4, as well as a method for treating a subject afflicted with a pathological condition or disease susceptible to amelioration by inhibition of LTD4, which comprises administering to said subject an effective amount of a compound of formula (I).

The present invention also provides pharmaceutical compositions which comprise, as an active ingredient, at least a compound of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent and a flavouring agent.

Compositions for parenteral injection may be prepared from soluble salts, which may or may not be freeze-dried and which may be dissolved in pyrogen free aqueous media or other appropriate parenteral injection fluid.

Compositions for topical administration may take the form of ointments, creams or lotions, all containing the compound of the invention; such preparations may be made by methods well-known in the art.

Effective doses are normally in the range of 10-600 mg of active ingredient per day. Daily dosage may be administered in one or more treatments, preferably from 1 to 4 treatments, per day.

The present invention will be further illustrated by the following examples. The examples are given by way of illustration only and are not to be construed as a limiting.

$^1$H Nuclear Magnetic Resonance Spectra were recorded on a Varian Gemini 200 spectrometer. Melting points were recorded using a Perkin Elmer DSC-7 apparatus. The chromatographic separations were obtained using a Waters 2690 system equipped with a Symmetry C18 (2.1×10 mm, 3.5 mM) column. The mobile phase was formic acid (0.4 ml), ammonia (0.1 ml), methanol (500 ml) and acetonitrile (500 ml) (B) and formic acid (0.46 ml), ammonia (0.115 ml) and water (1000 ml) (A): initially from 0% to 95% of B in 20 min, and then 4 min. with 95% of B. The reequilibration time between two injections was 5 min. The flow rate was 0.4 ml/min. The injection volume was 5 microliter. Diode array chromatograms were collected at 210 nM.

EXAMPLES

Example 1

Preparation of 3-{(7-[(6,7-difluoroquinolin-2-yl)methoxy]-5,11-dihydro[1]benzoxepino[3,4-b]pyridin-5-yl)thio}propanoic Acid Step 1:
7-Methoxy[1]benzoxepino[3,4-b]pyridin-5(11H)-one

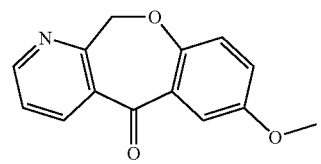

This compound was synthesised as described in Synthesis, 1997, 113-116.

Step 2:
7-Hydroxy[1]benzoxepino[3,4-b]pyridin-5(11H)-one

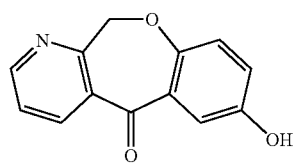

A solution of 9.7 ml (25.79; 0.10 mol) of boron tribromide in 125 ml of dichloromethane is cooled to −60° C. A solution of 10.0 g (41.45 mmol) of the product of step 1 in 40 ml of dichloromethane is dropped with stirring. Once the addition is complete, the system is allowed to reach room temperature. The stirring is continued during 16 h and 125 ml of water are carefully added. The pH is adjusted to 5 with 8N NaOH. The precipitated solid is filtered, water washed and dried. There are obtained 8.2 g (87%) of a brown solid, pure enough to continue with the synthesis.

Step 3: 6,7-difluoro-2-methylquinoline

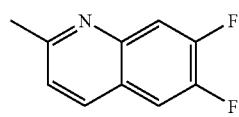

25.0 g of 3,4-difluoroaniline are dissolved in 120 of 2-butanol. 50 ml of a saturated solution of hydrogen chloride in 2-butanol are added slowly and afterwards 47.6 g (0.1936 mol) of p-chloranil are also added. With a good stirring and at reflux temperature (100-110° C.) a solution of 19.4 ml (0.236 mol) of crotonaldehyde in 45 ml of butan-2-ol is dropped slowly (ca. 2 hr). The whole is refluxed for two additional hours and then evaporated to dryness. The residue is taken with excess THF and is filtered and washed thoroughly with THF until the filtering appears to be uncoloured. The solid thus obtained is solved in water, filtered from some solid impurities and washed with ethyl ether. The aqueous layer is made slightly alkaline with 2N NaOH solution and then extracted with diethyl ether. The ethereal layer is dried and treated with a little decolourising charcoal. After evaporation a white solid is obtained (22.7 g, 65%).

Step 4: 2-(bromomethyl)-6,7-difluoroquinoline

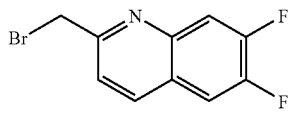

26.7 g of 6,7-difluoro-2-methylquinoline are dissolved in 300 ml of ethyl acetate. There are added 26.6 g of N-bromosuccinimide and a little quantity of benzoyl peroxide. The whole is refluxed with a heating bath at 90° C. for 16 hr and cooled to room temperature. The solid is filtered and discarded. The mother liquors are water washed, dried and concentrated. The residue is crystallised from ethyl ether/petroleum ether. There are obtained 18.6 g of bromo derivative (49%).

Step 5: 7-[(6,7-difluoroquinolin-2-yl)methoxy)[1]benzoxepino[3,4-b]pyridin-5(11H)-one

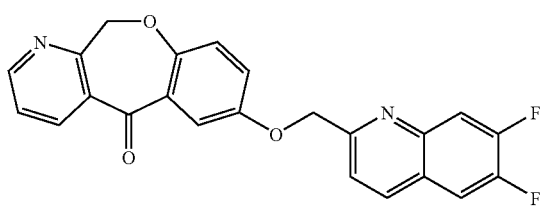

A suspension of 5.4 g (23.76 mmol) of the product of step 2 in 20 ml MeOH is added with 4.6 ml (23.76 mmol) of a 30% w/v solution of sodium methoxide in methanol. The solution thus obtained is evaporated to dryness and solved in 100 ml of DMF. There are added 6.1 g (23.76 mmol) of the product of step 4 in one portion and the whole is stirred at room temperature for 16 hr. The solvent is evaporated and the residue partitioned between water and methylene chloride. The organic layer is dried, concentrated and crystallised with diethyl ether. There are obtained 7.0 g of a white solid (73%).

Step 6: 7-[(6,7-difluoroquinolin-2-yl)methoxy)-5,11-dihydro[1]benzoxepino[3,4-b]pyridin-5-ol

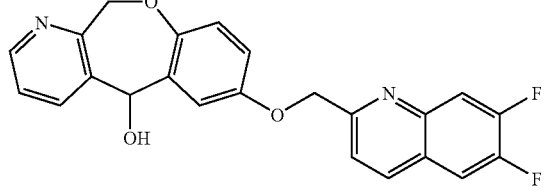

A suspension of 5.4 g (13.35 mmol) of the product of step 5 in 90 ml of THF and 30 ml of methanol is stirred with external ice bath cooling. There are added, 0.55 g (14.4 mmol) of sodium borohydride in little portions. Once the addition is finished the reaction is stirred for 1 hour, evaporated and 100 ml of water are added. The system is stirred for 30' and the solid is filtered and thoroughly washed with water. Once dried, the solid weights 5.3 g (97

$^1$HNMR (Cl3CD): 5.25 (AB syst. 2H); 5.31 (s. 2H); 5.79 (d. 1H); 6.85-6.95 (m. 1H); 7.05-7.23 (m. 3H); 7.51-7.70 (m. 2H); 7.78-7.90 (m. 2H); 8.14 (d. 1H); 8.44 (d. 1H).

Step 7: 3-{(7-[(6,7-difluoroquinolin-2-yl)methoxy]-5,11-dihydro[1]benzoxepino[3,4-b]pyrindin-5-yl)thio}propanoic Acid

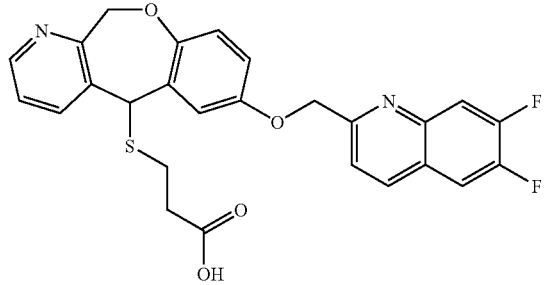

5.3 g (13.04 mmol) of the product of step 6 are suspended in 100 ml of dichloromethane. 45.25 ml (66.97 g; 587 mmol) of trifluoroacetic acid are added (the solid dissolves) and afterwards 2.27 ml (2.76 g; 26.05 mmol) of 3-mercaptopropanoic acid. The whole is stirred for 16 hr, excess water is added and the organic layer is washed thoroughly with water, with 0.5 N sol. of NaHCO3 and more water. The organic layer is dried, partly evaporated and ethyl ether is added to crystallise the product. There are obtained 5.5 g (85%) of pure product.

¹HNMR (Cl3CD): 2.60-2.83 (m. 4H); 5.05-5.78 (AB syst. 2H); 5.01 (s. 1H); 5.38 (s. 2H); 6.90-6.98 (m. 3H); 7.26-7.37 (m. 1H); 7.55-7.80 (m. 3H); 7.85-7.98 (m. 1H); 8.18-8.22 (m. 1H); 8.51-8.56 (m. 1H).

Example 2

Preparation of {(7-[(6,7-difluoroquinolin-2-yl) methoxy]-5,11-dihydro[1]benzoxepino[3,4-b]pyrindin-5-yl)thio}acetic Acid Step 1: Ethyl {(7-[(6,7-difluoroquinolin-2-yl) methoxy]-5,11-dihydro[1]benzoxepino[3,4-b]pyrindin-5-yl)thio}acetate

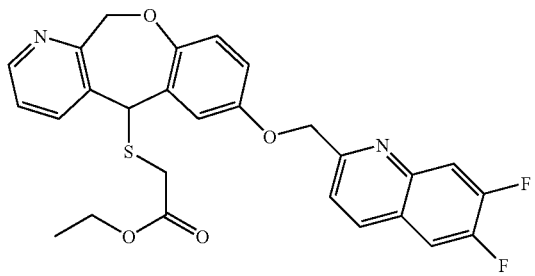

2.1 g (5.2 mmol) of the compound of the example 1, step 6 are suspended in 20 ml of dichloromethane. 18.2 ml (26.94 g; 236 mmol) of trifluoroacetic acid are added. The resulting solution is cooled to 0° C. and there are added 1.14 ml (1.25 g; 10.4 mmol) of ethyl mercaptoacetate. The whole is stirred at 0° C. for 2 h and sufficient saturated solution of Na2CO3 is added in order to neutralise the acidic medium. The organic layer is dried and concentrated. The residue is flash chromatographied through SiO2 eluting with a gradient Cl2CH2-Cl2CH2/MeOH 90/10. There are obtained 1.13 g (43%) of the corresponding ester.

Step 2: {(7-[(6,7-difluoroquinolin-2-yl) methoxy]-5,11-dihydro[1]benzoxepino[3,4-b]pyrindin-5-yl)thio}acetic Acid

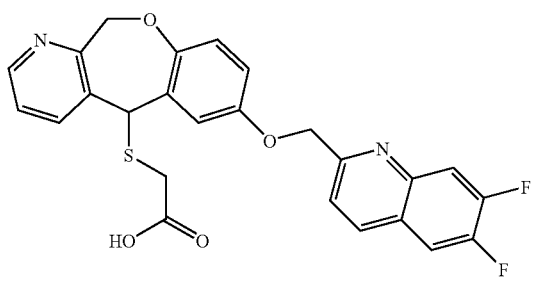

1.13 g of the product of step 1 are solved in a mixture of 10 ml EtOH and 10 ml THF. 2 ml of 2N NaOH are added and the reaction is stirred at room temperature for 16 h. 2N HCl is added until neutrality. More water is added and the product is extracted with dichloromethane. After flash chromatography through SiO2 eluting with Cl₂CH₂/MeOH 90/10 there are obtained 0.88 g (83%) of the product.

¹HNMR (Cl3CD): 3.25 (s. 2H); 4.98-5.85 (AB syst. 2H); 5.16 (s. 1H); 5.36 (s. 2H); 6.96-8.42 (m. 10H).

Example 3

Preparation of {(7-[(7-chloro,6-fluoro-quinolin-2-yl) methoxy]-5,11-dihydro[1]benzoxepino[3,4-b]pyrindin-5-yl)thio}acetic Acid Step 1: 7-chloro-6-fluoro-2-methylquinoline

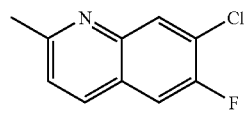

This compound is prepared according to J. Het Chem. 30, 17 (1993).

Step 2: 2-(bromomethyl)-7-chloro-6-fluoroquinoline

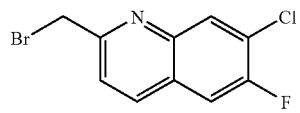

26.8 g of the product of step 1 are dissolved in 300 ml of ethyl acetate. 24.4 g of N-bromosuccinimide and a little benzoyl peroxide are added, and the mixture is refluxed at 90° C. (bath temperature) for 16 h. When the solution reaches room temperature it is washed with water, dried and concentrated to a little volume. The crystallised solid is filtered and washed with ethyl ether/petroleum ether 1:1. It weighs 16.2 g. The mother liquors are concentrated and flash chromatographied through SiO2 eluting with dichloromethane. There is obtained an additional amount of 3.5 g of product (global yield: 52%).

Step 3: 7-[(7-chloro-6-fluoro-quinolin-2-yl)methoxy) [1]benzoxepino[3,4-b]pyrindin-5(11H)-one

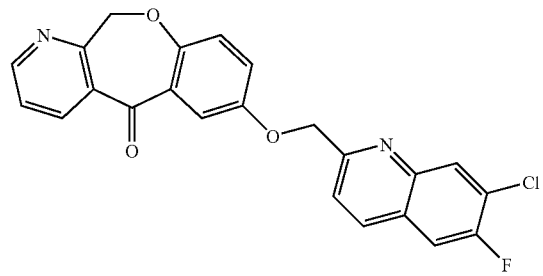

This compound was synthesised using the procedure showed in Example 1 Step 5 but substituting the 2-(bromomethyl)-7-chloro-6-fluoroquinoline for the 2-(bromomethyl)-6,7-difluoroquinoline. The yield in this case was 68%.

Step 4: 7-[(7-chloro-6-fluoroquinolin-2-yl)methoxy)-5,11-dihydro[1]benzoxepino[3,4-b]pyridin-5-ol

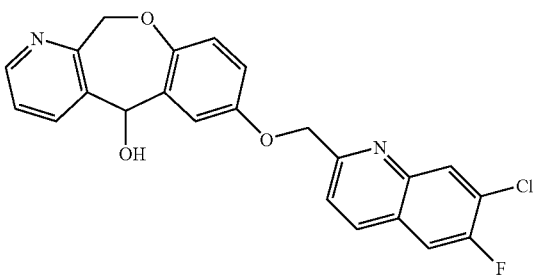

This compound was synthesised using the procedure showed in Example 1 Step 6 but substituting the 7-[(7-chloro-6-fluoro-quinolin-2-yl)methoxy)[1]benzoxepino[3,4-b]pyridin-5(11H)-one for 7-[(6,7-difluoroquinolin-2-yl)methoxy)[1]benzoxepino[3,4-b]pyridin-5(11H)-one the. The yield was 91%.

Step 5: Ethyl {(7-[(7-chloro-6-fluoro-quinolin-2-yl)methoxy]-5,11-dihydro[1]benzoxepino[3,4-b]pyrindin-5-yl)thio}acetate

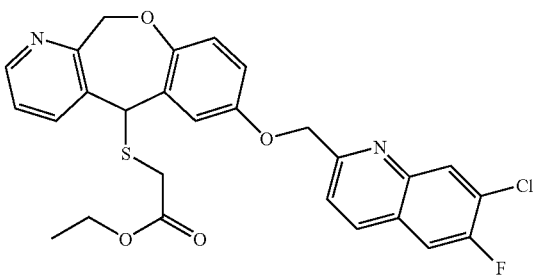

2.19 g (5.2 mmol) of the compound of the step 4 are suspended in 20 ml of dichloromethane. 18.2 ml (26.94 g; 236 mmol) of trifluoroacetic acid are added. The resulting solution is cooled to 0° C. and there are added 2.85 ml (3.12 g; 26 mmol) of ethyl mercaptoacetate. The whole is stirred at room temperature for 3 h and sufficient saturated solution of Na2CO3 is added in order to neutralise the acidic medium. The organic layer is dried and concentrated. The residue is flash chromatographied through SiO2 eluting with a gradient Cl2CH2-Cl2CH2/MeOH 90/10. There are obtained 1.74 g (64%) of the corresponding ester.

Step 6: {(7-[(7-chloro,6-fluoro-quinolin-2-yl) methoxy]-5,11-dihydro[1]benzoxepino[3,4-b]pyrindin-5-yl)thio}acetic Acid

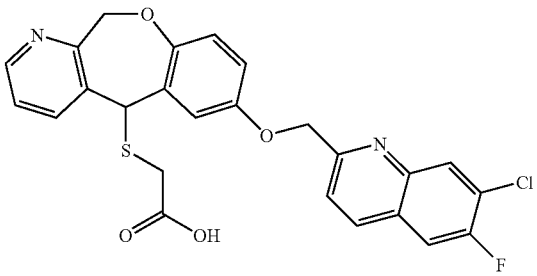

Starting from the product obtained in step 5 and using the same procedure than in Example 2, step 2, the corresponding acid is obtained in 66% yield.

$^1$HNMR (Cl3CD): 3.32 (s. 2H); 4.99-5.73 (AB syst. 2H); 5.16 (s. 1H); 5.30 (s. 2H); 6.92-6.97 (m. 2H); 7.05-7.07 (m. 1H); 7.22-7.26 (m. 1H); 7.56-7.59 (m. 1H); 7.70-7.76 (m. 2H); 8.15-8.20 (m. 2H); 8.42-8.44 (m. 1H).

Example 4

Preparation of 3-{(7-[(7-chloro,6-fluoro-quinolin-2-yl)methoxy]-5,11-dihydro[1]benzoxepino[3,4-b]pyrindin-5-yl)thio}propanoic Acid Step 1: Ethyl 3-{(7-[(7-chloro,6-fluoro-quinolin-2-yl)methoxy]-5,11-dihydro[1]benzoxepino[3,4-b]pyrindin-5-yl)thio}propanoate

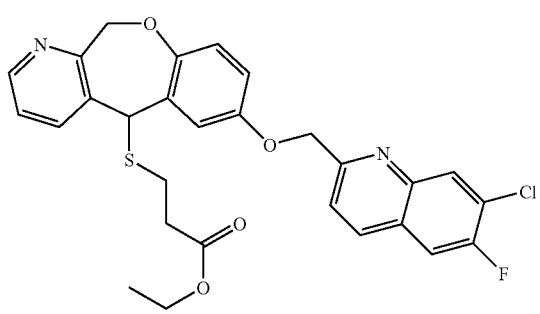

2.19 g (5.2 mmol) of the compound of the Example 3 step 4 are suspended in 20 ml of dichloromethane. 18.2 ml (26.94 g; 236 mmol) of trifluoroacetic acid are added. The resulting solution is cooled to 0° C. and there are added 3.30 ml (3.48 g; 26 mmol) of ethyl 3-mercaptopropanoate. The whole is stirred at room temperature for 3 h and sufficient saturated solution of Na2CO3 is added in order to neutralise the acidic medium. The organic layer is dried and concentrated. The residue is flash chromatographied through SiO2 eluting with a gradient Cl$_2$CH$_2$—Cl$_2$CH$_2$/MeOH 90/10. There are obtained 1.95 g (70%) of the corresponding ester.

Step 2: 3-{(7-[(7-chloro,6-fluoro-quinolin-2-yl)methoxy]-5,11-dihydro[1]benzoxepino[3,4-b]pyrindin-5-yl)thio}propanoic Acid

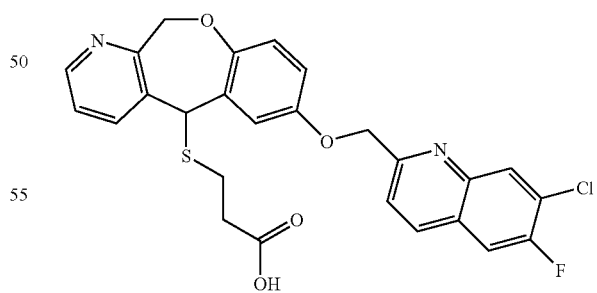

Starting from the product obtained in step 1 and using the same procedure than in Example 2, step 2, the corresponding acid is obtained in 82% yield.

$^1$HNMR (Cl3CD): 2.57-2.75 (m. 4H); 5.00-5.72 (AB syst. 2H); 4.90 (s. 1H); 5.30 (s. 2H); 6.86-7.01 (m. 3H); 7.15-7.19 (m. 1H); 7.48-7.51 (m. 1H); 7.61-7.67 (m. 2H); 8.08-8.18 (m. 2H); 8.44-8.47 (m. 1H).

Example 5

Preparation of [{(7-[(6,7-difluoroquinolin-2-yl)methoxy]-5,11-dihydro[1]benzoxepino[3,4-b]pyridin-5-yl)thio}methyl]benzoic Acid Step 1: Methyl 3-(bromomethyl)benzoate

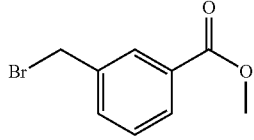

A mixture of 5.5 g (36 mmol) of methyl 3-methylbenzoate, 7.1 g (39.5 mmol) of N-Bromosuccinimide and 0.44 g (1.8 mmol) of benzoyl peroxide in 75 ml of Cl4C is refluxed for 5 h. The solid is filtered and washed with Cl4C. The mother liquors are concentrated and a yellow solid is obtained which is, essentially, monobromated product. This is used in the next step without further purification.

Step 2: 3-(mercaptomethyl)benzoic Acid

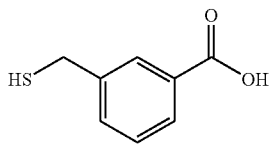

This compound is synthesised according to Gazz. Chim. Ital., 1969, 99 (12), 1306.

Step 3: [{(7-[(6,7-difluoroquinolin-2-yl)methoxy]-5,11-dihydro[1]benzoxepino[3,4-b]pyridin-5-yl)thio}methyl]benzoic Acid

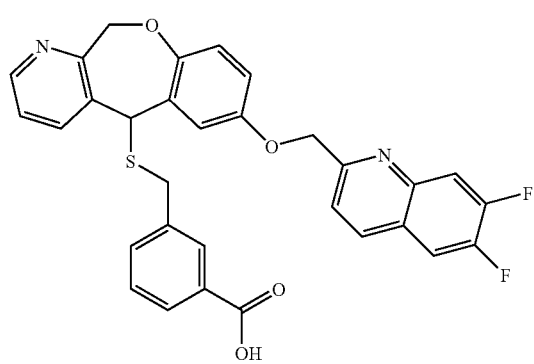

This compound was prepared in 96% yield according to the procedure of Example 1 step 7 replacing the 3-mercaptopropanoic acid for the 3-(mercaptomethyl)benzoic acid. The final purification, in this case, was achieved by means of flash chromatography through $SiO_2$ eluting with a gradient $Cl_2CH_2$—$Cl_2CH_2$/AcOEt 90:10.

$^1$HNMR (Cl3CD): 3.66 (AB syst. 2H); 5.01-5.76 (AB syst. 2H); 4.60 (s. 1H); 5.31 (AB syst. 2H); 6.77-6.78 (m. 1H); 6.91-6.95 (m. 1H); 7.05-7.08 (m. 1H); 7.17-7.21 (m. 1H); 7.35-7.59 (m. 4H); 7.68-7.71 (m. 1H); 7.83-7.89 (m. 1H); 7.97-8.01 (m. 1H); 8.06 (s. 1H); 8.16-8.19 (m. 1H); 8.43-8.45 (m. 1H).

Example 6

Preparation of [{(7-[(7-chloro,6-fluoro-quinolin-2-yl)methoxy]-5,11-dihydro[1]benzoxepino[3,4-b]pyrindin-5-yl)thio}methyl]benzoic Acid

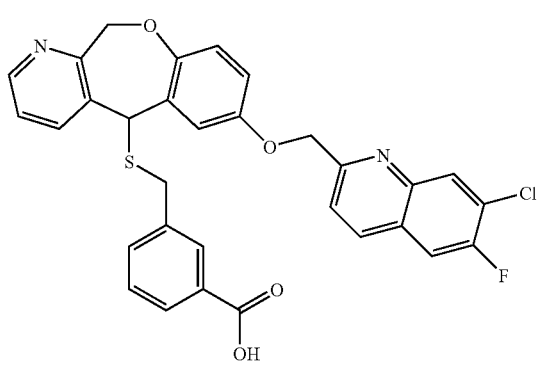

This compound was prepared in 85% yield starting with the compound of Example 3 Step 4 and using the procedure of Example 5 Step 3 (S3cheme 6):

$^1$HNMR (Cl3CD): 3.59 (s. 2H); 5.00-5.75 (AB syst. 2H); 4.63 (s. 1H); 5.30 (s. 2H); 6.76-6.77 (m. 1H); 6.91-6.95 (m. 1H); 7.05-7.08 (m. 1H); 7.19-7.24 (m. 1H); 7.40-7.56 (m. 4H); 7.70-7.72 (m. 1H); 7.96-8.02 (m. 2H); 8.16-8.19 (m. 2H); 8.41-8.43 (m. 1H).

Example 7

Preparation of 1-{[(7-[(6,7-difluoroquinolin-2-yl)methoxy]-5,11-dihydro[1]benzoxepino[3,4-b]pyrindin-5-yl)thio]methyl}cyclopropyl Acetic Acid Step 1: Methyl [1-Mercaptomethyl)cyclopropyl]acetate

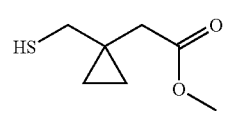

This compound was prepared according to Bioorg. Med. Chem. Lett, 1995, 5 (3), 286.

Step 2: 1-{[(7-[(6,7-difluoroquinolin-2-yl)methoxy]-5,11-dihydro[1]benzoxepino[3,4-b]pyrindin-5-yl)thio]methyl}cyclopropyl Acetic Acid

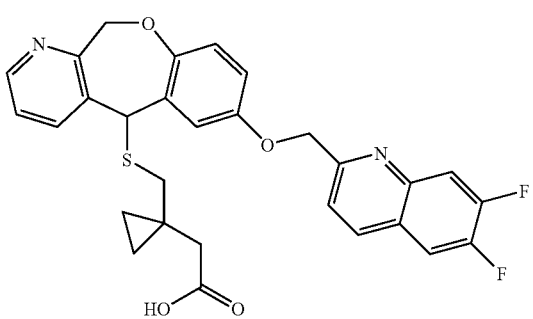

This compound was synthesised in 25% yield starting from the product-described in Example 1, Step 6 and according to the procedure described in Example 2 step 1 and 2.

¹HNMR (Cl3CD): 0.40-0.53 (m. 2H); 0.58-0.68 (m. 2H); 2.32-2.55 (AB syst. 2H); 2.70-2.78 (AB syst. 2H); 4.75 (s. 1H); 5.00-5.69 (AB syst. 2H); 5.37-5.44 (AB syst. 2H); 6.88-6.91 (m. 2H); 7.01-7.04 (m. 1H); 7.12-7.16 (m. 1H); 7.56-7.62 (m. 2H); 7.67-7.70 (m. 1H); 7.96-8.02 (m. 1H); 8.18-8.21 (m. 1H); 8.42-8.44 (m. 1H).

Example 8

Preparation of 3-{(7-[(6,7-difluoroquinolin-2-yl)methoxy]-5,11-dihydro[1]benzoxepino[3,4-b]pyridin-5-yl)thio}-2,2-dimethylpropanoic Acid Step 1

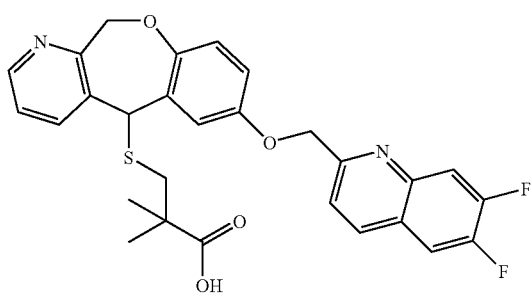

0.25 g (0.621 mmol) of the product of Example 1, step 6 are suspended in 5 ml of dichloromethane. 2.17 ml (3.21 g; 28.18 mmol) of trifluoroacetic acid are added. The solution is cooled to 0° C. and 0.46 g (3.1 mmol) of methyl 3-mercapto-2,2-dimethylpropanoate are added. After stirring at room temperature for 16 hr sufficient saturated solution of Na2CO3 is added in order to neutralise the acidic medium. The organic layer is dried and concentrated. The residue is flash chromatographied through SiO₂ eluting with Cl₂CH₂/MeOH 95/5. There are obtained 0.147 g (43%) of the corresponding ester, which is dissolved in 5 ml ethanol. 1 ml of 1N NaOH is added and the system stirred for 16 hr. More water is added and the product is extracted with dichloromethane. After flash chromatography through SiO₂ eluting with Cl₂CH₂/MeOH 90/10 there are obtained 0.08 g (59%) of the product.

¹HNMR (Cl3CD): 1.28 (s. 6H); 2.52-2.84 (AB syst. 2H); 4.90 (s. 1H); 4.98-5.75 (AB syst. 2H); 5.34 (s. 2H); 6.83-6.90 (m. 3H); 7.10-7.19 (m. 1H); 7.50-7.67 (m. 3H); 7.85-7.98 (m. 1H); 7.10-7.19 (m. 1H); 8.41-8.44 (m. 1H).

Example 9

Preparation of 3-{(7-[(6,7-difluoroquinolin-2-yl)methoxy]-5,11-dihydro[1]benzoxepino[3,4-b]pyridin-5-yl)thio}-3methylbutanoic Acid Step 1: 3-mercapto-3-methyl-butanoic Acid

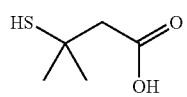

This compound is prepared according to J. Chem. Soc. Perkin trans. 1, 1992, 1215.

Step 2: 3-{(7-[(6,7-difluoroquinolin-2-yl)methoxy]-5,11-dihydro[1]benzoxepino[3,4-b]pyrindin-5-yl)thio}-3methylbutanoic Acid

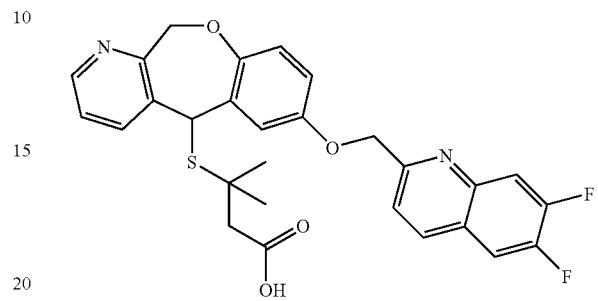

This compound is prepared in 69% yield according to Example 1, step 7.

¹HNMR (Cl3CD): 1.29 (s. 3H); 1.42 (s. 3H); 2.58 (s. 2H); 4.96-5.70 (AB syst. 2H); 5.06 (s. 1H); 5.34 (s. 2H); 6.85-6.89 (m. 1H); 6.97-7.03 (m. 2H); 7.09-7.13 (m. 1H); 7.53-7.68 (m. 3H); 7.87-7.94 (m. 1H); 8.13-8.16 (m. 1H); 8.41-8.43 (m. 1H).

Example 10

Preparation, of 3-{(7-[(E)-2-(6,7-difluoroquinolin-2-yl)vinyl]-5,11-dihydro[1]benzoxepino[3,4-b]pyridin-5-yl)thio}propanoic Acid Step 1: 2-[(4-bromophenoxy)methyl]nicotinic Acid

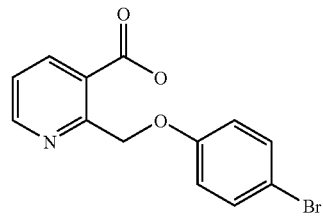

32 g (185 mmol) of 4-bromophenol are treated in methanol with 33.32 g (185 mmol) of 30% solution of sodium methoxide in methanol. The solvent is eliminated and the residue mixed with 5.0 g (37.00 mmol) of furo[3,4-b]pyridin-5(7H)-one (prepared according to Synthesis, 1997, 113-116). The system is stirred at 165° C. for 30' (at first the mixture melts, afterwards solidifies). Once at room temperature, the solid is dissolved in excess water, adjusted at pH 7-8 with 2N HCl and extracted two times with dichloromethane. The aqueous layer is adjusted at pH 5-6 with more 2N HCl and the solid that precipitates is filtered, washed with water and dried. The yield is 6.6 g (58%).

Step 2:
7-bromo[1]benzoxepino[3,4-b]pyridin-5(11H)-one

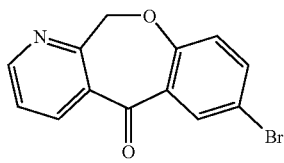

6.6 g (22.75 mmol) of the product of the previous step is stirred with 132 g of PPA at 165° C. for 8 hr. The mixture is poured over ice/water and basified with 8N NaOH. The solid is filtered, washed with water and dried. Yield 3.0 g (48%).

Step 3: 7-bromo-5,11-dihydro[1]benzoxepino[3,4-b]pyridin-5-ol

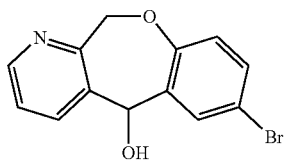

0.4 g (1.37 mmol) of the product of the previous step is dissolved in 8 ml THF plus 4 ml MeOH. The solution is stirred at 5° C. and 0.064 g (1.68 mmol) of sodium borohydride are added in portions. The system is stirred 2 hr at room temperature, concentrated in vacuo and the residue stirred with water, filtered and dried. Yield 0.37 g (92%).

Step 4: 6,7-difluoro-2-vinylquinoline

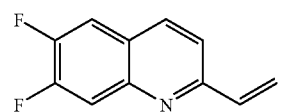

This compound was synthesised in a 34% global yield according with J. Org. Chem. 1996, 61, 3398-3405, but starting from the product of Example 1, step 3.

Step 5: 7-[(E)-2-(6,7-difluoroquinolin-2-yl)vinyl]-5,11-dihydro[1]benzoxepino[3,4-b]pyridin-5-ol

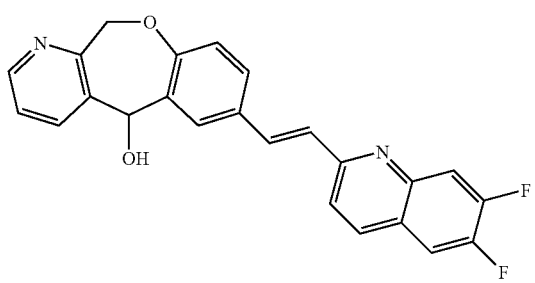

0.37 g (1.26 mmol) of the bromo derivative of step 3 are mixed with 0.27 g (1.41 mmol) of the vinyl derivative of step 4, 8.5 mg (0.0378 mmol) of palladium acetate and 36.2 mg (0.118 mmol) of tri(o-tolyl)phosphine in 2.5 ml of DMF. The solution is degassed and cooled with an ice bath. In a nitrogen atmosphere it is dropped inside a solution of 0.27 ml (0.196 g; 1.937 mmol) of N,N,N-triethylamine in 1.2 ml DMF. The whole is stirred at 100° C. for 1 hr. Once at room temperature, 4 ml of water are dropped inside and the solid is filtered, washed with water and dried. The yield is 0.5 g (98%).

Step 6: 3-{(7-[(E-2-(6,7-difluoroquinolin-2-yl)vinyl]-5,11-dihydro[1]benzoxepino[3,4-b]pyrindin-5-yl)thio}propanoic Acid

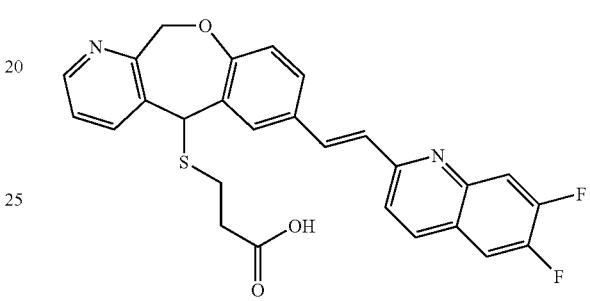

A mixture of 0.20 g (0.49 mmol) of the product of the previous step, 0.087 ml (0.105 g; 1.0 mmol) of 3-mercaptopropanoic acid and 1.15 ml (1.698 g; 14.91 mmol) of trifluoroacetic acid in 4 ml of dichloromethane is stirred at room temperature for 16 hr. The solvents are evaporated at room temperature, the residue is partitioned in ethyl acetate/water and the organic layer is washed with a little solution 1M of sodium hydrogen carbonate. The solution is dried, concentrated, and the residue is stirred with ethyl ether and filtered, giving 0.16 g (65%) of the product.

$^1$HNMR (d$^6$-DMSO): 2.56 (d. 2H); 2.65 (d. 2H); 5.00-6.03 (AB syst. 2H); 5.38 (s. 2H); 7.01 (d. 1H); 7.35-7.43 (m. 2H); 7.63 (d. 1H); 7.62-7.97 (m. 6H); 8.36 (d. 1H); 8.51-8.52 (m. 1H); 12.34 (s. 1H).

Example 11

Preparation of 1-{[(7-[(E)-2-(6,7-difluoroquinolin-2-yl)vinyl]-5,11-dihydro[1]benzoxepino[3,4-b]pyrindin-5-yl)thio]methyl}cyclopropyl Acetic Step 1: [1-mercaptomethyl)cyclopropyl]acetic Acid

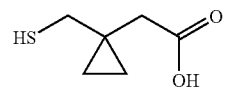

This compound is prepared according to U.S. Pat. No. 5,523,477 (1996).

Step 2: 1-{[(7-[(E)-2-(6,7-difluoroquinolin-2-yl)vinyl]-5,11-dihydro[1]benzoxepino[3,4-b]pyrindin-5-yl)thio]methyl}cyclopropyl Acetic

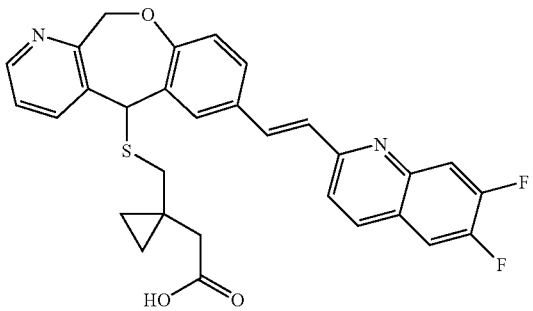

Starting from 0.2 g of the product of Example 10, step 5, and according to step 6 of the same Example, this compound is prepared in 25% yield.

$^1$HNMR (d$^6$-DMSO): 0.39-0.46 (m. 4H); 2.25 (s. 2H); 2.56-2.80 (AB syst. 2H); 5.00-6.07 (AB syst. 2H); 5.25 (s. 1H); 6.99 (d. 1H)); 7.34-7.40 (m. 2H); 7.62-7.99 (m. 7H); 8.36 (d. 1H); 8.48-8.50 (m. 1H); 11.95-12.30 (b.s. 1H)

Example 12

Preparation of {(7-[(E)-2-(6,7-difluoroquinolin-2-yl)vinyl]-5,11-dihydro[1]benzoxepino[3,4-b]pyrindin-5-yl)thio}acetic Acid

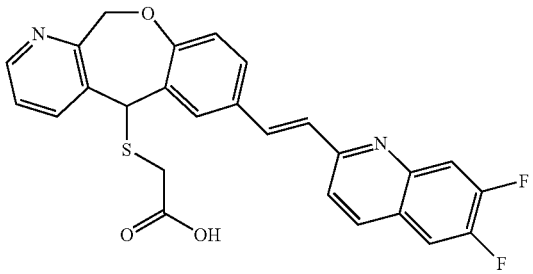

Starting from 0.2 g of the product of Example 10, step 5 and 0.09 g of mercaptoacetic acid, and according to step 6 of the same Example, this compound is prepared in 43% yield.

$^1$HNMR (d$^6$-DMSO): 3.30 (s. 2H); 5.01-6.04 (AB syst. 2H); 5.39 (s. 1H); 7.03 (d. 1H); 7.34-7.43 (m. 2H); 7.64-7.93 (m. 7H); 8.35-8.38 (m. 1H); 8.51-8.52 (m. 1H); 12.67 (s. 1H).

Example 13

Preparation of 7-[(E)-2-(6,7-difluoroquinolin-2-yl)vinyl]-5-{[2-(1H-tetrazol-5-yl)ethyl]thio}5,11-dihydro[1]benzoxepino[3,4-b]pyridine Step 1: S-(2-cyano-ethyl) ethanethioate

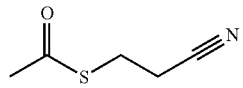

A mixture of 3.13 ml (3.33 g; 43.79 mmol) of ethanethioic S-acid and 2.9 ml (3.59 g; 67.81 mmol) of acrylonitrile is cooled in an ice bath. 0.20 ml (0.27 g; 2.72 mmol) of N,N,N-triethylamine are dropped with stirring (exothermic). The system is stirred at room temperature for 16 hr and is partitioned between ethyl ether/pentane 1:1 and water. The organic layer is washed with water, is dried and concentrated giving 4.73 g (93%) of a crude product, which is used without purification in the next step.

Step 2: S-[2-(2H-tetrazol-5-yl)-ethyl]ethanethioate

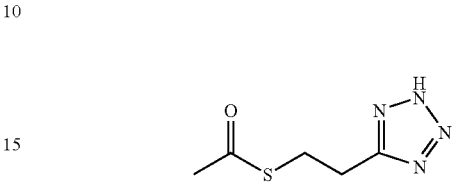

1.55 g (9.00 mmol) of the previous compound and 6 g (18.0 mmol) of azidotributyltin are stirred at 110° C. for 3 hr. The residue is partitioned between pentane and 4% NaHCO$_3$. The aqueous layer is washed with pentane, acidified with 6N HCl and saturated with NaCl. The product is extracted with ethyl acetate, which is washed with water, dried and concentrated. The yield of crude product is 0.64 g (31%).

Step 3: 2-(2H-tetrazol-5-yl)-ethanethiol

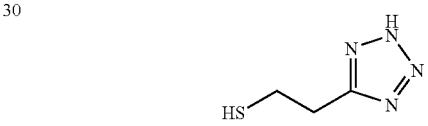

A mixture of 0.56 g (4.30 mmol) of the compound from the previous step, 28 ml of methanol and 2.8 ml of HCl saturated methanol is refluxed for 5 hr in nitrogen atmosphere. The solution is concentrated and the residue used in the next step without further purification (it contains a small amount of the corresponding dithiano derivative).

Step 4: 7-[(E)-2-(6,7-difluoroquinolin-2-yl)vinyl]-5-{[2-(1H-tetrazol-5-yl)ethyl]thio}-5,11-dihydro[1]benzoxepino[3,4-b]pyridine

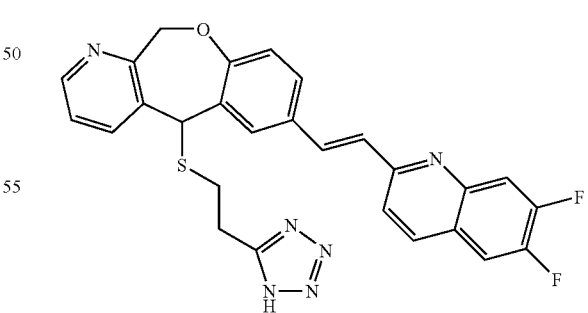

A mixture of 0.26 g (0.64 mmol) of the compound from the Example 10, step 5 and 0.17 g (1.30 mmol) of the compound from the previous step in 2.23 ml of trifluoroacetic acid is stirred at room temperature overnight. The solution is concentrated and the residue is partitioned between ethyl acetate and 4% solution of NaHCO$_3$. After washing the organic layer with water it is dried and concentrated. The residue is flash chromatographied on. SiO$_2$ eluting with dichloromethane/methanol/aq. ammonia 40:8:1. The yield is 0.065 g (20%).

$^1$HNMR (d$^6$-DMSO): 2.70-2.75 (m. 2H); 3.08-3.14 (m. 2H); 4.94-6.00 (AB syst. 2H); 5.18 (s. 1H); 6.83-6.99 (m. 2H); 7.22-8.15 (m. 9H); 8.34-8.50 (m. 1H).

Example 14

Preparation of 1,1,1-trifluoro-N-[2-([7-[(E)-2-(6,7-difluoroquinolin-2-yl)vinyl]-5,11-dihydro[1]benzoxepino[3,4-b]pyrindin-5-yl)thio)ethyl]methanesulfonamide Step 1: [2-({7-[(E)-2-(6,7-difluoroquinolin-2-yl)vinyl]-5,11-dihydro[1]benzoxepino[3,4-b]pyrindin-5-yl)thio)ethanamine

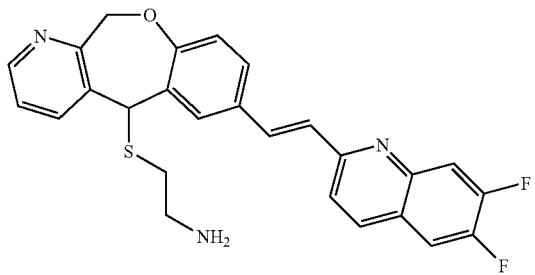

A mixture of 0.20 g (0.49 mmol) of the compound from the Example 10, step 5 and 0.113 g (1.0 mmol) of 2-aminoethanethiol hydrochloride in 1.72 ml of trifluoroacetic acid is stirred overnight at room temperature. The solution is concentrated, 2N NaOH is added to basic pH and the product is extracted with ethyl ether. The organic layer is washed with water, dried and concentrated, giving 0.23 g of residue, which are used per se in the next step.

Step 2: 1,1,1-trifluoro-N-[2-({7-[(E)-2-(6,7-difluoroquinolin-2-yl)vinyl]-5,11-dihydro[1]benzoxepino[3,4-b]pyrindin-5-yl)thio)ethyl]methanesulfonamide

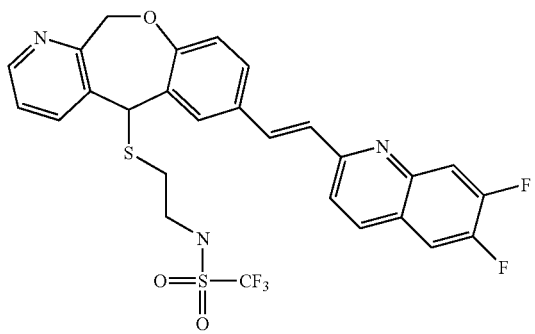

0.13 g (0.28 mmol) of the product from the previous step are dissolved in 25 ml of dichloromethane. The solution is cooled in an ice bath and 0.080 ml (0.057 g; 0.57 mmol) of N,N,N-triethylamine and 0.046 ml-(0.077 g; 0.28 mmol) of trifluoromethanesulfonic anhydride are added. After 1 hr at the ice bath and 1 hr at room temperature, the solution is washed with water, dried and concentrated. The residue is flash chromatographied through SiO$_2$ eluting with chloroform/methanol 97:3. The yield is 0.048 g (28%).

$^1$HNMR (Cl3CD): 2.60 (t. 2H); 3.18 (t. 2H); 4.73 (s. 1H); 4.95-5.93 (AB syst. 2H); 6.76-6.96 (m. 2H); 7.13-7.32 (m. 4H); 7.46.7.90 (m. 4H); 8.07 (s. 1H); 8.51-8.52 (m. 1H).

Example 15

Preparation of 1,1,1-trifluoro-N-[2-({7-[(6,7-difluoroquinolin-2-yl)methoxy]-5,11-dihydro[1]benzoxepino[3,4-b]pyrindin-5-yl)thio)ethyl]methanesulfonamide Step 1: 2-({7-[(6,7-difluoroquinolin-2-yl)methoxy]-5,11-dihydro[1]benzoxepino[3,4-b]pyrindin-5-yl)thio)ethanamine

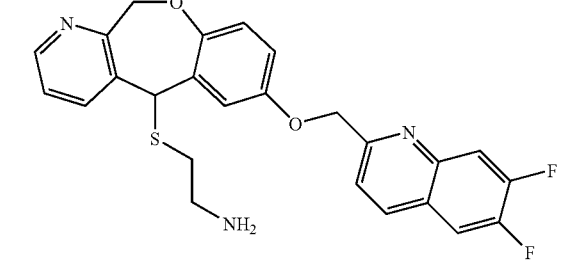

Starting from the product of Example 1, step 6, and using the method of Example 14, step 1, the title compound is prepared in 76% yield.

Step-2: 1,1,1-trifluoro-N-[2-({7-[(6,7-difluoroquinolin-2-yl)methoxy]-5,11-dihydro[1]benzoxepino[3,4-b]pyrindin-5-yl)thio)ethyl]methanesulfonamide

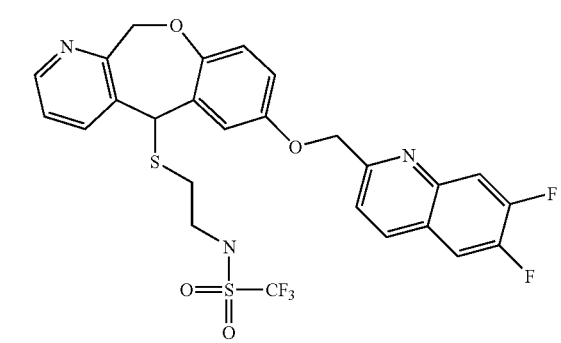

Starting from the product from the previous step 6 and using the method of Example 14, step 2, the title compound is prepared in 61% yield.

$^1$HNMR (Cl3CD): 2.56-2.71 (m. 2H); 3.13-3.32 (m. 2H); 4.78 (s. 1H); 4.94-5.63 (AB syst. 2H); 5.29 (s. 2H); 6.87-6.93 (m. 2H); 7.03-7.06 (m. 1H); 7.14-7.19 (m. 1H); 7.27 (b.s. 1H); 7.51-7.64 (m. 3H); 7.76-7.83 (m. 1H); 8.10-8.13 (m. 1H); 8.41-8.43 (m. 1H)

Example 16

Preparation of 3-{(9-[(E)-2-(6,7-difluoroquinolin-2-yl)vinyl]-5,11-dihydro[1]benzoxepino[4,3-b]pyridin-11-yl)thio}propanoic Acid Step 1: 3-[(4-bromophenoxy)methyl]-pyridine

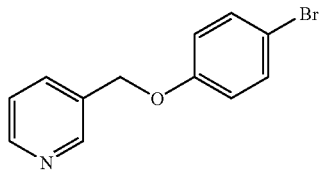

A mixture of 12.75 g (77.73 mmol) of 3-chloromethyl) pyridine hydrochloride, 13.45 g (77.73 mmol) of 4-bromophenol and 27.6 g (200 mmol) of potassium carbonate in 100 ml of methyl ethyl ketone is stirred at room temperature for 24 hr and at 60° C. for 4 hr. The solids are filtered and the filtrate is concentrated. The residue is partitioned between water and diethyl ether. The ethereal layer is washed with 2N NaOH and water, and is dried and concentrated. The resulting oil (12.9 g, 49% yield) solidifies on cooling.

Step 2: 3-[(4-bromophenoxy)methyl]pyridine 1-oxide

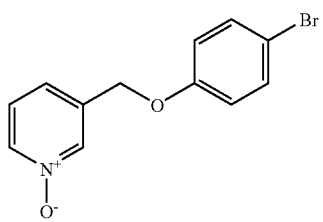

12.02 g (45.50 mmol) of the compound from the previous step is dissolved in 40 ml dichloromethane. A solution of 11.15 g (49.7 mmol) of 77% 3-chlorobenzene carboperoxoic acid in 100 ml dichloromethane is dropped and the whole is stirred overnight. The solvent is eliminated in vacuo and the residue is solved in 2N NaOH and a little diethyl ether. The aqueous layer is then extracted with dichloromethane, which is dried and concentrated, yielding 12.1 g of a solid (95% yield).

Step 3: 3-[(4-bromophenoxy)methyl]pyridine-2-carbonitrile

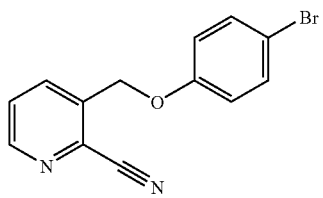

12.1 g (43.2 mmol) of the compound from the previous step is suspended in 50 ml of toluene. Under inert atmosphere, there are added 6.9 ml (5.13 g; 51.8 mmol) of trimethylsilyl cyanide and 3.98 ml (4.64 g; 43.2 mmol) of dimethylcarbamyl chloride and the system is stirred at 60° C. for 20 hr. diethyl ether is added and the solution is washed with 1N $K_2CO_3$ and water. The organic layer is dried and concentrated giving an oil which is crystallised with ethanol. Yield 10.1 g (81%).

Step 4: 9-bromo[1]benzoxepino[4,3-b]pyridin-11(5H)-one

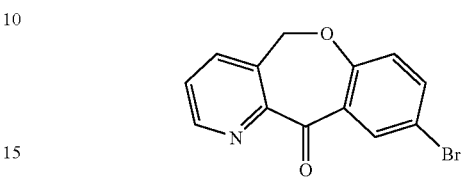

5.0 g (17.3 mmol) of the compound from the previous step are dissolved in 25 ml of trifluoromethanesulfonic acid and stirred at room temperature overnight. The mixture is carefully poured into ice/water and an excess of concentrated hydrochloric acid is added. The solid is filtered, washed with water and suspended in 1N NaOH. After stirring for 1 hr at room temperature, the solid is filtered and washed with water. The yield of the title compound is 3.9 g (77%).

Step 5: 9-bromo-5,11-dihydro[1]benzoxepino[4,3-b]pyridin-11-ol

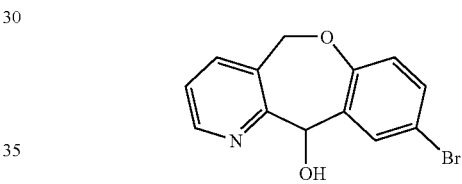

3.9 g (13.4 mmol) of the product from the previous step is dissolved in 78 ml THF and 39 ml methanol. The system is cooled in an ice bath and 0.62 g (16.3 mmol) of sodium borohydride are added in small portions. After stirring at room temperature for 2 hr, the solvents are eliminated in vacuo and the residue is partitioned between diethyl ether and water. The ethereal layer is washed with water, dried and concentrated. 2.9 g (73% yield) of the title compound are thus obtained.

Step 6: 9-[(E)-2-(6,7-difluoroquinolin-2yl)vinyl]-5,11-dihydro[1]benzoxepino[4,3-b]pyridin-11-ol

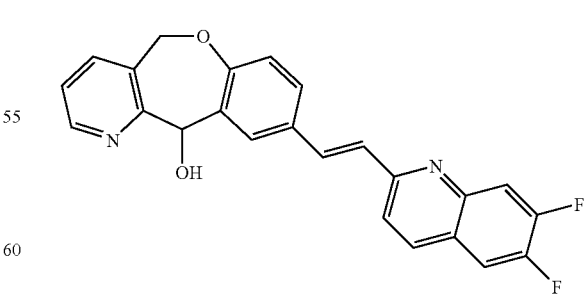

A mixture of 0.37 g (1.26 mmol) of the product from the previous step, 0.27 g (1.41 mmol) of the compound of Example 10, step 4, 0.0085 g (0.037 mmol) of palladium (II) acetate and 0.0362 g (0.12 mmol) of actually tri(o-tolyl)

phosphine in 2.5 ml of dimethylformamide is stirred in an inert atmosphere. With external ice cooling, a solution of 0.27 ml (0.19 g; 1.9 mmol) of N,N,N-triethylamine in 1.2 ml dimethylformamide is dropped. The whole is stirred in a bath at 100° C. for 1 hr. Once at room temperature, 4 ml of water are added. The precipitate is filtered and washed with water and dried. The yield of title product is 0.5 g (98%).

Step 7: 3-{(9-[(E)-2-(6,7-difluoroquinolin-2-yl)vinyl]-5,11-dihydro[1]benzoxepino[4,3-b]pyridin-11-yl)thio}propanoic Acid

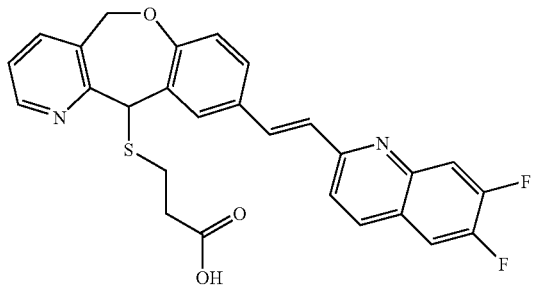

0.3 g (0.74 mmol) of the compound from the previous step are dissolved in 3 ml of trifluoroacetic acid. 0.066 ml (0.080 g; 0.75 mmol) of 3-mercaptopropanoic acid are added and the system is refluxed in an inert atmosphere for 16 hr. The solvent is eliminated in vacuo and the residue chromatographied on SiO2 eluting with ethyl acetate/hexane/acetic acid 20:10:0.2. The yield of title product is 0.085 g (23%).

$^1$HNMR (d$^6$-DMSO): 2.64-2.76 (m. 4H); 5.10-6.01 (AB syst. 2H); 5.40 (s. 1H); 6.92 (d. 1H); 7.37-7.45 (m. 2H); 7.59-7.61 (d. 1H); 7.76.7.99 (m. 6H); 8.34-8.37 (m. 1H); 8.49-8.50 (m. 1H).

Example 17

Preparation of 3-{(9-[(6,7-difluoroquinolin-2-yl)methoxy]-5,11-dihydro[1]benzoxepino[4,3-b]pyridin-11-yl)thio}propanoic Acid Step 1: furo[3,4-b]pyridin-7(5H)-one

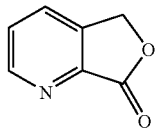

This compound is prepared according to J. Med. Chem. 1995, 38, 496-507.

Step 2: 3-[(4-methoxyphenoxy)methyl]pyridine-2-carboxylic Acid

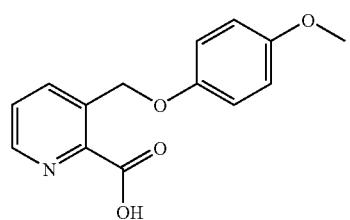

14.77 g (119 mmol) of 4-methoxyphenol are suspended in 50 ml of methanol. 22.6 ml (119 mmol) of a 30% solution of sodium methoxide in methanol are added. The solution is concentrated to dryness and 24.1 g (178 mmol) of the lactone from the previous step, 12 g of sodium chloride and 300 ml of xylene (mixture of isomers, solvent grade) are added. The whole is refluxed for 2 hr. Once at room temperature, the solid is filtered, washed with ethyl ether and dissolved in 0.2 N NaOH. The solid is filtered and the filtrate made slightly acidic (pH 5) with 2N HCl. The solid is filtered, water washed and dried. The yield is 24.1 g (52%).

Step 3: 3-[(4-methoxyphenoxy)methyl]pyridine-2-carboxamide

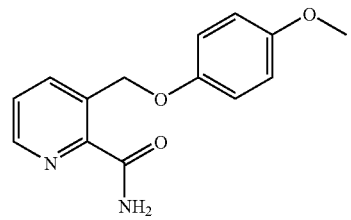

2.0 g (7.7 mmol) of the compound from the previous step is dissolved in 50 ml of dichloromethane. 1.26 g (7.7 mmol) of 1,1'-carbonylbis-1H-imidazole are added and the system stirred at room temperature for 30'. 35 ml of NH3 in ethanol saturated solution are dropped and the stirring continued overnight. The solvent is evaporated, water added to the residue and the solid filtered, washed with water and dried. The yield of the title product is 1.5 g (75%).

Step 4: 3-[(4-methoxyphenoxy)methyl]pyridine-2-carbonitrile

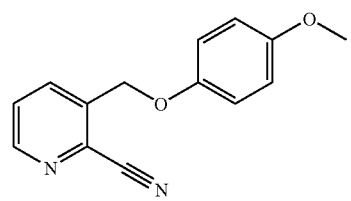

0.6 g (2.3 mmol) of the product from the previous step is dissolved in 25 ml of dichloromethane. 0.4 ml (0.29 g; 2.8 mmol) of N,N,N-triethylamine and 0.4 ml (0.59 g; 5.2 mmol) of trifluoroacetic acid are added, and the system is stirred at room temperature for 1 hr. The solution is washed with water, diluted NaHCO₃, more water and is dried and concentrated. The residue is crystallised from diethyl ether/diisopropyl ether. The yield of the title compound is 0.56 g (100%).

Step 5: 9-methoxy[1]benzoxepino[4,3-b]pyridin-11(5H)-one

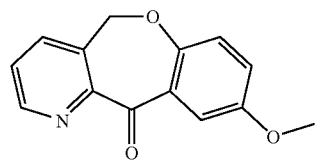

0.55 g (2.2 mmol) of the previous compound is dissolved in 4 ml of trifluoromethane-sulfonic acid and stirred at room temperature overnight. The solution is poured into excess ice and the system is made alkaline with 8N NaOH. The product is extracted with diethyl ether, which is dried and concentrated. The residue is taken in diisopropyl ether and filtered. The yield is 0.4 g (72%).

Step 6:
9-hydroxy[1]benzoxepino[4,3-b]pyridin-11(5H)-one

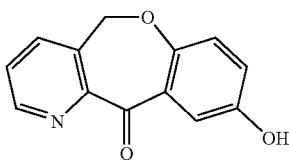

0.9 g (3.7 mmol) of the compound from the previous step is suspended in 18 ml of 48% aqueous hypobromic acid and the system is stirred at 125° C. for 3.5 hr. The system is made alkaline with 8N NaOH, the solid filtered and the filtrate is made acid with acetic acid. The yellow solid is filtered, washed with water and dried. The yield is 0.8 g (94%).

Step 7: 9-[(6,7-difluoroquinolin-2-yl)methoxy][1]benzoxepino[4,3-b]pyridin-11(5H)-one

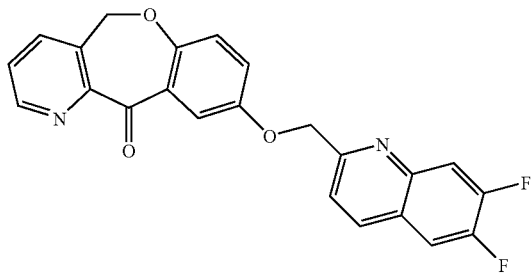

Starting from the previous compound and the compound from Example 1, step 4, and according to the method of Example 1, step 5, the title compound is prepared in 98% yield.

Step 8: 9-[(6,7-difluoroquinolin-2-yl)methoxy]-5,11-dihydro[1]benzoxepino[4,3-b]pyridin-11-ol

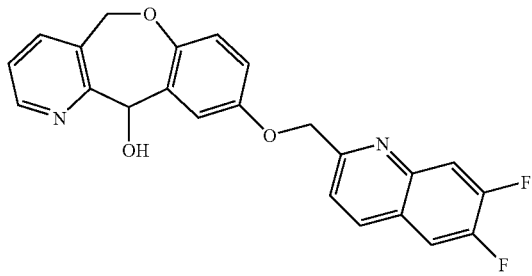

Starting from the previous compound, and according to the method of Example 1, step 6, the title compound is prepared in 85% yield.

$^1$HNMR (d$^6$-DMSO): 5.12-5.63 (AB syst. 2H); 5.28 (s. 2H); 5.78 (s. H); 6.11 (b.s. 1H); 6.79-6.98 (m. 2H); 7.12-7.19 (m. 1H); 7.31-7.42 (m. 1H); 7.63-7.83 (m. 2H); 8.00-8.18 (d. 2H); 8.39-8.42 (d. 2H).

Step 9: 3-{(9-[(6,7-difluoroquinolin-2-yl)methoxy]-5,11-dihydro[1]benzoxepino[4,3-b]pyrindin-11-yl)thio}propanoic Acid

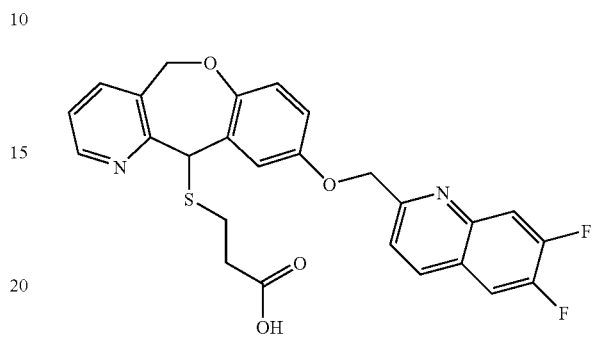

0.3 g (0.73 mmol) of the compound from the previous step are dissolved in 3 ml of trifluoroacetic acid. 0.15 ml (0.18 g; 1.72 mmol) of 3-mercaptopropanoic acid are added and the whole is stirred at 45° C. for 5 hr. The solution is concentrated and the residue partitioned between dichloromethane and water. The organic layer is washed with water, 4% NaHCO3, 1% citric acid solution, more water, and is dried and concentrated. The title compound crystallises from dichloromethane. The yield is 0.18 g (49%).

$^1$HNMR (d$^6$-DMSO): 2.63-2.73 (m. 4H); 4.97-5.75 (AB syst. 2H); 5.32 (s. 2H); 5.76 (s. 1H); 6.82-6.95 (m. 2H); 7.20 (s. 1H); 7.36-7.40 (m. 1H); 7.72-7.77 (m. 2H); 8.01-8.14 (m. 2H); 8.43-8.46 (m. 2H).

Example 18

Preparation of 1-{[(9-[(6,7-difluoroquinolin-2-yl)methoxy]-5,11-dihydro[1]benzoxepino[4,3-b]pyrindin-11-yl)thio]methyl}cyclopropyl Acetic Acid

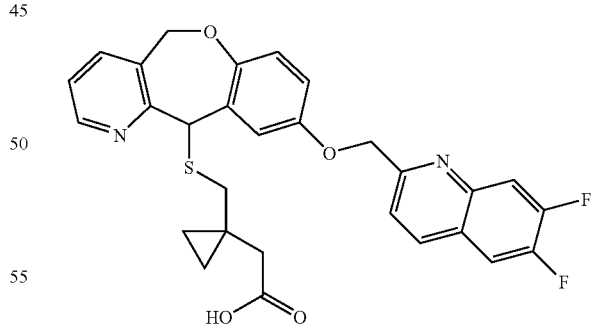

0.25 g (0.61 mmol) of the compound from Example 17 step 8 are dissolved in 2.5 ml of trifluoroacetic acid. 0.18 g (1.23 mmol) of the product from Example 7, step 1 are added and the whole is stirred at 45° C. for 36 hr. The solution is concentrated and the residue partitioned between dichloromethane and water. The organic layer is washed with water, 4% NaHCO$_3$, 1% citric acid solution, more water, and is dried and concentrated. The title compound crystallises from dichloromethane/diethyl ether. The yield is 0.17 g (52%).

¹HNMR (d⁶-DMSO): 0.24-0.56 (m. 4H); 2.10-2.32 (AB syst. 2H); 2.62 (s. 2H); 4.95-5.78 (AB syst. 2H); 5.17 (s. 1H); 5.31 (s. 2H); 6.81-6.84 (m. 1H); 6.91-6.94 (m. 1H); 7.06-7.07 (m. 1H); 7.69-7.76 (m. 2H); 8.00-8.13 (m. 2H); 8.40-8.44 (m. 2H); 12.02 (s. 1H);

Example 19

Preparation of 7-[(6,7-difluoroquinolin-2-yl)methoxy]-5-{[2-(1H-tetrazol-5-yl)methyl]thio}-5,11-dihydro[1]benzoxepino[3,4-b]pyridine Step 1: ({7-[(6,7-difluoroquinolin-2-yl)methoxy]-5,11-dihydro[1]benzoxepino[3,4-b]pyridin-5-yl}thio)acetonitrile

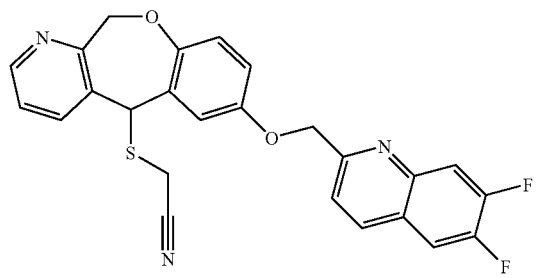

A mixture of 0.3 g (0.74 mmol) of the product from Example 1, step 6 and 0.3 g (0.74 mmol) of Lawesson's reagent (2,4-bis(4-methoxyphenyl)-1,3,2,4-dithiadiphosphetane 2,4-disulfide) in 30 ml of toluene is refluxed for 15'. The solution is washed with water, dried and concentrated. The residue is dissolved in 25 ml of dichloromethane and 0.07 g (0.93 mmol) of chloroacetonitrile and 0.14 ml (0.10 g; 1.0 mmol) of N,N,N-triethylamine are added. The whole is stirred overnight at room temperature. The solution is washed with water, dried, concentrated and chromatographied trough SiO₂ eluting with dichloromethane/methanol 98:2. The yield of title product is 0.12 g (35%).

Step 2: 7-[(6,7-difluoroquinolin-2-yl)methoxy]-5-{[2-(1H-tetrazol-5-yl)methyl]thio}-5,11-dihydro[1]benzoxepino[3,4-b]pyridine

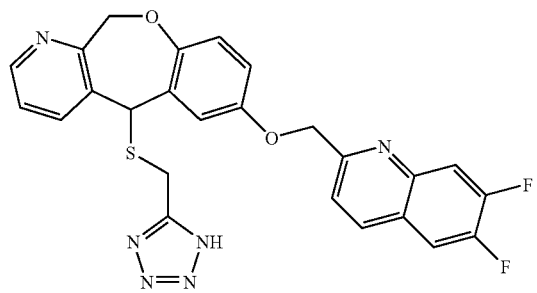

0.12 g (0.26 g) of the previous compound and 0.17 g (0.5 mmol) of azidotributyltin are heated to 110° C. for 2 hr. The residue is chromatographied through SiO2 eluting with dichloromethane/methanol/aq. ammonia 40:8:1. The yield is 0.08 g (60%).

¹HNMR (Cl3CD): 3.90 (s. 2H); 4.85 (s. 1H); 4.98-5.64 (AB syst. 2H); 5.30 (s. 2H); 6.90-6.87 (m. 2H); 6.99-7.02 (m. 1H); 7.14-7.18 (m. 1H); 7.53-7.66 (m. 3H); 7.79-7.85 (m. 1H); 8.14-8.17 (d. 1H); 8.44-8.47 (m. 1H).

Example 20

Preparation of 7-[(6,7-difluoroquinolin-2-yl)methoxy]-5-{[2-(1H-tetrazol-5-yl)ethyl]thio}-5,11-dihydro[1]benzoxepino[3,4-b]pyridine

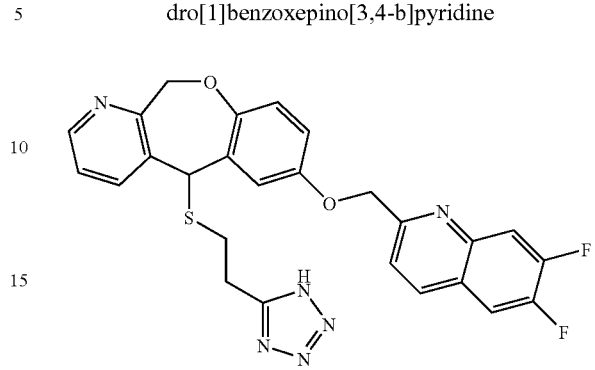

This compound is prepared according to the method of the Example 19, replacing the chloroacetonitrile for the 3-chloropropanenitrile with yields of 30% and 70%, respectively.

¹HNMR (Cl3CD): 2.65-3.12 (m. 2H); 2.81-2.85 (m. 2H); 4.71 (s. 1H); 5.03-5.69 (AB syst. 2H); 5.33 (s. 2H); 6.80-6.81 (m. 1H); 6.87-6.91 (m. 1H); 7.03-7.06 (m. 1H); 7.15-7.19 (m. H); 7.55-7.65 (m. 3H); 7.80-7.86 (s. 1H); 8.14-8.17 (s. 1H); 8.45-8.46 (s. 1H).

Example 21

Preparation of 3-[7-(6,7-Difluoro-quinolin-2-yl-methoxy)-11-methyl-10,11-dihydro-5H-benzo[e]pyrido[2,3-b]azepin-5-ylsulfanyl]-propionic Acid Step 1: 11-Methyl-10,11-dihydro-benzo[e]pyrido[2,3-b]azepin-5-one

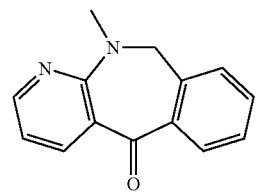

This compound is prepared according to DD 80449.

Step 2: 11-Methyl-7-nitro-10,11-dihydro-benzo[e]pyrido[2,3-b]azepin-5-one

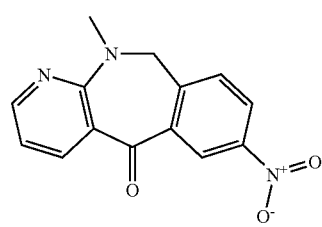

1.0 g (4.46 mmol) of the product from step 1 is dissolved in 35 ml of concentrated sulphuric acid. While keeping the system at a temperature between −5 and −10° C., 0.45 g (4.28 mmol) of potassium nitrate is added in portions with stirring. The whole is stirred at this temperature for an additional hour and is kept at the freezer for 48 hr. The solution is poured into ice, basified with aqueous ammonia and extracted with dichloromethane. The organic layer is dried and concentrated. The residue is chromatographied on silica eluting with hexane/ethyl acetate 7:3. Yield: 0.36 g (32%).

Step 2: 7-Amino-11-methyl-10,11-dihydro-benzo[e]pyrido[2,3-b]azepin-5-one

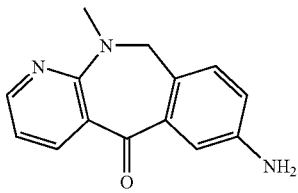

0.26 g (0.96 mmol) of the previous compound are dissolved in 5.2 ml of acetic acid and the solution is heated to 90° C. 0.78 g (3.45 mmol) of tin (II) chloride dihydrate are added in portions. Once added, the solution is stirred for an additional 10-15', poured into ice, basified with NaOH 2N and extracted with dichloromethane. The extracts are dried and concentrated, yielding 0.21 g of product (91%), pure enough to continue.

Step 3: 7-Hydroxy-11-methyl-10,11-dihydro-benzo[e]pyrido[2,3-b]azepin-5-one

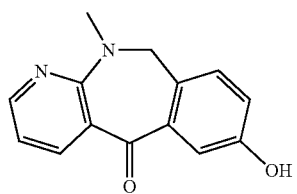

0.082 g (1.12 mmol) of sodium nitrite are added during 10' to 0.8 ml of sulphuric acid. The whole is then heated to 70° C. until having a clear solution. The temperature is then kept between 25 and 35° C. while a solution of 0.26 g (1.08 mmol) of the amine from the previous step in 2.3 ml of acetic acid is slowly added. Once finished the addition the whole is stirred for 10' and this solution is dropped into 22 ml of 10% sulphuric acid at reflux temperature, with good stirring. After 15' of reflux the solution is concentrated, the residue basified with 2N NaOH and acidified with acetic acid to pH 5. The product is extracted with ethyl acetate, washed with water, dried and concentrated. The yield of pure phenol is 0.24 g (92%).

Step 4: 7-(6,7-Difluoro-quinolin-2-ylmethoxy)-11-methyl-10,11-dihydro-benzo-[e]pyrido[2,3-b]azepin-5-one

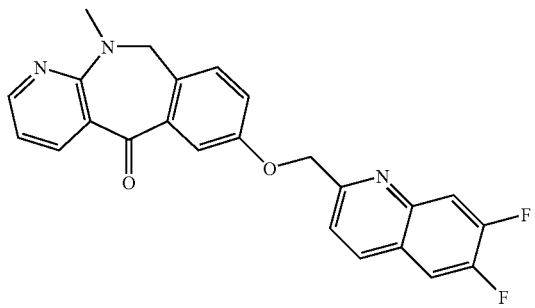

0.24 g (1.0 mmol) of the phenol from the previous step are dissolved in 5 ml of dry DMF and 0.0376 g (1.0 mmol) of 60% sodium hydride in mineral oil are added. After stirring at room temperature for 20', 0.267 g (1.0 mmol) of the product from Example 1, step 4 are added and the system is stirred for 16 hr at room temperature. The solvent is eliminated and the residue is partitioned between dichloromethane and water. The organic layer is washed with water, dried and concentrated. Yield: 0.40 g (96%).

Step 5: 7-(6,7-Difluoro-quinolin-2-ylmethoxy)-11-methyl-10,11-dihydro-5H-benzo[e]pyrido[2,3-b]azepin-5-ol

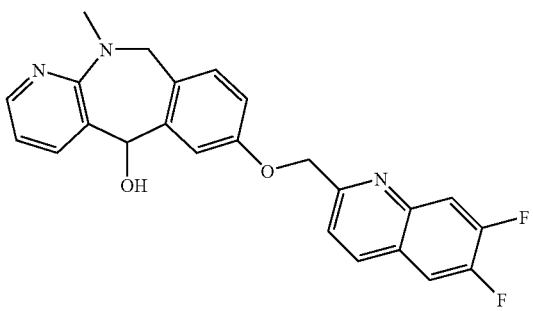

0.4 g (0.95 mmol) of the ketone from the previous step are dissolved in 7 ml of THF and 2.3 ml of methanol are added. The solution is cooled in an ice bath while 0.043 g (1.1 mmol) of sodium borohydride are added in portions with stirring. After 1 hr stirring at room temperature the solvents are eliminated and the residue stirred with water for 30'. The residue is filtered, washed with water and dried. Yield: 0.28 g (75%).

Step 6: 3-[7-(6,7-Difluoro-quinolin-2-ylmethoxy)-11-methyl-10,11-dihydro-5H-benzo[e]pyrido[2,3-b]azepin-5-ylsulfanyl]-propionic Acid

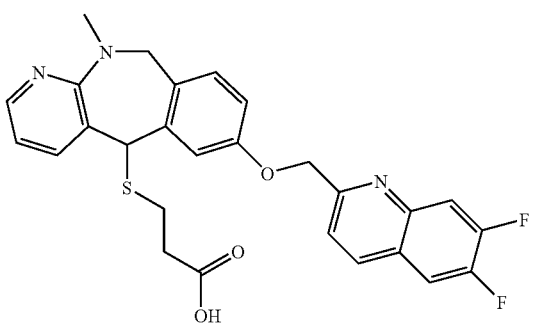

0.17 g (0.40 mmol) of the alcohol from the previous step are suspended in 5 ml of dichloromethane. 3.5 ml of trifluoroacetic acid and 0.0882 μg (0.83 mmol) of 3-mercaptopropionic acid are added and the system is stirred at 45° C. for 16 hr. The solvents are eliminated and the residue is partitioned between dichloromethane and water. The organic layer is washed with water, dried and concentrated. The residue is chromatographied on SiO2 eluting with ethyl acetate/hexane 6:4 yielding 0.074 g of the product (36%).

[1]HRMN (d$^6$-DMSO): 2.37-2.63 (m. 6H); 3.14 (s. 3H); 4.03-5.59 (AB syst. 4H); 5.13 (s. 1H); 5.36 (s. 2H); 6.54-6.58

(m. 1H); 6.96-6.99 (m. 1H); 7.08-7.09 (m. 1H); 7.29-7.31 (m. 1H); 7.42-7.45 (m. 1H); 7.67-7.69 (d. 1H); 7.98-8.12 (m. 3H); 8.40-8.43 (d. 1H); 12.24 (b.s. 1H).

Example 22

Preparation of 3-[7-(7-Chloro-6-fluoro-quinolin-2-ylmethoxy)-11-methyl-10,11-dihydro-5H-benzo[e]pyrido[2,3-b]azepin-5-ylsulfanyl]-propionic Acid

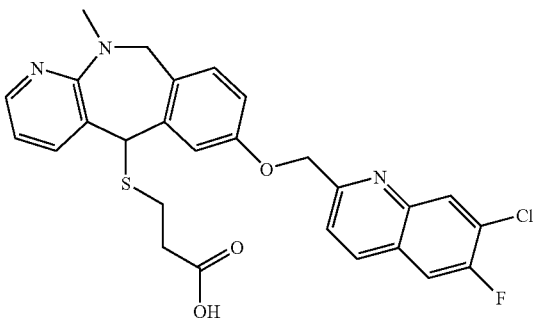

Starting from the product of Example 21 step 3, substituting the alkylating agent for the corresponding to that of Example 3, step 2, and operating subsequently as in the previous example, the title product is obtained in similar yields to that described previously.

[1]HRMN (Cl3CD): 2.68-2.73 (m. 6H); 3.22 (s. 3H); 3.82-5.75 (AB syst. 2H); 4.90 (s. 1H); 5.35 (s. 2H); 6.50-6.54 (m. 1H); 6.85-6.86 (m. 1H); 6.89-6.92 (m. 1H); 7.14-7.16 (d. 1H); 7.37-7.40 (m. 1H); 7.51-7.54 (d. 1H); 7.65-7.68 (d. 1H); 8.04-8.06 (m. 1H); 8.06-8.11 (d. 1H); 8.19-8.21 (d. 1H).

Example 23

Preparation of 3-[7-(7-Chloro-6-fluoro-quinolin-2-ylmethoxy)-10,11-dihydro-5H-benzo[4,5]cyclohepta[1,2-b]pyridin-5-ylsulfanyl]-propionic Acid Step 1: 2-Methyl-nicotinic Acid Ethyl Ester

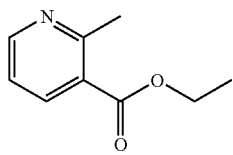

This compound was prepared according to Arzneim. Forsch. 1968, 18, 756.

Step 2: 2-[2-(4-Methoxy-phenyl)-vinyl]-nicotinic Acid

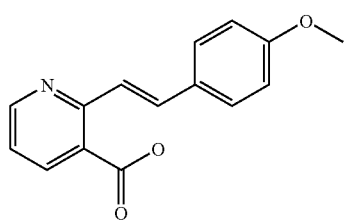

A mixture of 5.0 g (30.26 mmol) of the previous compound and 7.74 g (56.8 mmol) of anisaldehyde is heated at 120° C. 3.9 g (28.6 mmol) of anhydrous zinc chloride are added and the whole is heated at 180° C. allowing the ethanol formed to be expelled. After 2 hr a solid crystallises and a solution of 4.9 g of sodium hydroxide in 41 ml of water is added. After stirring to disgregation, the inorganic salts are filtered and the filtrate is washed with ethyl ether and neutralised with acetic acid. The solid precipitated is filtered, washed with water and recrystallised from ethanol. Yield: 5.2 g (67%).

Step 3: 2-[2-(4-Methoxy-phenyl)-ethyl]-nicotinic Acid

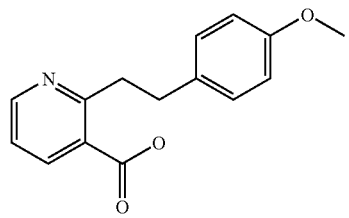

5.2 g (20.2 mmol) of the previous compound are dissolved in a solution of 0.96 g of sodium hydroxide in 30 ml of water. 0.5 g of Raney nickel are added and the whole is hydrogenated at 50 psi during 2 hr. The catalyst is filtered and the residue neutralised with acetic acid. The solid thus precipitated is filtered, washed with water and dried. Yield: 4.3 g (82%).

Step 4: 7-Methoxy-10,11-dihydro-benzo[4,5]cyclohepta[1,2-b]pyridin-5-one

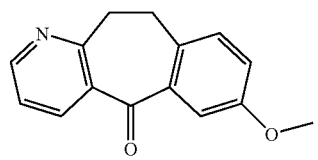

2.4 g (9.3 mmol) of the previous compound are suspended in 36 ml of 1,1,2,2-tetrachloroethane. 3.36 ml (5.0 g; 23.7 mmol) of trifluoroacetic anhydride are added and the whole is stirred at room temperature for 45 minutes. 1.5 ml (1.68 g; 11.8 mmol) of boron trifluoride diethyl etherate are added and the system is stirred at 100° C. for 4 hr. After cooling at room temperature, more trifluoroacetic anhydride (1.7 ml; 12.0 mmol) and boron trifluoride diethyl etherate (1.0 ml; 7.8 mmol) are added and the heating at 100° C. is prosecuted for 16 hr. The solution is poured into excess of 2N NaOH/ice and the organic layer is washed with water, dried and concentrated. The residue is dissolved in 25 ml of diisopropyl ether and the insoluble material is discarded. The solution is concentrated to an oil pure enough for prosecuting the synthesis. Yield: 1.5 g (67%)

Step 5: 7-Hydroxy-10,11 dihydro-benzo[4,5]cyclohepta[1,2-b]pyridin-5-one

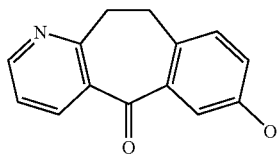

1.5 g (6.2 mmol) of the previous compound are dissolved in 30 ml of 48% aqueous hydrobromic acid and the whole is heated at 125° C. for 3.5 hr. Excess 8N NaOH/ice is added until basic pH and the solid material is filtered and discarded. The filtrate is taken to pH 4-5 with acetic acid and the resulting solid is filtered, water washed and dried. Yield: 1.25 g (88%).

Step 6: 7-(6,7-Difluoro-quinolin-2-ylmethoxy)-10,11-dihydro-benzo[4,5]cyclohepta[1,2-b]pyridin-5-one

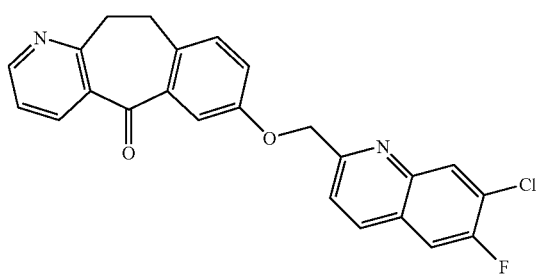

1.25 g (5.5 mmol) of the previous compound are suspended in 20 ml of methanol. 1.05 ml (1.01 g; 5.6 mmol) of a 30% w/v solution of sodium methoxyde are added (whereupon the solid dissolves). The solvent is evaporated and the residue is dissolved in 30 ml DMF. 1.52 g (5.5 mmol) of the product from Example 3, step 2 are added and the whole is stirred at room temperature for 16 hr. The solvent is evaporated and the residue is partitioned between dichloromethane and water. The organic layer is washed with water, dried and concentrated. Ethyl ether is added, crystallizing thus 1.5 g (65%) of the product.

Step 7: 7-(6,7-Difluoro-quinolin-2-ylmethoxy)-10,11-dihydro-5H-benzo[4,5]cyclohepta[1,2-b]pyridin-5-ol

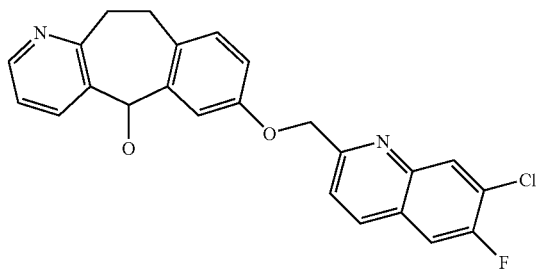

1.5 g (3.5 mmol) of the previous compound are suspended in 30 ml of THF and 10 ml of methanol. With external cooling (ice bath) and stirring, 0.16 g (4.2 mmol) of sodium borohydride are added in portions. After stirring at room temperature for 2 hr, the solvents are evaporated and the residue is suspended in water and stirred at 50° C. for 15'. The solid is filtered, washed with water and dried. Yield: 1.4 g (93%).

Step 8: 3-[7-(7-Chloro-6-fluoro-quinolin-2-ylmethoxy)-10,11-dihydro-5H-benzo[4,5]cyclohepta[1,2-b]pyridin-5-ylsulfanyl]-propionic Acid

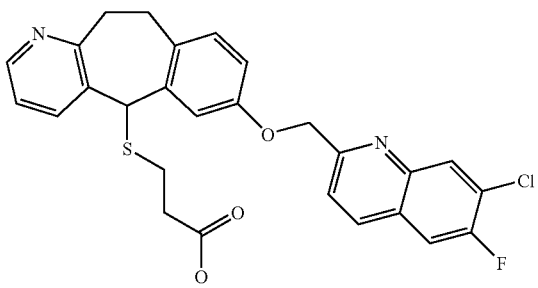

1.4 g (3.3 mmol) of the previous compound is suspended in 25 ml of dichloromethane. 11.45 ml (17.05 g; 149.5 mmol) of trifluoroacetic acid and 0.56 ml (0.68 g; 6.4 mmol) of 3-mercaptopropionic acid are added and the whole stirred at 45° C. for 16 hr. The solution is concentrated and the residue is partitioned between dichloromethane with 5% methanol added and water. The organic layer is washed with 0.5% sodium bicarbonate and water. After drying the solution is concentrated, crystallizing thus the product (1.0 g; 59%).

$^1$HRMN (d$^6$-DMSO): 2.38-2.56 (m. 4H); 2.77-2.98 (m. 2H); 3.51-3.60 (m. 1H); 3.73-3.82 (m. 1H); 5.26 s. (1H); 5.35 (s. 2H); 6.92-6.95 (m. 1H); 7.11-7.23 (m. 3H); 7.68.7.74 (m. 2H); 8.06 (d. 1H); 8.28 (d. 1H); 8.37-8.39 (m. 1H); 8.43 (d. 1H); 12.2 (s., 1H).

Example 24

Preparation of 3-[7-(6,7-difluoro-quinolin-2-ylmethoxy)-10,11-dihydro-5H-benzo[4,5]cyclohepta[1,2-b]pyridin-5-ylsulfanyl]-propionic Acid

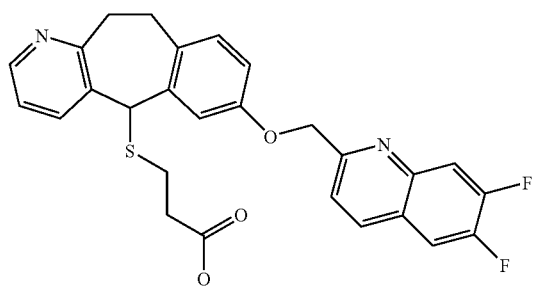

Starting from the product of Example 23, step 5, substituting the alkylating agent for the corresponding to that of Example 1, step 2, and operating subsequently as in the previous example, the title product is obtained in similar yields to that described previously.

$^1$HRMN (d6-DMSO): 2.38-2.56 (m. 4H); 2.78-2.93 (m. 2H); 3.51-3.60 (m. 1H); 3.73-3.81 (m. 1H); 5.25 s. (1H); 5.34 (s. 2H); 6.91-6.95 (m; 1H); 7.10-7.22 (m. 3H); 7.68-7.71 (d. 2H); 8.00-8.12 (m. 2H); 8.37-8.39 (m. 2H); 12.2 (b.s., 1H).

Example 25

Preparation of 3-[7-(6,7-Difluoro-quinolin-2-yl-methoxy)-10,11-dihydro-5H-benzo[4,5]cyclohepta[1,2-c]pyridin-5-ylsulfanyl]-propionic Acid Step 1: 10,11-Dihydro-benzo[4,5]cyclohepta[1,2-c]pyridin-5-one

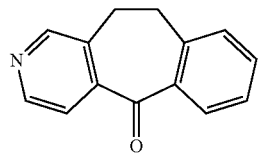

This compound is prepared according to J. Heterocycl. Chem. 1971, 8(1), 73-81.

Step 2: 7-Nitro-10,11-dihydro-benzo[4,5]cyclohepta[1,2-c]pyridin-5-one

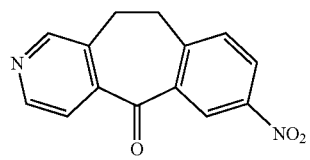

A mixture of 13.0 ml of fuming nitric acid and 2:5 ml of 70% nitric acid is ice cooled. 2.7 g (12.9 mmol) of the previous compound are added in portions, with stirring, during 1 hr. After an additional stirring period of 20', the ice bath is replaced for an oil bath and the mixture stirred at 50° C. for 30'. After cooling, the mixture is poured into excess ice, basified with 2N NaOH and the whole is heated at 80° C. for some minutes. The solid is filtered, water washed, dried and crystallised from acetone. Yield: 1.6 g (49%).

Step 3: 7-Amino-10,11-dihydro-benzo[4,5]cyclohepta[1,2-c]pyridin-5-one

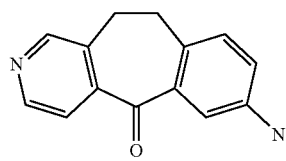

1.6 g (6.29 mmol) of the previous compound are suspended in 14 ml of acetic acid and the whole is heated at 90° C. with stirring. 5.0 g (22.16 mmol) of tin dichloride dihydrate are added in portions and afterwards the stirring is prosecuted for an additional period of 15'. The solution is poured into ice, neutralized with 2N NaOH and extracted with dichloromethane. The organic layer is washed with water, dried and concentrated. Yield: 0.8 g (57%).

Step 4: 7-Hydroxy-10,11-dihydro-benzo[4,5]cyclohepta[1,2-c]pyridin-5-one

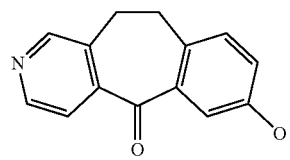

0.27 g (3.9 mmol) of sodium nitrite are added in portions, during 10', into 2.6 ml of concentrated sulphuric acid. The whole is heated at 70° C. until clear solution. Once cooled at room temperature, a solution of 0.8 g (3.5 mmol) of the previous compound in 7.5 ml of acetic acid is dropped into the nitrosating solution very slowly with stirring at a temperature range of 25-35° C. After 15 additional minutes of stirring, the solution is dropped into 71 ml of 10% sulphuric acid at reflux. After 15 additional minutes of refluxing, the solution is concentrated at vacuum, the residue basified with 2N NaOH and neutralised with acetic acid. The product is extracted with ethyl acetate, washed with water, dried and concentrated. Yield: 0.72 g (90%).

Step 5: 7-(6,7-Difluoro-quinolin-2-ylmethoxy)-10,11-dihydro-benzo[4,5]cyclohepta[1,2-c]pyridin-5-one

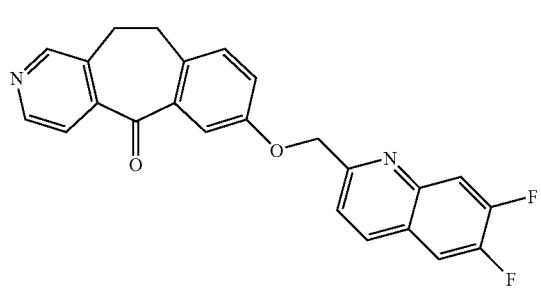

Starting from the previous compound and using the same procedure than in Example 23, step 6 (using as alkylating agent the compound of Example 1, step 4), the corresponding derivative is obtained in 85% yield.

Step 6: 7-(6,7-Difluoro-quinolin-2-ylmethoxy)-10,11-dihydro-5H-benzo[4,5]cyclohepta[1,2-c]pyridin-5-ol

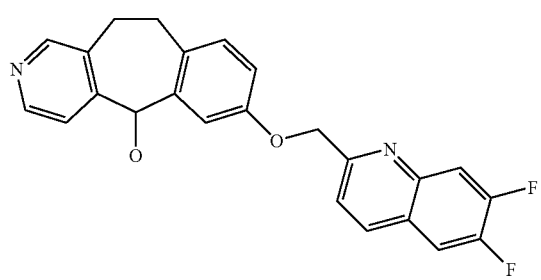

Starting from the previous compound and using the same procedure than in Example 23, step 7, the corresponding derivative is obtained in 69% yield.

Step 7: 3-[7-(6,7-Difluoro-quinolin-2-ylmethoxy)-10,11-dihydro-5H-benzo[4,5]cyclohepta[1,2-c]pyridin-5-ylsulfanyl]-propionic Acid

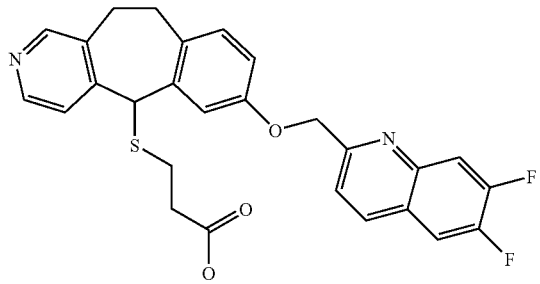

0.48 (1.1 mmol) of the previous compound is suspended in 10 ml dichloromethane. 4.1 ml of trifluoroacetic acid and 0.20 ml (0.24 g; 2.2 mmol) of 3-mercaptopropionic acid are added. The solution is stirred at 45° C. for 72 hr. The solvent is eliminated, the residue partitioned between dichloromethane and water, and the pH of the aqueous layer is made with the aid of sodium bicarbonate. The organic layer is washed with water, dried, concentrated, and the residue chromatographied on SiO2 eluting with dichloromethane/methanol/acetic acid 100:4:0.8. Yield: 0.05 g (8%).

[1]HRMN (d6-DMSO): 2.39-2.58 (m. 4H); 2.78-2.86 (m. 2H); 3.37-3.50 (m. 1H); 3.63-3.72 (m. 1H); 5.24 (s. 1H); 5.34 (s. 2H); 6.91-6.94 (m. 1H); 7.10-7.15 (m. 2H); 7.27 (d. 1H); 7.69 (d. 1H); 8.01-8.13 (m. 2H); 8.32-8.34 (m. 2H); 8:42 (d. 1H); 12.2 (b.s., 1H).

Example 26

Preparation of 3-[7-(7-Chloro-4-fluoro-quinolin-2-ylmethoxy)-10,11-dihydro-5H-benzo[4,5]cyclohepta[1,2-c]pyridin-5-ylsulfanyl]-propionic Acid

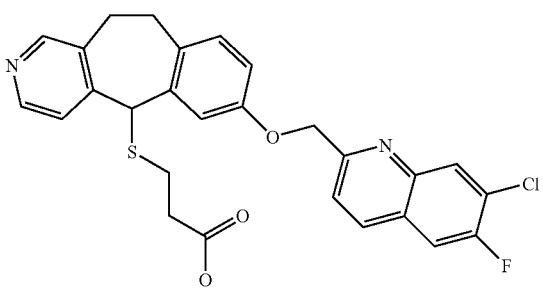

Starting from the product of Example 25, step 4, substituting the alkylating agent for the corresponding to that of Example 3, step 2, and operating subsequently as in the previous example, the title product is obtained in similar yields to that described previously.

[1]HRMN (d6-DMSO): 2.40-2.69 (m. 4H); 2.78-2.85 (m. 2H); 3.37-3.50 (m. 1H); 3.63-3.72 (m. 1H); 5.24 (s. 1H); 5.35 (s. 2H); 6.91-6.95 (m. 1H); 7.10-7.15 (m. 2H); 7.27 (d. 1H); 7.72 (d. 1H); 8.07 (d. 1H); 8.06-8.28 (d. 1H); 8.33-8.34 (m. 2H); 8.43 (d. 1H); 12.2 (b.s., 1H).

Example 27

Preparation of 3-[7-(6,7-Difluoro-quinolin-2-ylmethoxy)-5,11-dihydro-10-oxa-1,3-diaza-dibenzo[a,d]cyclohepten-5-ylsulfanyl]-propionic Acid

Step 1: (2-Acetyl-4-methoxy-phenoxy)-acetic Acid Ethyl Ester

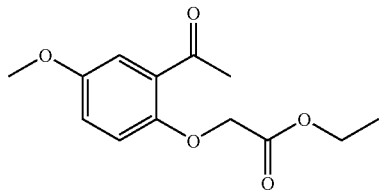

A mixture of 16.6 g (100.0 mmol) of 2-hydroxi-5-methoxyacetophenone, 20 g (208 mmol) of potassium carbonate, 16.7 g (100.0 mmol) of ethyl bromoacetate and 200 ml of MEK is stirred at reflux temperature for 10 hr. The solids are filtered and the filtrate concentrated. The residue is suspended in water and the solid is filtered and dried. Yield: 10.2 g (40%).

Step 2: 7-Methoxy-benzo[b]oxepine-3,5-dione

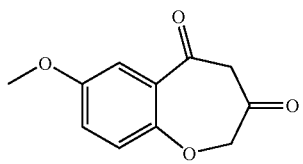

6.0 g (23.7 mmol) of the previous compound is dissolved in 30 ml of DMF, the solution is cooled at −5° C., and 0.95 g (23.7 mmol) of 60% sodium hydride are added in portions. The whole is stirred for 3 hr at room temperature. The solution is poured into excess water, the solid is extracted with toluene and the aqueous layer separated and acidified with 2N HCl. The precipitated crystals are filtered and dried. Yield: 3.5 g (71%).

Step 3: 7-Methoxy-11H-10-oxa-1,3-diaza-dibenzo[a,d]cyclohepten-5-one

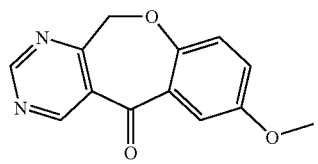

1.49 g (6.78 mmol) of the previous compound and 2.0 ml (1.79 g; 15.5 mmol) of N,N-dimethylformamide dimethyl acetal are stirred at 0° C. for 1 hr. The solvent is eliminated and the residue is washed with a mixture of ethanol and ethyl ether, giving 1.3 g of the intermediate dimethylaminomethylene derivative. A solution of sodium methoxyde is prepared from 0.12 g (5.2 mmol) of sodium and 13.4 ml of methanol. 0.569 (5.3 mmol) of formamidine acetate and the previous intermediate are added. The whole is refluxed for 2 hr and the solvent is eliminated. The residue is partitioned between dichloromethane and water. The organic layer is dried and concentrated. The residue is chromatographied on SiO2 eluting with hexane/ethyl acetate 7:3. Yield: 0.325 mg (25%).

Step 4: 7-Methoxy-11H-10-oxa-1,3-diaza-dibenzo[a,d]cyclohepten-5-one

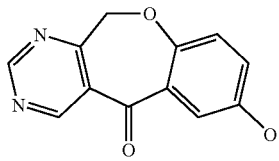

A solution of 0.357 g (1.47 mmol) of the previous compound in 1.5 ml of dichloromethane is dropped into 4 ml (4 mmol) of 1M solution of boron trobromide in dichloromethane. The whole is stirred overnight at room temperature. 4.5 ml of water are added and the system is basified with 8N NaOH. The precipitate is filtered, washed with water and dried. Yield: 0.235 g (70%).

Step 5: 7-(6,7-Difluoro-quinolin-2-ylmethoxy)-11H-10-oxa-1,3-diaza-dibenzo[a,d]cyclohepten-5-one

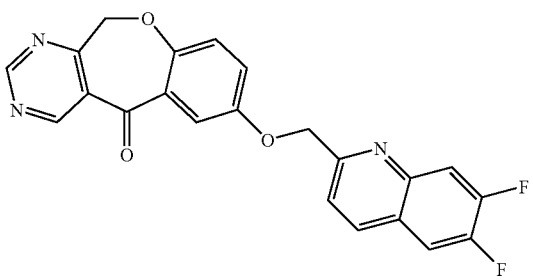

Starting from the previous compound and using the same procedure than in Example 23, step 6, the corresponding derivative is obtained in 91% yield.

Step 6: 7-(6,7-Difluoro-quinolin-2-ylmethoxy)-5,11-dihydro-10-oxa-1,3-diaza-dibenzo[a,d]cyclohepten-5-ol

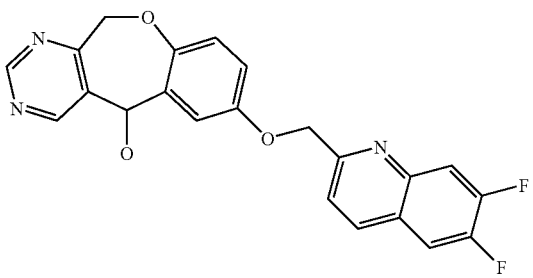

Starting from the previous compound and using the same procedure than in Example 23, step 7, the corresponding derivative is obtained in 81%, yield.

Step 7: 3-[7-(6,7-Difluoro-quinolin-2-ylmethoxy)-5,11-dihydro-10-oxa-1,3-diaza-dibenzo[a,d]cyclohepten-5-ylsulfanyl]-propionic Acid

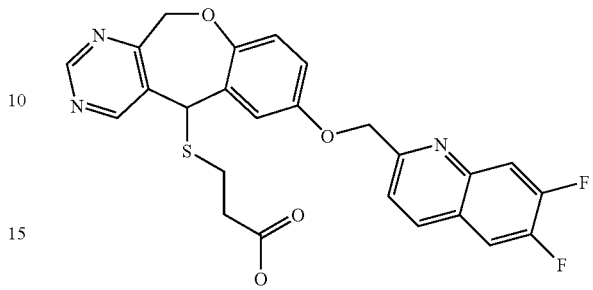

A mixture of 0.306 g (0.75 mmol) of the previous compound, 6 ml of dichloromethane, 2.6 ml of trifluoroacetic acid and 0.13 ml (0.15 g; 1.5 mmol) of 3-mercaptopropionic acid are stirred at 45° C. for 72 hr. The solvent is evaporated, the residue partitioned between dichloromethane and water and sodium bicarbonate is added to pH 5. The organic layer is washed with water, dried and concentrated to little volume, crystallising thus 0.061 g of the title product. Yield: 16%.
$^1$HRMN (d6-DMSO): 2.45 (t. 2H); 2.66 (t. 2H); 4.85-5.42 (AB syst. 2H); 5.18 (s. 1H); 5.34 (s. 2H); 6.98-7.02 (m. 1H); 7.10-7.16 (m. 2H); 7.70 (s. 2H); 8.00-8.13 (m. 2H); 8.43 (d. 2H); 8.79 (s. 1H); 9.02 (s. 1H).

Example 28

Preparation of 3-{7-[2-(6,7-Difluoro-quinolin-2-yl)-ethyl]-5,11-dihydro-10-oxa-4-aza-dibenzo[a,d]cyclohepten-5-ylsulfanyl}-propionic Acid Step 1: 3-Bromomethyl-pyridine-2-carbonitrile

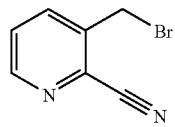

This compound was prepared according to WO 89/10369.

Step 2: 2-[2-(4-Benzyloxy-phenyl)-ethyl]-6,7-difluoro-quinoline

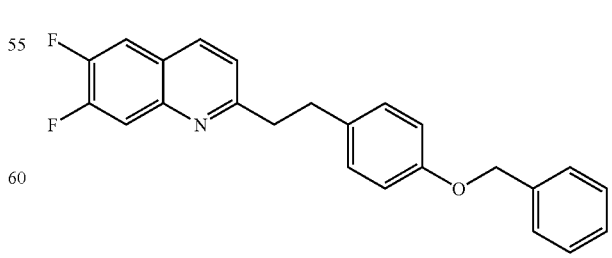

A solution of 8.9 g (49.6 mmol) of the product from Example 1, step 3 in 90 ml THF is cooled at −50° C. 28.6 ml (57.2 mmol) of a 2M solution of lithium diisopropylamide are added and the solution is allowed to heat to −10° C. After 15' stirring at this temperature the deep colored solution is again cooled to −50° C. A solution of 11.6 g (49.8 mmol) of 1-benzyloxy-4-chloromethyl-benzene in 60 ml THF is dropped into the cooled solution. The system is allowed to heat to room temperature and stirred overnight. The solvent is evaporated and the residue that solidifies on cooling is stirred with ethyl ether and filtered. The residue is filtered through SiO2 eluting with dichloromethane. The yield is 3.75 g (20%).

Step 3:
4-[2-(6,7-Difluoro-quinolin-2-yl)-ethyl]-phenol

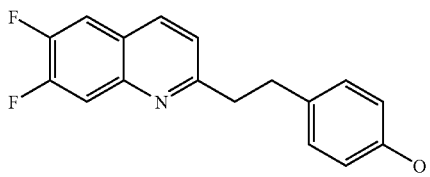

7.1 g (18.9 mmol) of the previous compound are suspended in 250 ml of methanol. Sufficient solution of hydrogen chloride saturated methanol is added drop by drop up to total solution. 0.7 g of 10% palladium on charcoal catalyst are added and the system is hydrogenated at 40 psi during 2 hr. The catalyst is filtered and the solution is concentrated. The residue is partitioned between dichloromethane and a 4 N sodium bicarbonate solution. The organic layer is washed with water, dried and concentrated. Yield: 4.6 g (85%).

Step 4: 2-{4-[2-(6,7-Difluoro-quinolin-2-yl)-ethyl]-phenoxymethyl}-benzonitrile

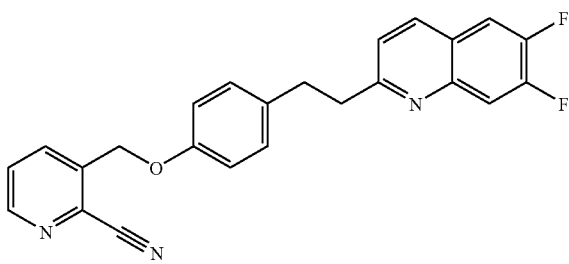

1.0 g (5.0 mmol) of the compound from step 1, 0.077 g (0.5 mmol) of sodium iodide, 1.6 g (5.0 mmol) of caesium carbonate and 1.4 g (3.5 mmol) of the previous compound in 23 ml of acetone are stirred at reflux temperature for 4.5 hr. Once cooled, the solids are filtered and the filtrate is concentrated giving 1.6 g (79%) of a solid.

Step 5: 7-[2-(6,7-Difluoro-quinolin-2-yl)-ethyl]-11H-10-oxa-4-aza-dibenzo[a,d]cyclohepten-5-one

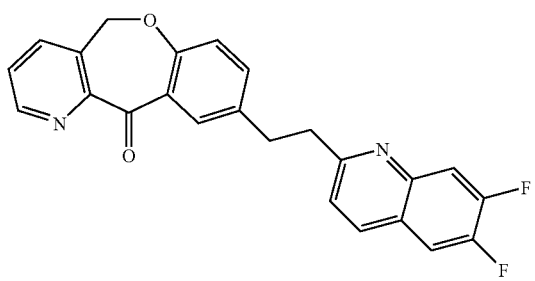

1.0 g (2.5 mmol) of the previous compound and 6.0 ml of trifluoromethansulfonic acid are stirred at room temperature for 3 hr. The solution is poured carefully into excess ice and stirred for 30' at room temperature and 30' at 35° C. The system is basified with 25% NaOH, extracted with dichloromethane, washed with water, dried and concentrated giving a solid which is washed with ethyl acetate and dried. Yield: 0.9 g (88%).

Step 6: 7-[2-(6,7-Difluoro-quinolin-2-yl)-ethyl]-5,11-dihydro-10-oxa-4-aza-dibenzo[a,d]cyclohepten-5-ol

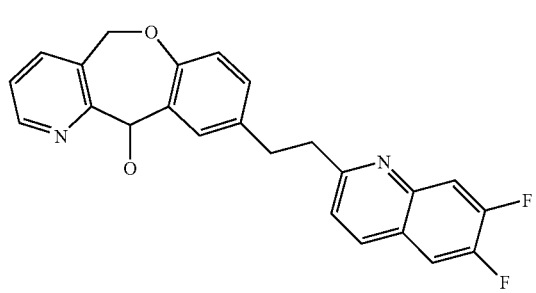

Starting from the previous compound and using the same procedure than in Example 23, step 7, the corresponding derivative is obtained in 92% yield.

Step 7: 3-{7-[2-(6,7-Difluoro-quinolin-2-yl)-ethyl]-5,11-dihydro-10-oxa-4-aza-dibenzo[a,d]cyclohepten-5-ylsulfanyl}-propionic Acid

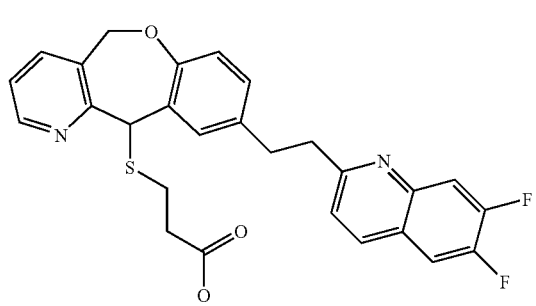

0.378 g (6.93 mmol) of the previous compound are suspended in 8 ml of dichloromethane. 3.8 ml of trifluoroacetic acid and 0.23 g (2.16 mmol) of 3-mercaptopropionic acid are added and the whole is stirred at 45° C. for 72 hr. The solvent is evaporated and the residue is partitioned between dichloromethane and water. The aqueous layer is brought to pH 5 with sodium bicarbonate solution. The organic layer is washed with water, dried and concentrated. The residue is taken up in ethyl ether and filtered, giving 0.29 g of the title product (63%).

[1]HRMN (d6-DMSO): 2.43 (t. 2H); 2.55-2.72 (m. 2H); 3.01 (t. 2H); 3.17-3.25 (m. 2H); 4.99-5.88 (AB syst. 2H); 5.83 (s. 1H); 6.75 (d. 1H); 7.07-7.10 (m. 1H); 7.31 (s. 1H); 7.37-7.41 (m. 1H); 7.51 (d. 1H); 8.81-7.84 (m. 1H); 7.93-8.05 (m. 2H); 8.28 (d. 1H); 8.44-8.46 (m. 1H).

Example 29

Preparation of N-{3-[7-(6,7-Difluoro-quinolin-2-ylmethoxy)-5,11-dihydro-10-oxa-1-aza-dibenzo[a,d]cyclohepten-5-ylsulfanyl]-propionyl}-benzene-sulfonamide

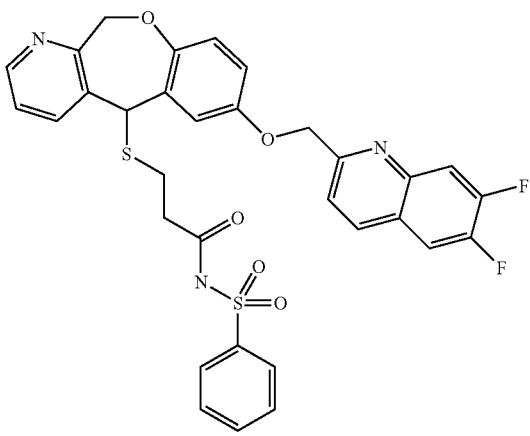

A mixture of 0.28 g 0.57 mmol) of the compound from Example 1 step 7, 0.09 g (0.57 mmol) of benzenesulfonamide, 0.144 g (0.7 mmol) of (3-dimethylaminopropyl)-ethylcarbodiimide, 0.092 g (0.75 mmol) of DMAP in 7 ml dichloromethane are stirred 16 hr at room temperature. Water and more dichloromethane are added and the organic layer is washed with water, dried and concentrated. The residue is chromatographied on SiO2 eluting with dichloromethane/methanol 95:5. Yield: 0.33 g (92%).

[1]HRMN (Cl3CD): 2.17-2.40 (m. 2H); 2.56-2.71 (m. 2H); 4.77 (s. 1H); 4.99-5.66 (AB syst. 2H); 5.31 (s. 2H); 6.87-6.94 (m. 2H); 7.07 (d. 1H); 7.49-7.67 (m. 6H); 7.77.7.84 (m. 1H); 8.04-8.06 (m. 2H); 8.14 (d. 1H); 8.44-8.46 (m. 1H).

Example 30

Preparation of 4-[7-(6,7-Difluoro-quinolin-2-ylmethoxy)-5,11-dihydro-10-oxa-1-aza-dibenzo[a,d]cyclohepten-5-ylsulfanyl]-butyric Acid Step 1: 4-mercaptobutyric Acid

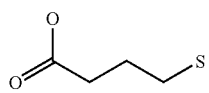

This compound was prepared according to U.S. Pat. No. 5,872,280.

Step 2: 4-[7-(6,7-Difluoro-quinolin-2-ylmethoxy)-5,11-dihydro-10-oxa-1-aza-dibenzo[a,d]cyclohepten-5-ylsulfanyl]-butyric Acid

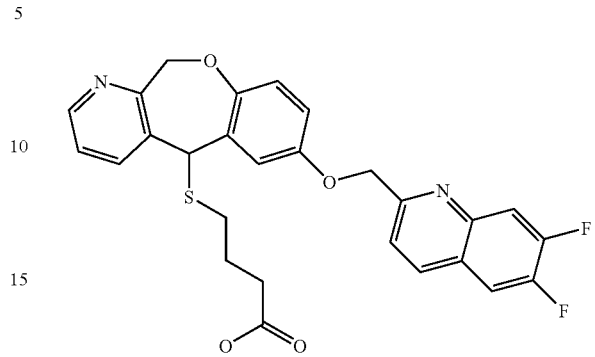

A mixture of 0.3 g (0.74 mmol) of the compound from Example 1 step 6, 0.17 g (1.41 mmol) of the previous compound, 2.5 ml of trifluoroacetic acid and 10 ml of dichloromethane are stirred at room temperature for 16 hr. The solvents are eliminated, the residue partitioned between dichloromethane and water, the pH made 5 with sodium bicarbonate and the organic layer washed with water, dried and concentrated. By addition of a little ethyl ether crystallises the title product. Yield: 0.3 g (80%).

[1]HRMN (d6-DMSO): 1.64-1.69 (m. 2H); 2.20 (t. 2H); 2.42 (t. 2H); 4.86-5.67 (AB syst. 2H); 5.10 (s. 1H); 5.33 (s. 2H); 6.97 (s. 2H); 7.08 (s. 1H); 7.30-7.34 (m. 1H); 7.69-7.77 (m. 2H); 8.00-8.13 (m. 2H); 8.42-8.45 (m. 2H); 12.10 (s. 1H).

Example 31

Preparation of 3-[7-(6,7-Difluoro-quinolin-2-ylmethoxy)-5,11-dihydro-10-oxa-1-aza-dibenzo[a,d]cyclohepten-5-ylsulfanyl]-propionamide

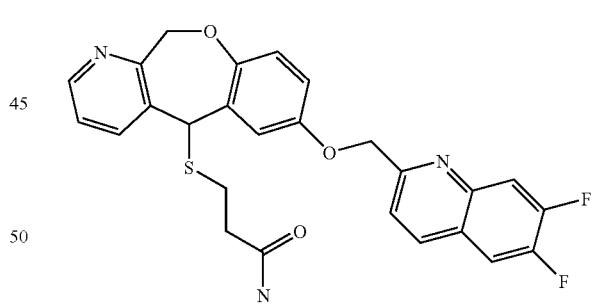

0.3 g (0.61 mmol) of the product from Example 1 step 7 is dissolved in 20 ml THF. 0.1 g (0.61 mmol) of carbonyldiimidazole are added and the system is stirred at room temperature for 16 hr. 10 ml of NH3 saturated ethanol are added and the stirring is prosecuted for 6 hr. The solvents are eliminated and the residue is partitioned between dichloromethane and water. The organic layer is washed with water, dried, concentrated and the residue is chromatographied on SiO2 eluting with C12CH2/MeOH/aq NH3 40:8:1. Yield: 0.13 g (43%).

[1]HRMN (d6-DMSO): 2.31 (t. 2H); 2.60 (t. 2H); 4.87-5.66 (AB syst. 2H); 5.15 (s. 1H); 5.33 (s. 2H); 6.92 (s. 1H); 6.97 (s. 2H); 7.11 (s. 1H); 7.32-7.38 (m. 2H); 7.70-7.79 (m. 2H); 8.01-8.14 (m. 2H); 8.42-8.45 (m. 2H).

Example 32

Preparation of 3-[7-(7-Chloro-6-fluoro-quinolin-2-ylmethoxy)-5H-benzo[4,5]cyclohepta[1,2-b]pyridin-5-ylsulfanyl]-propionic Acid Step 1:
7-Methoxy-benzo[4,5]cyclohepta[1,2-b]pyridin-5-one

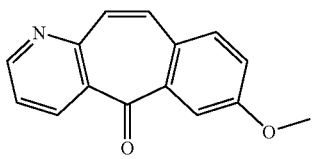

A mixture of 2.3 g (9.6 mmol) of the product from Example 23 step 4, 1.85 g (16.6 mmol) of selenium dioxide and 5 ml of pyridine is stirred at 120° C. for 6 hr. The whole is poured into excess petroleum ether and the solution is evaporated giving 0.55 g (24%) of enough pure title product as to prosecute with the synthesis.

Step 2:
7-Hydroxy-benzo[4,5]cyclohepta[1,2-b]pyridin-5-one

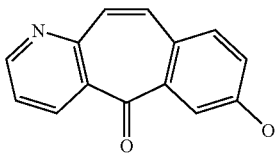

A solution of 0.55 g (2.31 mmol) of the previous compound in 10 ml of 48% aqueous hydrobromic acid is stirred at 125° C. for 6 hr. Once cooled, the system is made alkaline with 6N NaOH and neutralized with acetic acid. The solid thus precipitated is filtered, washed with water and dried. Yield: 0.49 g (95%).

Step 3: 7-(7-Chloro-6-fluoro-quinolin-2-ylmethoxy)-benzo[4,5]cyclohepta[1,2-b]pyridin-5-one

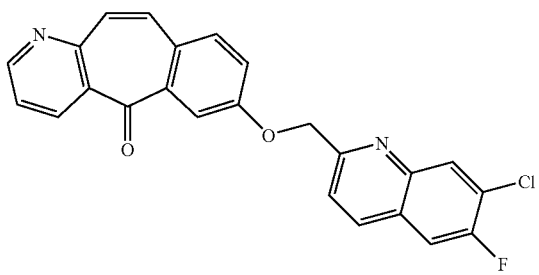

0.17 g (0.76 mmol) of the previous compound are dissolved in 5 ml DMF. 0.03 g (0.75 mmol) of 60% sodium hydride are added and the system is stirred for 30' at room temperature. 0.21 g (0.76 mmol) of the product from Example 3, step 2 are added and the stirring is prosecuted for 16 hr. The solvent is evaporated and the residue partitioned between dichloromethane and water. The organic layer is dried and concentrated. By addition of a little ethyl ether some impurities are precipitated. After filtration, the solution is concentrated, thus crystallising 0.14 g (44%) of the title product.

Step 4: 7-(7-Chloro-6-fluoro-quinolin-2-ylmethoxy)-5H-benzo[4,5]cyclohepta[1,2-b]pyridin-5-ol

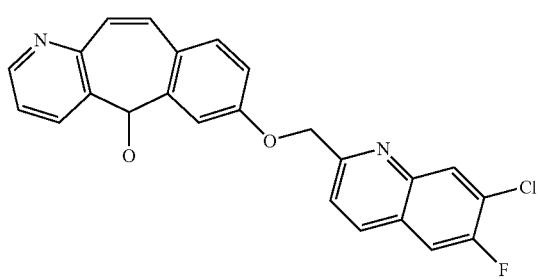

0.14 g (0.33 mmol) of the previous compound are suspended in 3 ml of THF and 2 ml of methanol. There are added 0.015 g (0.4 mmol) of sodium borohydride at room temperature. After stirring for 1 hr the solvent is evaporated and the residue is stirred with hot water, filtered and dried. Yield: 0.13 g (92%).

Step 5: 3-[7-(7-Chloro-6-fluoro-quinolin-2-ylmethoxy)-5H-benzo[4,5]cyclohepta[1,2-b]pyridin-5-ylsulfanyl]-propionic Acid

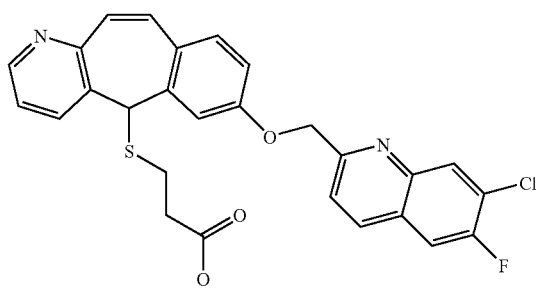

A mixture of 0.13 g (0.3 mmol) of the previous compound, 0.052 ml (0.06 g; 0.6 mmol) of 3-mercaptopropionic acid, 1.06 ml of trifluoroacetic acid and 5 ml dichloromethane are stirred overnight at room temperature. After concentration, the residue is partitioned between dichloromethane and water, the pH of the aqueous layer made 5 with sodium bicarbonate and the organic layer dried and concentrated. 0.075 g of the title product crystallises. Yield: 48%.

[1]HRMN (d6-DMSO): 2.32-2.36 (m. 4H); 5.43 (s. 3H); 6.91-6.95 (m. 1H); 7.05-7.16 (m. 2H); 7.30-7.44 (m. 3H); 7.74-7.77 (m. 11H); 7.82-7.84 (m. 1H); 8.06-8.09 (m. 1H); 8.20-8.31 (m. 1H); 8.43-8.52 (m. 2H); 12.20 (s. 1H).

Example 33

Preparation of 3-[7-(6,7-Difluoro-quinolin-2-yl-methoxy)-5H-benzo[4,5]cyclohepta[1,2-b]pyridin-5-ylsulfanyl]-propionic Acid

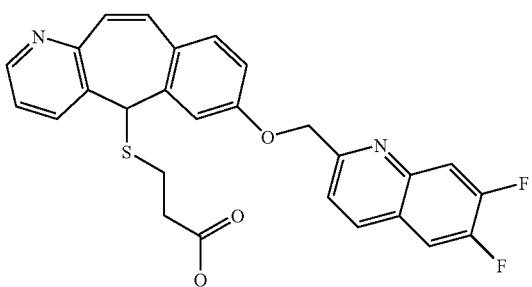

Starting from the product of Example 32, step 2, substituting the alkylating agent for the corresponding to that of Example 1, step 2, and operating subsequently as in the previous example, the title product is obtained in similar yields to that described previously.

[1]HRMN (d6-DMSO): 2.33-2.35 (m. 4H); 5.43 (s. 3H); 6.90-6.94 (m. 1H); 7.05-7.16 (m. 2H); 7.29-7.44 (m. 3H); 7.70-07.73 (m. 1H); 7.82-7.84 (m. 1H); 8.02-8.14 (m. 2H); 8.42-8.52 (m. 2H); 12.22 (s. 1H).

Example 34

Preparation of (+)-3-[7-(6,7-Difluoro-quinolin-2-ylmethoxy)-5,11-dihydro-10-oxa-1-aza-dibenzo[a,d]cyclohepten-5-ylsulfanyl]-propionic Acid

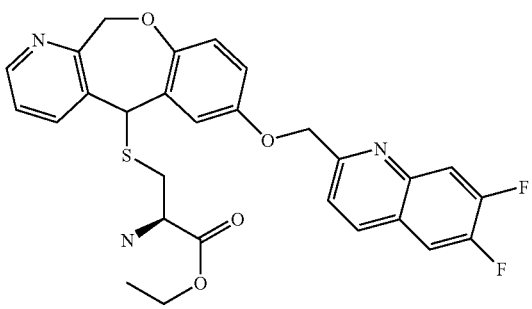

Step 1: 2-(R-Amino-3-[7-(6,7-difluoro-quinolin-2-ylmethoxy)-5,11-dihydro-10-oxa-1-aza-dibenzo[a,d]cyclohepten-5-ylsulfanyl]-propionic Acid Ethyl Ester and Separation of Diastereomers A mixture of 9.9 g (24.35 mmol) of the product from Example 1, step 6, 5.4 g (29.08 mmol) of L-cystein ethyl ester hydrochloride and 84 ml of trifluoroacetic acid are stirred at room temperature for 16 hr. The solvent is evaporated and the residue partitioned between sat. NaHCO3 and ethyl ether with a few drops of dichloromethane. The organic layer is washed with water, dried and concentrated, giving an oil which soon crystallises. Yield 11.9 g (90%).

The product is stirred at room temperature during 30' with 200 ml of ethyl ether and filtered. The solid (9 g) is dissolved in ml of dichloromethane and ml of diisopropyl ether added. The solid precipitated (6 g) is filtered and crystallised twice again from dichloromethane diisopropyl ether. There are thus obtained 1.9 g of a solid with m.p. 123-124° C., $[\alpha]_D=+38°$ (EtOH) and HPLC purity of 96.2%. All but the last combined mother liquors are concentrated and the residue (10 g) is crystallised from 100 ml ethanol and 65 ml water giving 4.2 g of solid material. After a new crystallisation step from 42 ml ethanol and 27 ml water, 3.6 g of a product with m.p. 70-73° C., $[\alpha]_D=-12.9°$ (EtOH) and HPLC purity of 98.7% are obtained.

Step 2: (+)-3-[7-(6,7-Difluoro-quinolin-2-yl-methoxy)-5,11-dihydro-10-oxa-1-aza-dibenzo[a,d]cyclohepten-5-ylsulfanyl]-propionic Acid

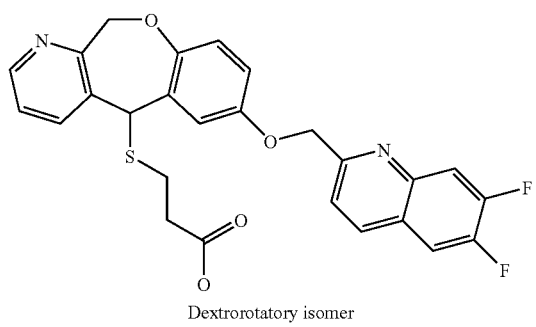

Dextrorotatory isomer

A mixture of 3.2 g (5.95 mmol) of the previous Cl2CH2/iPr2O crystallised isomer, 80 ml of dichloromethane, 0.085 ml of acetic acid and 0.96 ml (0.84 g; 7.1 mmol) of isoamyl nitrite are stirred at reflux temperature (under N2 atmosphere) for 2 hr. The solvent is eliminated and the residue partitioned between hexane/water. The organic layer is washed with 4% NaHCO3, water, and is dried and concentrated giving 3.2 g (98%) of the corresponding diazo derivative. This compound is dissolved in 64 ml of dichloromethane, the solution is cooled at 0° C. while 13 ml of 57% IH are dropped slowly at this temperature. The stirring at 0° C. is prosecuted for 1 hr. The system is then neutralised with sat. NaHCO3, sufficient 40% solution of sodium bisulphite is added to decolourise and the product is extracted with excess diethyl ether. The organic layer is washed with water, dried and concentrated, giving 2.4 g of product, which is dissolved in 24 ml THF. A solution of 0.38 g of lithium hydroxide in 8 ml water is added and the whole is stirred at room temperature for 2 hr. After concentration the residue is washed with diethyl ether and filtered. The residue is partitioned between 10% citric acid solution and ethyl acetate. The organic layer is dried and concentrated giving 1.3 g of product, which is purified by two SiO2 chromatographies, the first one eluting with ethyl acetate/acetone/acetic acid 100:20:1, and the second one with dichloromethane/methanol/aq.ammonia 40:8:1. The process yields 0.43 g of a solid of $[\alpha]_D+4.80$, with an optical purity of 96.3% (capillary electrophoresis).

Example 35

Preparation of (−)-3-[7-(6,7-Difluoro-quinolin-2-ylmethoxy)-5,11-dihydro-10-oxa-1-aza-dibenzo[a,d]cyclohepten-5-ylsulfanyl]-propionic Acid

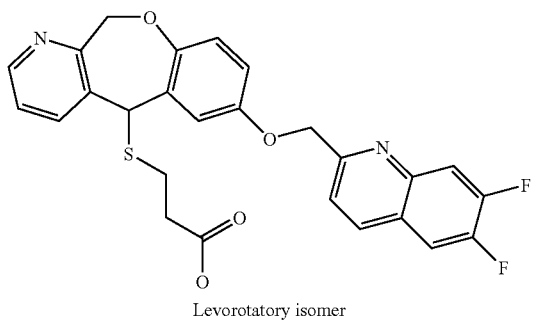

Levorotatory isomer 3.5 g of the ethanol/water crystallised isomer from Example 34, step 1 are transformed into the corresponding diazo derivative and subsequently deaminated, saponified and purified following the method shown in the previous example. 0.53 g of the title acid are obtained with $[\alpha]_D=-4.5°$, with an optical purity of 89.4% (capillary electrophoresis).

Example 36

Preparation of 3-[9-(6,7-Difluoro-quinolin-2-ylmethoxy)-6,11-dihydro-5Hbenzo[5,6]cyclohepta[1,2-c]pyridin-11-ylsulfanyl]-propionic Acid Step 1: 5,6-Dihydro-benzo[5,6]cyclohepta[1,2-c]pyridin-11-one

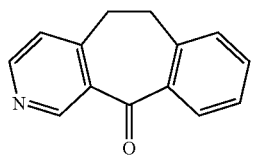

This compound was prepared according to J. Heterocycl. Chem. 1971, 8(1), 73.

Step 2: 9-Nitro-5,6-dihydro-benzo[5,6]cyclohepta[1,2-c]pyridin-11-one

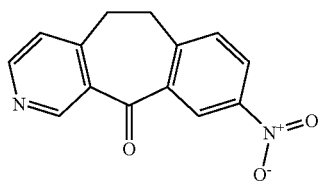

A mixture of 7.6 ml of fuming nitric acid and 1.6 ml of concentrated sulphuric acid is cooled in an ice bath. 1.6 g (7.6 mmol) of the previous compound are added in portions with stirring during one hour and the whole is stirred for 20 additional minutes at the same temperature and 45 minutes at 50° C. The solution is poured into excess ice and is basified with excess 2N NaOH. After heating at 40° C. for some minutes, the solid is filtered, washed with water and dried. After crystallising from acetone, 1.1 g (56%) of the title compound are obtained.

Step 3: 9-Amino-5,6-dihydro-benzo[5,6]cyclohepta[1,2-c]pyridin-11-one

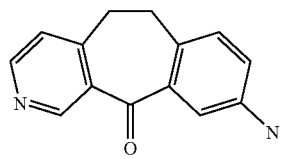

A suspension of 0.6 g (0.23 mmol) of the previous compound are suspended in 5 ml of acetic acid. After heating at 90° C. 1.8 g (0.79 mmol) of tin (II) chloride dihydrate are added in portions. The stirring at 90° C. is prosecuted for 15 additional minutes. After pouring into excess ice and basifying with 2N NaOH, the product is extracted with dichloromethane, washed with water and concentrated. 0.575 g of the aminocetone are obtained and used directly in the next step.

Step 4: 9-Hydroxy-5,6-dihydro-benzo[5,6]cyclohepta[1,2-c]pyridin-11-one

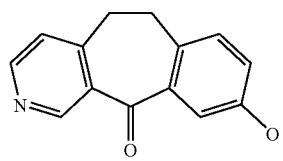

0.19 g of sodium nitrite are added during 10' to 1.9 ml of concentrated sulphuric acid. The whole is heated at 70° C. until clear solution. A solution of 0.575 g (0.25 mmol) of the previous compound in 5.4 ml of acetic acid is dropped at 25-30° C. The system is stirred for 10' and the diazonium salt solution is dropped into 52 ml of 10% sulphuric acid at reflux temperature. After 15' of refluxing, the solution is concentrated in vacuum and the residue is treated successively with 2N NaOH till basic pH and acetic acid to pH 5. The product is extracted with ethyl acetate, the solution is washed with water, dried and concentrated. 0.36 g of pure title compound are thus obtained (63%).

Step 5: 9-(6,7-Difluoro-quinolin-2-ylmethoxy)-5,6-dihydro-benzo[5,6]cyclohepta[1,2-c]pyridin-11-one

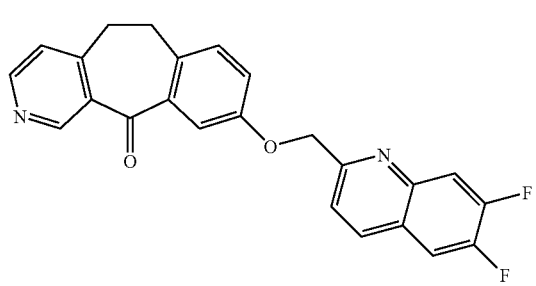

0.175 g (0.77 mmol) of the previous compound are dissolved in 5 ml DMF. 0.0312 g (0.78 mmol) of 60% sodium hydride are added and the system is stirred for 20' at room temperature. 0.211 g (0.82 mmol) of the product from Example 1, step 2 are added and the stirring is prosecuted for 16 hr. The solvent is evaporated and the residue partitioned between dichloromethane and water. The organic layer is dried and concentrated. 0.304 g (97%) of the title product are thus obtained.

Step 6: 9-(6,7-Difluoro-quinolin-2-ylmethoxy)-6,11-dihydro-5H-benzo[5,6]cyclohepta[1,2-c]pyridin-11-ol

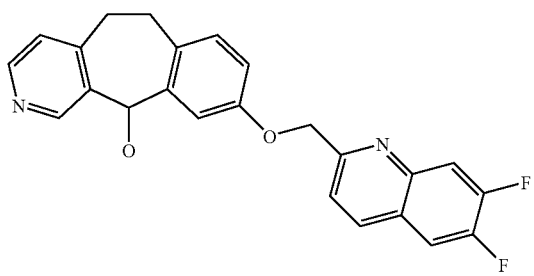

0.304 g (0.75 mmol) of the previous compound are suspended in 6 ml of THF and 2 ml of methanol. With stirring and ice bath cooling, there are added 0.036 g (0.96 mmol of sodium borohydride. After stirring for 1 hr at room temperature, the solvent is evaporated and the residue is stirred with hot water, filtered and dried. Yield: 0.264 g (86%).

Step 7: 3-[9-(6,7-Difluoro-quinolin-2-ylmethoxy)-6,11-dihydro-5H-benzo[5,6]cyclohepta[1,2-c]pyridin-11-ylsulfanyl]-propionic Acid

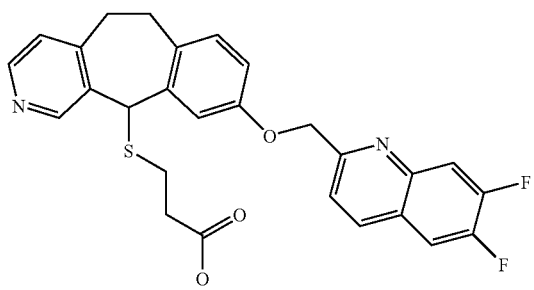

A mixture of 0.264 g (0.65 mmol) of the previous compound, 0.11 ml (0.12 g; 1.27 mmol) of 3-mercaptopropionic acid, 2.3 ml of trifluoroacetic acid and 5.5 ml dichloromethane are stirred at 45° C. for 72 hr. After concentration, the residue is partitioned between dichloromethane and water, the pH of the aqueous layer made 5 with sodium bicarbonate and the organic layer dried and concentrated. 0.13 g of the title product crystallises. Yield: 40%.

[1]HRMN (d6-DMSO): 2.39-2.57 (m. 4H); 2.73-2.87 (m. 2H); 3.37-3.45 (m. 1H); 3.74-3.84 (m. 1H); 5.32 (s. 1H); 5.35 (s. 2H); 6.90-6.945 (m. 1H); 7.12-7.16 (m. 3H); 7.69 (d. 1H); 8.01-8.13 (m. 2H); 8.30 (d. 1H); 8.41-8.46 (m. 2H); 12.2 (b.s., 1H).

Example 37

Preparation of 3-[9-(7-Chloro-6-fluoro-quinolin-2-ylmethoxy)-6,11-dihydro-5H-benzo[5,6]cyclohepta[1,2-c]pyridin-11-ylsulfanyl]-propionic Acid

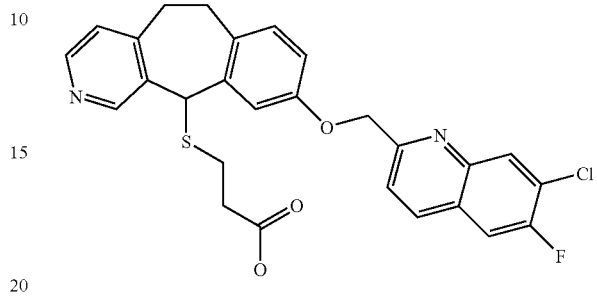

Starting from the product of Example 35, step 3, substituting the alkylating agent for the corresponding- to that of Example 3, step 2, and operating subsequently as in the previous example, the title product is obtained in similar yields to that described previously.

[1]HRMN (d6-DMSO): 2.39-2.57 (m. 4H); 2.73-2.86 (m. 2H); 3.27-3.44 (m. 1H); 3.75-3.84 (m. 1H); 5.30 (s. 1H); 5.35 (s. 2H); 6.91-6.94 (m. 1H); 7.13-7.16 (m. 3H); 7.72 (d. 1H); 8.06 (d. 1H); 8.28 (d. 1H); 8.43 (d. 2H); 12.2 (b.s., 1H).

Example 38

Preparation of 3-{9-[2-(6,7-Difluoro-quinolin-2-yl)-vinyl]-11H-benzo[5,6]cyclohepta[1,2-c]pyridin-11-ylsulfanyl}-propionic Acid Step 1: 4-[2-(4-Bromo-phenyl)-vinyl]-nicotinic Acid

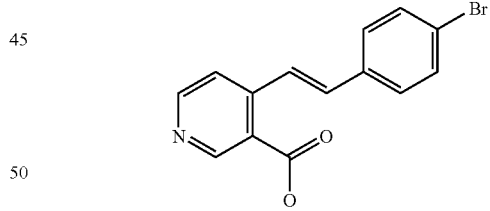

0.9 g (22.5 mmol) of a 60% suspension of sodium hydride in paraffin are added to a solution of 2.25 g (30.40 mmol) of tertbutanol in 27.5 ml of DMF. The whole is heated in a water bath for 30' till the evolution of hydrogen ends. The system is cooled at 0° C. and 2.5 g (15.13 mmol) of ethyl 4-methylnicotinate in 2.5 ml of DMF are dropped with stirring. After 1.5 hr stirring at the same temperature, 3.4 g (18.37 mmol) of 4-bromobenzaldehyde in 2.5 ml DMF are dropped. The system is stirred at room temperature overnight. The solution is poured over 100 g of ice and is filtered. The filtrate is acidified with acetic acid and the solid is filtered, washed with water and dried, yielding 1.85 g (40%) of a product that is used directly in the next step.

Step 2: 9-Bromo-benzo[5,6]cyclohepta[1,2-c]pyridin-11-one

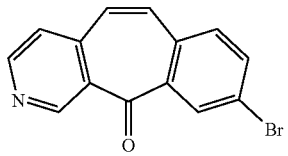

A mixture of 16 g of PPA and 1.3 g (4.27 mmol) of the previous compound is stirred at 225° C. for 45'. After cooling to 100° C. the whole is poured into water, basified with NaOH and extracted with dichloromethane. The organic layer is washed with brine, dried and concentrated, yielding 0.6 of the pure product (49%).

Step 3: 9-Bromo-11H-benzo 5,6]cyclohepta[1,2-c]pyridin-11-ol

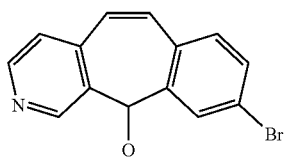

A solution of 0.46 g (1.61 mmol) of the previous compound in 12 ml of THF and 4 ml of methanol is cooled externally with an ice bath. 0.073 g (1.93 mmol) of sodium borohydride are added in portions, with stirring. After stirring 1 hr at room temperature, the solvent is evaporated in vacuo. The residue is suspended in water, filtered and washed with more water. Once dried, it weighs 458 mg (99%).

Step 4: 9-[2-(6,7-Difluoro-quinolin-2-yl)-vinyl]-11H-benzo[5,6]cyclohepta[1,2-c]pyridin-11-ol

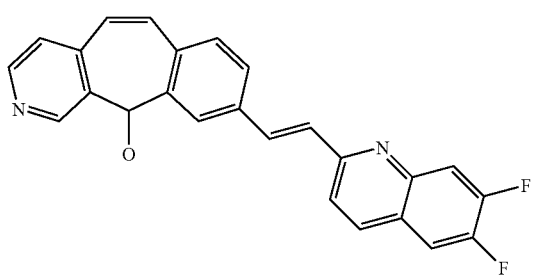

A mixture of 225 mg (0.78 mmol) of the previous compound, 166 mg (0.87 mmol) of the compound from Example 10, step 4, 5 mg of palladium acetate, 22 mg of tri-o-tolylphosphine and 1.5 ml of DMF is stirred in a N2 atmosphere. After cooling with ice bath a solution of 0.17 ml of triethylamine in 0.8 ml of DMF is dropped into the system and the whole is heated at 100° C. for 1 h. Once at room temperature, 3 ml of water are dropped and the solid precipitated is filtered and washed with water and diisopropyl ether. The yield is 279 mg (90%).

Step 5: 3-{9-[2-(6,7-Difluoro-quinolin-2-yl)-vinyl]-11H-benzo[5,6]cyclohepta[1,2-c]pyridin-1-ylsulfanyl}-propionic Acid

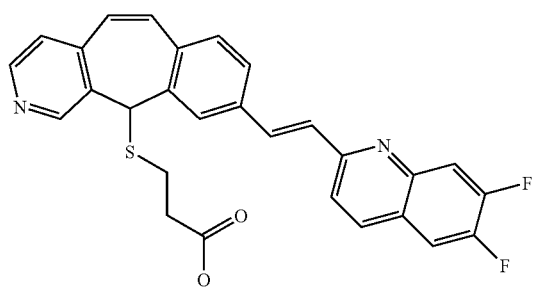

276 mg (0.69 mmol) of the previous compound are suspended in 5.8 ml of dichloromethane. 2.4 ml of trifluoroacetic acid and then 0.12 ml (0.13 g; 1.38 mmol) of 3-mercaptopropionic acid are added. The solution is heated at 45° C. for 72 hr and the solvent is then eliminated in vacuo. The residue is stirred with water and dichloromethane. The pH of the aqueous layer is made 5 by addition of sodium bicarbonate. The organic layer is washed with water, dried and concentrated. The product crystallises by addition of diethyl ether. Yield 130 mg (38%).

[1]HRMN (d6-DMSO): 2.42-2.44 (m. 4H); 5.63 (s. 1H); 7.01-7.27 (m. 2H); 7.41-7.55 (m. 2H); 7.58 (d. 1H); 7.71-7.74 (m. 1H); 7.86-8.09 (m. 5H); 8.40 (d. 1H); 8.51 (d. 1H); 8.68 (s. 1H); 12.23 (b.s. 1H).

Example 39

Preparation of 3-{7-[2-(6,7-Difluoro-quinolin-2-yl)-vinyl]-5H-benzo[[4,5]cyclohepta[1,2-b]pyridin-5-ylsulfanyl}-propionic Acid

Step 1: 7-Bromo-benzo[4,5]cyclohepta[1,2-b]pyridin-5-one

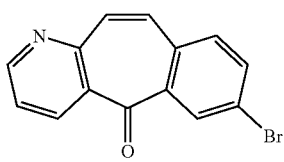

This compound was prepared as described in J. Heterocyclic Chem., 23, 1331 (1986).

Step 2: 7-[2-(6,7-Difluoro-quinolin-2-yl)-vinyl]-benzo[4,5]cyclohepta[1,2-b]pyridin-5-one

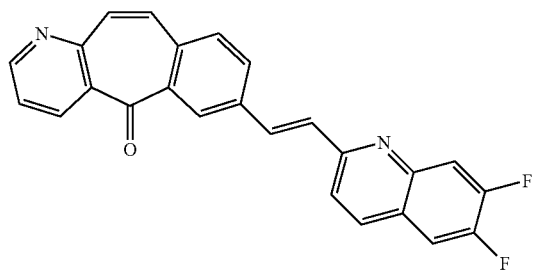

A mixture of 300 mg (1.048 mmol) of the previous compound, 223 mg (1.169 mmol) of the compound from Example 10, step 4, 6.0 mg of palladium acetate, 30 mg of tri-o-tolylphosphine and 2.0 ml of DMF is stirred in a N2 atmosphere. After cooling with ice bath a solution of 0.23 ml of triethylamine in 1.0 ml of DMF is dropped into the system and the whole is heated at 100° C. for 1 h. Once at room temperature, 4 ml of water are dropped and the solid precipitated is filtered and washed with water and diisopropyl ether. The yield is 340 mg (82%)

Step 3: 7-[2-(6,7-Difluoro-quinolin-2-yl)-vinyl]-5H-benzo[4,5]cyclohepta[1,2-b]pyridin-5-ol

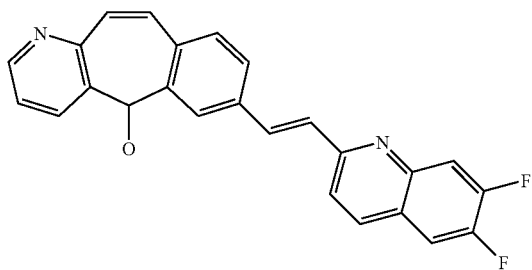

340 mg (0.85 mmol) of the previous compound are dissolved in 5 ml of THF and 3 ml of methanol. With stirring and ice bath cooling, there are added 0.042 g (1.1 mmol) of sodium borohydride. After stirring for 1 hr at room temperature, the solvent is evaporated and the residue is stirred with hot water, filtered and dried. Yield: 0.30 g (88%).

Step 4: 3-{7-[2-(6,7-Difluoro-quinolin-2-yl)-vinyl]-5H-benzo[4,5]cyclohepta[1,2-b]pyridin-5-ylsulfanyl}-propionic Acid

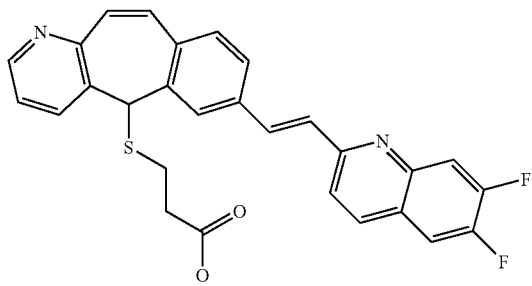

150 mg (0.376 mmol) of the previous compound

A mixture of 0.15 g (0.376 mmol) of the previous compound, 0.065 ml (0.07 g; 0.75 mmol) of 3-mercaptopropionic acid, 1.32 ml of trifluoroacetic acid and 6 ml dichloromethane are stirred overnight at room temperature. After concentration, the residue is partitioned between dichloromethane and water, the pH of the aqueous layer made 5 with sodium bicarbonate and the organic layer dried and concentrated. 0.140 g of the title product crystallises. Yield: 76%.

[1]HRMN (Cl3CD): 2.42-2.62 (m. 4H); 5.32 (s. 1H); 7.22-7.86 (c.s. 12H); 8.15 (d. 1H); 8.50 (m. 1H).

Example 40

Preparation of (1-{7-[2-(6,7-Difluoro-quinolin-2-yl)-vinyl]-5H-benzo[4,5]cyclohepta[1,2-b]pyridin-5-ylsulfanylmethyl}-cyclopropyl) Acetic Acid

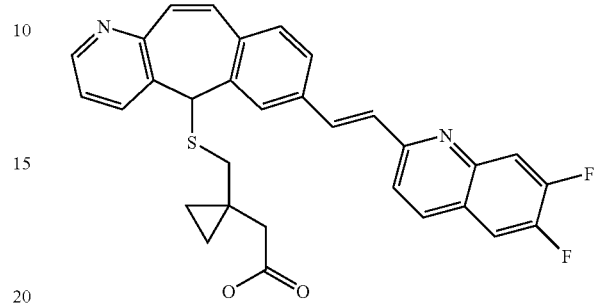

A mixture of 0.120 g (0.30 mmol) of compound from Example 39 step 3, 0.1 g (0.62 mmol) of the compound from Example 7 step 1, 1.2 ml of trifluoroacetic acid and 5 ml dichloromethane is stirred overnight at room temperature. After concentration, the residue is dissolved in 10 ml ethanol. 3 ml 2N NaOH are added and the whole is stirred at room temperature for 16 hr. After neutralising with 2N HCl the ethanol is evaporated and the product extracted with dichloromethane and dried. Upon concentration and treatment with isopropyl ether 0.10 g of the title product crystallises (64% global yield).

[1]HRMN (Cl3CD): 0.35-0.58 (m. 4H); 2.11-2.36 (m. 2H); 2.52-2.65 (m. 2H); 5.28 (s. 1H); 7.21-7.80 (c.s. 12H); 8.19 (d. 1H); 8.48-8.52 (m. 1H).

Example 41

Preparation of 3-{7-[2-(7-Chloro-5-fluoro-quinolin-2-yl)-vinyl]-5H-benzo[4,5]cyclohepta[1,2-b]pyridin-5-ylsulfanyl}-propionic Acid

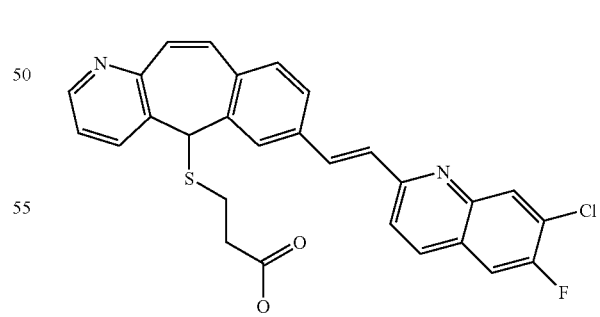

This compound is prepared in a parallel way to that of Example 39, but substituting the 6,7-difluoro-2-vinylquinoline from Example 10, step 4, for the corresponding 7-chloro-6-fluoro-2-vinylquinoline

[1]HRMN (Cl3CD): 2.42-2.63 (m. 4H); 5.31 (s. 1H); 7.21-7.76 (c.s. 1H); 8.08-8.17 (m. 2H); 8.51-8.58 (m. 1H).

Example 42

Preparation of (1-{7-[2-(7-Chloro-6-fluoro-quinolin-2-yl)-vinyl]-5H-benzo[4,5]cyclohepta[1,2-b]pyridin-5-ylsulfanylmethyl}-cyclopropyl)-acetic Acid

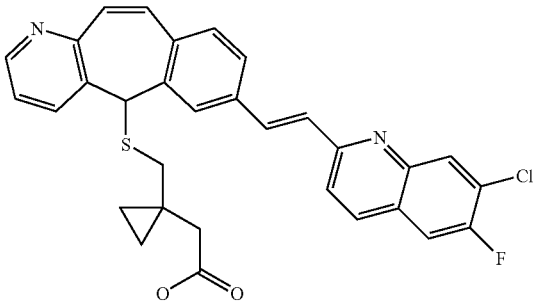

This compound is prepared in a parallel way to that of Example 40, but substituting the 6,7-difluoro-2-vinylquinoline from Example 10, step 4, for the corresponding 7-chloro-6-fluoro-2-vinylquinoline.

[1]HRMN (Cl3CD): 0.33-0.39 (m. 4H); 2.15 (s. 2H); 2.47 (s. 2H); 5.40° (s. 1H); 7.07-7.12 (m. 1H); 7.25-7.29 (m. 1H); 7.38-7.43 (m. 2H); 7.53-7.58 (m. 2H); 7.71-7.74 (m. 1H); 7.85-7.87 (m. 2H); 7.91-8.05 (m. 2H); 8.21-8.23 (m. 1H); 8.39-8.42 (m. 1H); 8.53-8.54 (m. 1H); 12.05 (b.s. 1H).

Example 43

Preparation of (+) 3-[7-(7-Chloro-6-fluoro-quinolin-2-ylmethoxy)-10,11-dihydro-5H-benzo[4,5]cyclohepta[1,2-b]pyridin-5-ylsulfanyl]-propionic Acid Step 1: 2-(R)-Amino-3-[7-(7-chloro-6-fluoro-quinolin-2-ylmethoxy)-10,11-dihydro-5H-benzo[4,5]cyclohepta[1,2-b]pyridin-5-ylsulfanyl]-propionic Acid Ethyl Ester

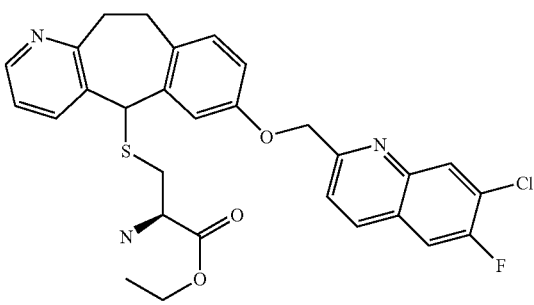

A mixture of 10.0 g (23.76 mmol) of the product from Example 23, step 7, 9.7 g (52.3 mmol) of L-cystein ethyl ester hydrochloride and 105 ml of trifluoroacetic acid is stirred at 60° C. for 48 hr. The solvent is evaporated and the residue partitioned between sat. NaHCO3 and chloroform. The organic layer is washed with water, dried and concentrated, giving an oil, which is crystallised from ethyl ether/diisopropyl ether. Yield 10.4 g (80%).

Step 2: 3-[7-(7-Chloro-6-fluoro-quinolin-2-ylmethoxy)-10,11-dihydro-5H-benzo[4,5]cyclohepta[1,2-b]pyridin-5-ylsulfanyl]-2-(R)-formylaminopropionic Acid Ethyl Ester and

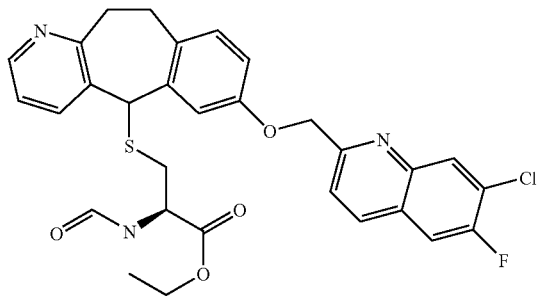

A mixture of 7.7 g (13.9 mmol) of the previous compound and 58 ml of ethyl formiate is refluxed for 2 hr. Once cold, the solid is filtered and washed with ethyl acetate, giving 5.2 g. It is recrystallised twice from THF, thus recovering 2.3 g of the more polar diastereomer (56%). The combined mother liquors are evaporated and recrystallised 5 times from ethanol/water, giving 1.7 g (42%) of the more polar diastereomer. The corresponding diastereomers are split in CCF using a mixture ethyl acetate/ethanol 10/0.5 as eluent.

[1]HRMN (Cl3CD) more polar diastereomer: 1.22 (t. 3H); 2.60-2.93 (m. 2H); 2.84-2.90 (m. 1H); 3.09-3.15 (m. 1H); 3.60-3.66 (m. 1H); 3.93-3.97 (m. 1H); 4.13-4-22 (m. 2H); 4.92-4.96 (m. 1H); 5.03 (s. 1H); 5.35 (s. 2H); 6.25 (d. 1H); 6.88-6.96 (m. 2H); 7.12-7.17 (m. 2H); 7.54 (d. 1H); 7.63-7.72 (2H); 8.12-8.15 (m. 2H); 8.25 (s. 1H); 8.43-8.44 (m. 1H).

[1]HRMN (Cl3CD) less polar diastereomer 1.29 (t. 3H); 2.75-2.94 (m. 2H); 2.84-2.94 (m. 1H); 3.06-3.14 (m. 1H); 3.68-3.81 (m. 1H); 3.82-3.86 (m. 1H); 4.22 (q. 2H); 4.79-4.84 (m. 1H); 4.91 (s. 1H); 5.35 (s. 2H); 6.15 (d. 1H); 6.87-6.92 (m. 2H); 7.09-7.15 (m. 2H); 7.55 (d. 1H); 7.67-7.70 (1H); 8.06 (s. 1H); 8.12-8.19 (m. 2H); 8.44 (m. 1H).

Step 3: (+) 2-(R)-Amino-3-[7-(7-chloro-6-fluoro-quinolin-2-ylmethoxy)-10,11-dihydro-5H-benzo[4,5]cyclohepta[1,2-b]pyridin-5-ylsulfanyl]-propionic Acid Ethyl Ester

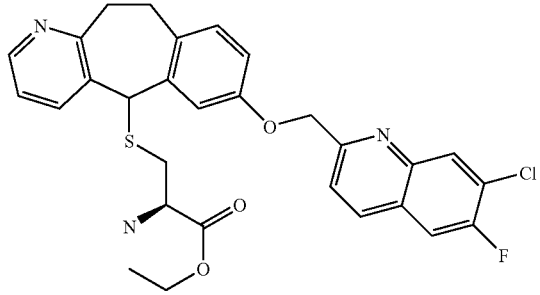

Dextrorotatory Isomer

A mixture of 1.6 g (2.76 mmol) of the more polar diastereomer from the previous step, 32 ml of HCl saturated ethanol and 1.6 ml of water is refluxed for 30'. The solid (0.80 g of the corresponding aminoester) is filtered and reesterified by boiling it for 90' with 25 ml of HCl saturated ethanol, evaporating to dryness and partitioning between sat NaHCO3 and ethyl acetate, giving rise to 0.41 g of aminoester. The solution from the hydrolysis is neutralised with excess sat NaHCO3 and extracted with ethyl acetate, dried and concentrated. The total yield of aminoester is 1.22 g (80%). The presence of the less polar diastereomer is not detected by means of HPLC of the corresponding aminoacid (prepared by hydrolysis with LiOH/H2O/THF).

In an alternative way, the diastereomers of step 1 can be separated chromatographically, eluting with a gradient from hexane/ethyl acetate 7/3 to ethyl acetate.

Step 4: (+) 3-[7-(7-Chloro-6-fluoro-quinolin-2-yl-methoxy)-10,11-dihydro-5H-benzo[4,5]cyclohepta[1,2-b]pyridin-5-ylsulfanyl]-2-diazo-propionic Acid Ethyl Ester

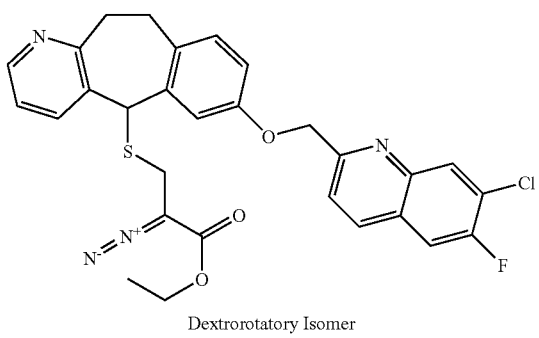

Dextrorotatory Isomer

A mixture of 0.915 g (1.66 mmol) of the compound from previous step, 23 ml of chloroform, 0.278 ml (1.98 mmol) of isoamyl nitrite and 0.0095 ml acetic acid is refluxed for 2.5 hr. Excess ethyl acetate is added and the solution is washed with water, brine, sat NaHCO3 and water. After drying and concentrating, the residue is chromatographied on SiO2 eluting with ethyl acetate/hexane 3:2. Yield: 0.64 g (69%). $[\alpha]_D$=+23.120

Step 5: (−) 3-[7-(7-Chloro-6-fluoro-quinolin-2-yl-methoxy)-10,11-dihydro-5H-benzo[4,5]cyclohepta[1,2-b]pyridin-5-ylsulfanyl]-2-hydrazono-propionic Acid Ethyl Ester

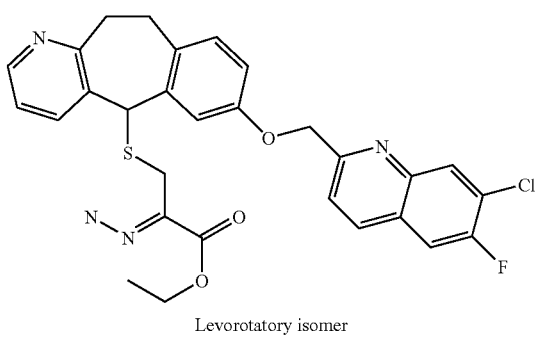

Levorotatory isomer 0.326 g (0.58 mmol) of the previous compound are dissolved in 12 ml of THF. 0.022 g (0.58 mmol) of sodium borohydride are added at 0° C. and the reaction is stirred 30' at 0° C. and 2 hr at room temperature. Excess ethyl acetate is added and the solution is washed with sat NaHCO3 and brine. After drying and evaporating, the residue is chromatographied on SiO2 eluting with a hexane/ethyl acetate 3:1 to ethyl acetate/methanol 9:1 gradient. Yield: 0.25 g (77%). $[\alpha]_D$=−7.52°

Step 6: (+) 3-[7-(7-Chloro-6-fluoro-quinolin-2-yl-methoxy)-10,11-dihydro-5H-benzo[4,5]cyclohepta[1,2-b]pyridin-5-ylsulfanyl]-propionic Acid

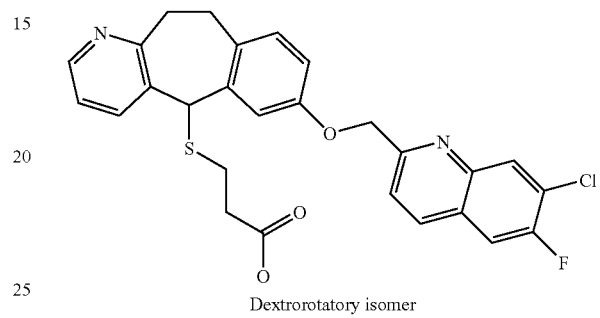

Dextrorotatory isomer 0.845 g (1.49 mmol) of the previous compound is dissolved in 20 ml chloroform. 1.12 ml of DBU (7.47 mmol) are added and the whole is stirred 16 hr under N2 at room temperature. Excess ethyl acetate is added and the solution is washed with citric acid solution, sat. NaHCO3 and brine. After drying and concentrating the residue is chromatographied on SiO2 eluting with ethyl acetate/hexane 2:1. Yield: 0.62 g (77%). $[\alpha]_D$=+44.7°. This compound is dissolved in 12 ml THF and a solution of 0.036 g (1.50 mmol) of lithium hydroxide in 12 ml water is added. The whole is stirred 4 hr at room temperature. After concentrating and adjusting the ph to 5 with acetic acid, the product is extracted with ethyl acetate and the solution is washed with brine, dried and concentrated; The residue is chromatographied on SiO2 eluting with chloroform/methanol/aqueous ammonia 95/10/1 to give 0.521 g (77%) of compound. $[\alpha]_D$=+40.9°

Example 44

Preparation of (−) 3-[7-(7-Chloro-4-fluoro-quinolin-2-ylmethoxy)-10,11-dihydro-5H-benzo[4,5]cyclohepta[1,2-b]pyridin-5-ylsulfanyl]-propionic Acid

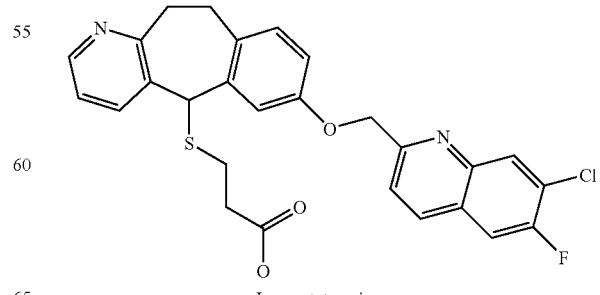

Levorotatory isomer

This compound is prepared in a parallel way to that described for the synthesis of the previous compound, but starting with the less polar diastereomer of step 2. [α]$_D$=38.9°.

Example 45

Preparation of (−)3-[7-(6,7-Difluoro-quinolin-2-ylmethoxy)-11-methyl-10,11-dihydro-5H-benzo[e]pyrido[2,3-b]azepin-5-ylsulfanyl]-propionic Acid Step 1: 2-Amino-3-[7-(6,7-difluoroquinolin-2-ylmethoxy)-11-methyl-10,11-dihydro-5H-benzo[e]pyrido[2,3-b]azepin-5-ylsulfanyl]-propionic Acid Ethyl Ester

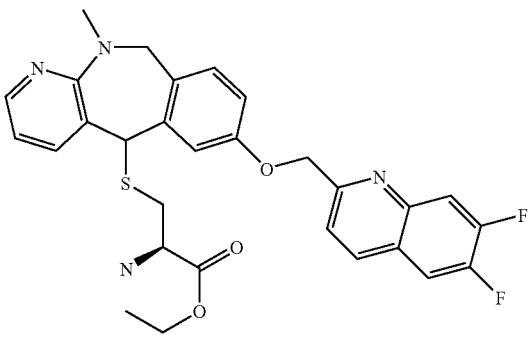

A mixture of 6.6 g (15.7 mmol) of the product from Example 21, step 5, 6.0 g (32.3 mmol) of L-cystein ethyl ester hydrochloride and 136 ml of trifluoroacetic acid in 198 ml of dichloromethane is stirred at 45° C. for 16 hr. The solvent is evaporated and the residue partitioned between sat. NaHCO3 and chloroform. The organic layer is washed with water, dried and concentrated, giving an oil, which solidifies with the aid of diisopropyl ether/petroleum ether. Yield 7.9 g (91%).

Step 2: 3-[7-(6,7-Difluoro-quinolin-2-ylmethoxy)-11-methyl-10,11-dihydro-5H-benzo[e]pyrido[2,3-b]azepin-5-ylsulfanyl]-2-formylamino-propionic Acid Ethyl Ester

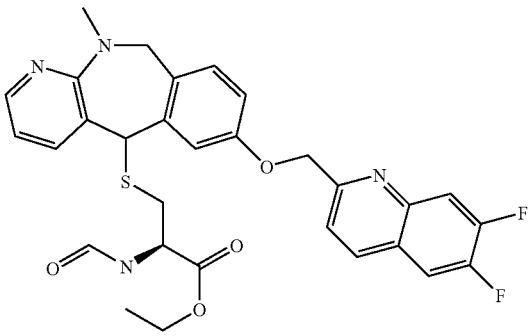

7.9 g (14.3 mmol) of the previous compound and 79 ml of ethyl formiate are refluxed for 2 hr (a solid appears). Once at room temperature, the solid is filtered and refluxed in 40 ml of THF for 15' and filtered. This process is repeated once more and the solid thus obtained is stirred at room temperature for 16 hr in 80 ml THF and filtered, giving 2.9 g of the first diastereomer. The ethyl formiate solution is evaporated and the residue crystallised from ethanol/water three times giving 2.09 of the second diastereomer.

[1]HRMN (Cl3CD) first diastereomer 1.21 (t. 3H); 2.59-2.66 (m. 1H); 2.94-3.00 (m. 1H); 3.24 (s. 3H); 3.83-3.88 (m. 1H); 4.12-4.19 (m. 2H); 4.90-4-96 (m. 2H); 5.35 (s. 2H); 5.72-5.77 (m. 1H); 6.24 (d. 1H); 6.53-6.57 (m. 1H); 6.91-6.94 (m. 2H); 7.15-7.18 (m. 1H); 7.43-7.46 (1H); 7.56 (t. 1H); 7.65-7.68 (m. 1H); 7.82-7.85 (m. 1H); 8.06-8.14 (m. 2H); 8.29 (s. 1H).

[1]HRMN (Cl3CD) second diastereomer 1.32 (t. 3H); 2.76-2.04 (m. 2H); 3.24 (s. 3H); 3.86-3.91 (m. 1H); 4.25 (q. 2H); 4.76-4-80 (m. 2H); 5.36 (s. 2H); 5.68-5.73 (m. 1H); 6.09-6.12 (m. 1H); 6.52-6.56 (m. 1H); 6.87-6.94 (m. 2H); 7.16-7.19 (m. 1H); 7.34-7.35 (1H); 7.54-7.67 (m. 2H); 7.82-7.86 (m. 1H); 8.01 (s. 1H); 8.09-8.15 (m. 2H).

Step 3: (−) 2-Amino-3-[7-(6,7-difluoro-quinolin-2-ylmethoxy)-11-methyl-10,11-dihydro-5H-benzo[e]pyrido[2,3-b]azepin-5-ylsulfanyl]-propionic Acid Ethyl Ester

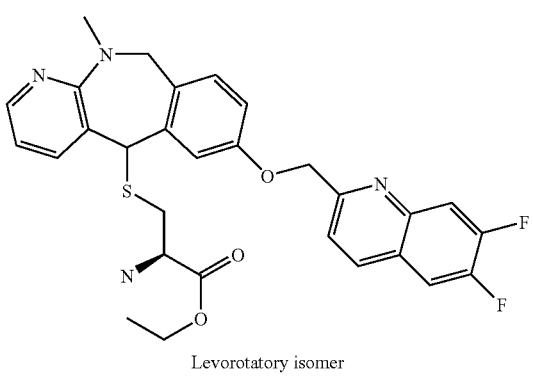

Levorotatory isomer 2.8 g (4.83 mmol) of the second diastereomer from the previous step in 55 ml of ethanol and 41.2 ml of HCl saturated ethanol are stirred for 4 hr at room temperature. 30 ml of diisopropyl ether are added and the solid is filtered. This compound is partitioned between ethyl acetate and 4% sodium bicarbonate. The organic layer is dried and concentrated to little volume. n-Hexane is added to crystallisation. Yield: 2.24 g (84%). [α]$_D$=194°.

Step 4: 2-diazo-3-[7-(6,7-Difluoro-quinolin-2-ylmethoxy)-11-methyl-10,11-dihydro-5H-benzo[e]pyrido[2,3-b]azepin-5-ylsulfanyl]-propionic Acid Ethyl Ester

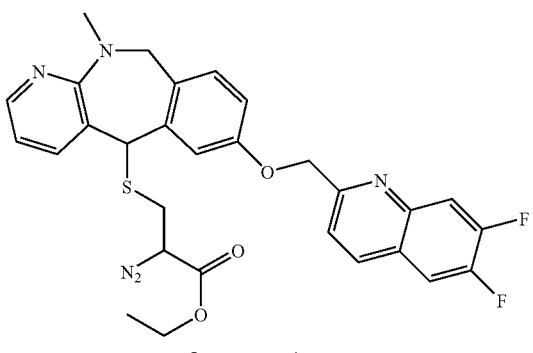

Levorotatory isomer 2.24 g (4.06 mmol) of the compound from the previous step is dissolved in 55 ml of chloroform. 0.023 ml of acetic acid are added, and 0.65 ml of isoamyl nitrite are dropped. The mixture is refluxed for 2.5 hr. Once at room temperature, the solution is washed with 4% sodium bicarbonate, dried and concentrated. The residue is chromatographied through SiO2 using chloroform as eluent. Yield: 1.0 g (43%).

Step 5: 3-[7-(6,7-Difluoro-quinolin-2-ylmethoxy)-1-methyl-10,11-dihydro-5H-benzo[e]pyrido[2,3-b]azepin-5-ylsulfanyl]-2-hydrazono-propionic Acid Ethyl Ester

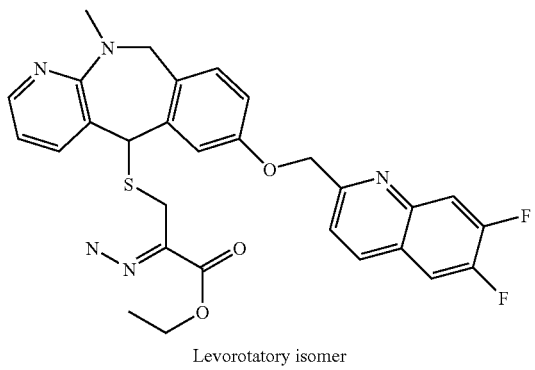

Levorotatory isomer 1.0 g (1.77 mmol) of the previous compound is dissolved in 37 ml THF. With stirring and external ice cooling, 0.075 g (1.9 mmol) of sodium borohydride are added in portions. After stirring for 3 hr at room temperature, 37 ml of ethyl ether and 37 ml of water are added and the organic layer is washed with more water, dried and concentrated. The residue is crystallised from petroleum ether. Yield: 0.8 g (80%).

Step 6: 3-[7-(6,7-Difluoro-quinolin-2-ylmethoxy)-11-methyl-10,11-dihydro-5H-benzo[e]pyrido[2,3-b]azepin-5-ylsulfanyl]-propionic Acid Ethyl Ester

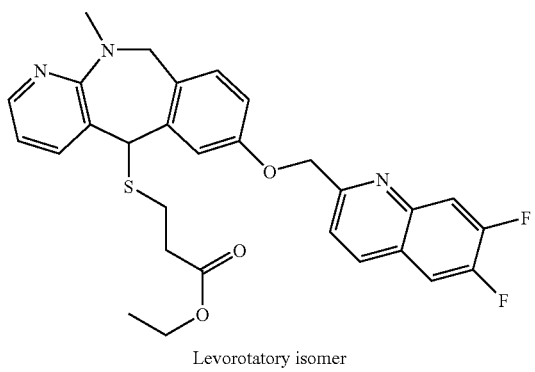

Levorotatory isomer 0.8 g (1.42 mmol) of the compound from the previous step are dissolved in 18 ml of chloroform. 1.06 ml (1.08 g; 7.08 mmol) of DBU are added and the system is stirred at room temperature for 24 hr and at 70° C. for 30 min. The solvent is evaporated, ethyl ether added and the solution is washed with water, diluted citric acid and water. The solution is dried and evaporated giving an oil which soon crystallises. Yield: 0.6 g (79%).

Step 7: (−) 3-[7-(6,7-Difluoro-quinolin-2-ylmethoxy)-11-methyl-10,11-dihydro-5H-benzo[e]pyrido[2,3-b]azepin-5-ylsulfanyl]-propionic Acid

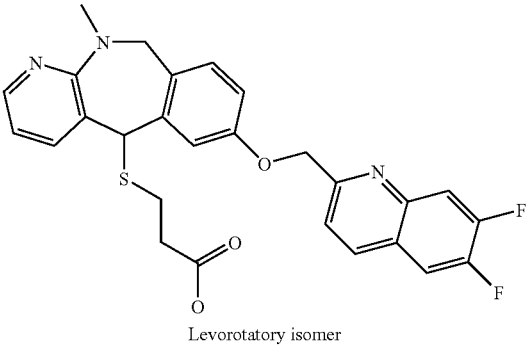

Levorotatory isomer 0.6 (1.06 mmol) of the compound from the previous step are suspended in 6 ml of THF. A solution of 0.054 g (2.07 mmol) of lithium hydroxide in 3 ml water is added and the whole is stirred at 70° C. for some minutes till solution and then 4.5 hr at room temperature. The solvents are evaporated and the residue suspended in ethyl ether and filtered. The solid is then partitioned between dichloromethane and a diluted solution of citric acid. The organic layer is washed with water, dried and concentrated. The residue is chromatographied through SiO2 eluting with dichloromethane/methanol/aq.ammonia 40/8/1. Yield: 0.18 g (31%). $[\alpha]_D = -198.9°$.

Example 46

Preparation of (+) 3-[7-(6,7-Difluoro-quinolin-2-ylmethoxy)-11-methyl-10,11-dihydro-5H-benzo[e]pyrido[2,3-b]azepin-5-ylsulfanyl]-propionic Acid

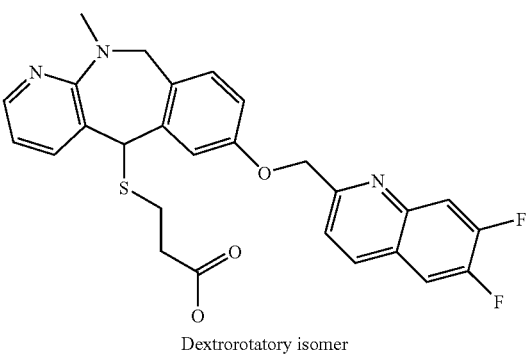

Dextrorotatory isomer

This compound is prepared in a parallel way to that described for the synthesis of the previous one, but starting with the first diastereomer of step 2. $[\alpha]_D = +195.7°$.

Composition Examples

Composition Example 1

Preparation of Tablets

Formulation:

| | |
|---|---|
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the present invention are mixed with 340.8 g of lactose and 85.2 g of microcrystalline cellulose. The mixture is subjected to compression moulding using a roller compactor to give a flake-like-compressed material. The flake-like compressed material is pulverised using a hammer mill, and the pulverised material is screened through a 20 mesh screen. A 4.5 g portion of light silicic anhydride and 4.5 g of magnesium stearate are added to the screened material and mixed. The mixed product is subjected to a tablet making machine equipped with a die/punch system of 7.5 mm in diameter, thereby obtaining 3,000 tablets each having 150 mg in weight.

Composition Example 2

Preparation of Coated Tablets

Formulation:

| | |
|---|---|
| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |
| Hydroxypropylcellulose | 2.3 mg |
| Polyethylene glycol 6000 | 0.4 mg |
| Titanium dioxide | 1.1 mg |
| Purified talc | 0.7 mg |

Using a fluidised bed granulating machine, 15 g of the compound of the present invention are mixed with 285.6 g of lactose and 122.4 g of corn starch. Separately, 22.5 g of polyvinylpyrrolidone is dissolved in 127.5 g of water to prepare a binding solution. Using a fluidised bed granulating machine, the binding solution is sprayed on the above mixture to give granulates. A 4.5 g portion of magnesium stearate is added to the obtained granulates and mixed. The obtained mixture is subjected to a tablet making machine equipped with a die/punch biconcave system of 6.5 mm in diameter, thereby obtaining 3,000 tablets, each having 150 mg in weight.

Separately, a coating solution is prepared by suspending 6.9 g of hydroxypropylmethyl-cellulose 2910, 1.2 g of polyethylene glycol 6000, 3.3 g of titanium dioxide and 2.1 g of purified talc in 72.6 g of water. Using a High Coated, the 3,000 tablets prepared above are coated with the coating solution to give film-coated tablets, each having 154.5 mg in weight.

Composition Example 3

Preparation of Capsules

Formulation:

| | |
|---|---|
| Compound of the present invention | 5.0 mg |
| Lactose monohydrate | 200 mg |
| Colloidal silicon dioxide | 2 mg |
| Corn starch | 20 mg |
| Magnesium stearate | 4 mg |

25 g of active compound, 1 Kg of lactose monohydrate, 10 g of colloidal silicon dioxide, 100 g of corn starch and 20 g of magnesium stearate are mixed. The mixture is sieved through a 60 mesh sieve, and then filled into 5,000 gelatin capsules.

Composition Example 4

Preparation of a Cream

Formulation:

| | |
|---|---|
| Compound of the present invention | 1% |
| Cetyl alcohol | 3% |
| Stearyl alcohol | 4% |
| Glyceryl monostearate | 4% |
| Sorbitan monostearate | 0.8% |
| Sorbitan monostearate POE | 0.8% |
| Liquid vaseline | 5% |
| Methylparaben | 0.18% |
| Propylparaben | 0.02% |
| Glycerine | 15% |
| Purified water csp. | 100% |

An oil-in-water emulsion cream is prepared with the ingredients listed above, using conventional methods.

The invention claimed is:
1. A compound of formula (I):

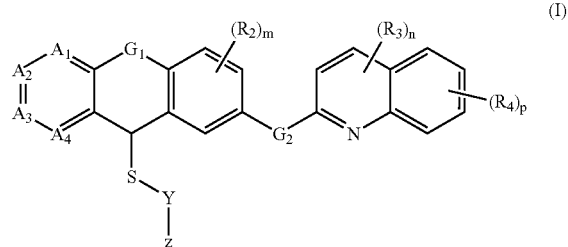

or pharmaceutically acceptable salts thereof, in any stereoisomeric form, or a mixture of any such compounds in any ratio, wherein:

from one to two of $A_1, A_2, A_3$ and $A_4$ are nitrogen atoms, the others being —CH— groups;

$G_1$ represents a group chosen from —$CH_2$—O—, —$CH_2$—$CH_2$—, —CH=CH—, and —N(C1-C4 alkyl)-CH2;

G₂ represents a group chosen from —O—CH₂—, —CH═CH—, and —CH₂—CH₂—;

n, m and p are independently 0, 1 or 2;

R₃ is hydrogen; R₂ and R₄ are chosen from halogen and C1-C4-alkyl;

Y represents an optionally substituted group chosen from alkyl, cycloalkyl, aryl, alkyl-cycloalkyl, cycloalkyl-alkyl, arylalkyl, alkylaryl, alkyl-cycloalkyl-alkyl, cycloalkyl-alkyl-cycloalkyl, alkyl-aryl-alkyl and aryl-alkyl-aryl;

Z represents a group chosen from a tetrazolyl group, a —COOR₅ group, a —CONR₅R₅ group, a NHSO₂R₅ group and a —CONHSO₂R₅ group wherein R₅ is chosen from a hydrogen and an optionally substituted alkyl, aryl, cycloalkyl, heterocyclyl or heteroaryl.

2. A compound according to claim 1 wherein one of A₁, A₂, A₃ and A₄ is a nitrogen atom, the others being —CH— groups.

3. A compound according to claim 2 wherein A₁ is a nitrogen atom and A₂, A₃ and A₄ are —CH— groups.

4. A compound according to claim 2 wherein A₄ is a nitrogen atom and A₁, A₂ and A₃ are —CH— groups.

5. A compound according to claim 1 wherein G₁ is a —CH₂O— group.

6. A compound according to claim 1 wherein G₂ is chosen from —OCH₂— and —CH═CH—.

7. A compound according to claim 1 wherein p is 2 and each R₄ is a halogen atom.

8. A compound according to claim 7 wherein each R₄ is independently chosen from F and Cl.

9. A compound according to claim 1 wherein Y represents a group chosen from alkyl, alkyl-cycloalkyl-alkyl and alkylaryl said group being optionally substituted by one or more substituents chosen from halogens, hydroxy, alkoxy, amino, alkyl groups and haloalkyl.

10. A compound according to claim 9 wherein Y represents a group chosen —CH₂CH₂— and 2-cyclopropylpropyl.

11. A compound according to claim 1 chosen from:

3-{(7-[(6,7-difluoroquinolin-2-yl)methoxy]-5,11-dihydro[1]benzoxepino[3,4-b]pyrindin-5-yl)thio}propanoic acid, {(7-[(6,7-difluoroquinolin-2-yl)methoxy]-5,11-dihydro[1]benzoxepino[3,4-b]pyrindin-5-yl)thio}acetic acid, {(7-[(7-chloro,6-fluoroquinolin-2-yl)methoxy]-5,11-dihydro[1]benzoxepino[3,4-b]pyrindin-5-yl)thio}acetic acid, 3-{(7-[(7-chloro,6-fluoroquinolin-2-yl)methoxy]-5,11-dihydro[1]benzoxepino[3,4-b]pyrindin-5-yl)thio}propanoic acid,

[{(7-[(6,7-difluoroquinolin-2-yl)methoxy]-5,11-dihydro[1]benzoxepino[3,4-b]pyrindin-5-yl)thio}methyl]benzoic acid,

[{(7-[(7-chloro,6-fluoroquinolin-2-yl)methoxy]-5,11-dihydro[1]benzoxepino[3,4-b]pyrindin-5-yl)thio}methyl]benzoic acid, 1-{[(7-[(6,7-difluoroquinolin-2-yl)methoxy]-5,11-dihydro[1]benzoxepino[3,4-b]pyrindin-5-yl)thio]methyl}cyclopropyl acetic acid, 3-{(7-[(6,7-difluoroquinolin-2-yl)methoxy]-5,11-dihydro[1]benzoxepino[3,4-b]pyrindin-5-yl)thio}-2,2-dimethylpropanoic acid, 3-{(7-[(6,7-difluoroquinolin-2-yl)methoxy]-5,11-dihydro[1]benzoxepino[3,4-b]pyrindin-5-yl)thio}-3-methylbutanoic acid, 3-{(7-[(E)-2-(6,7-difluoroquinolin-2-yl)vinyl]-5,11-dihydro[1]benzoxepino[3,4-b]pyrindin-5-yl)thio}propanoic acid, 1-{[(7-[(E)-2-(6,7-difluoroquinolin-2-yl)vinyl]-5,11-dihydro[1]benzoxepino[3,4-b]pyrindin-5-yl)thio]methyl}cyclopropyl acetic acid, {(7-[(E)-2-(6,7-difluoroquinolin-2-yl)vinyl]-5,11-dihydro[1]benzoxepino[3,4-b]pyrindin-5-yl)thio}acetic acid, 7-[(E)-2-(6,7-difluoroquinolin-2-yl)vinyl]-5-{[2-(1H-tetrazol-5-yl)ethyl]thio}-5,11-dihydro[1]benzoxepino[3,4-b]pyridine, 1,1,1-trifluoro-N-[2-({7-[(E)-2-(6,7-difluoroquinolin-2-yl)vinyl]-5,11-dihydro[1]benzoxepino[3,4-b]pyrindin-5-yl)thio)ethyl]methanesulfonamide, 1,1,1-trifluoro-N-[2-({7-[(6,7-difluoroquinolin-2-yl)methoxy]-5,11-dihydro[1]benzoxepino[3,4-b]pyrindin-5-yl)thio)ethyl]methanesulfonamide, 3-{(9-[(E)-2-(6,7-difluoroquinolin-2-yl)vinyl]-5,11-dihydro[1]benzoxepino[4,3-b]pyrindin-11-yl)thio}propanoic acid, 3-{(9-[(6,7-difluoroquinolin-2-yl)methoxy]-5,11-dihydro[1]benzoxepino[4,3-b]pyrindin-11-yl)thio}propanoic acid, 1-{[(9-[(6,7-difluoroquinolin-2-yl)methoxy]-5,11-dihydro[1]benzoxepino[4,3-b]pyrindin-11-yl)thio]methyl}cyclopropyl acetic acid, 7-[(6,7-difluoroquinolin-2-yl)methoxy]-5-{[2-(1H-tetrazol-5-yl)methyl]thio}-5,11-dihydro[1]benzoxepino[3,4-b]pyridine, 7-[(6,7-difluoroquinolin-2-yl)methoxy]-5-{[2-(1H-tetrazol-5-yl)ethyl]thio}-5,11-dihydro[1]benzoxepino[3,4-b]pyridine, 3-[7-(6,7-Difluoro-quinolin-2-ylmethoxy)-11-methyl-10,11-dihydro-5H-benzo[e]pyrido[2,3-b]azepin-5-ylsulfanyl]-propionic acid, 3-[7-(7-Chloro-6-fluoro-quinolin-2-ylmethoxy)-11-methyl-10,11-dihydro-5H-benzo[e]pyrido[2,3-b]azepin-5-ylsulfanyl]-propionic acid, 3-[9-chloro-7-(6,7-difluoro-quinolin-2-ylmethoxy)-5,11-dihydro[1]benzoxepino[3,4-b]pyridin-5-yl)thio]propanoic acid, ethyl 3-[7-(6,7-difluoro-quinolin-2-ylmethoxy)-5,11-dihydro[1]benzoxepino[3,4-b]pyridin-5-yl)thio]propanoate, 3-[7-(6,7-difluoro-quinolin-2-ylmethoxy)-5,11-dihydro[1]benzoxepino[3,4-b]pyridin-5-yl)thio]propanamide, 3-[7-(6,7-difluoro-quinolin-2-ylmethoxy)-9-fluoro-5,11-dihydro[1]benzoxepino[3,4-b]pyridin-5-yl)thio]propanoic acid, 3-[7-(6,7-difluoro-quinolin-2-ylmethoxy)-9-methyl-5,11-dihydro[1]benzoxepino[3,4-b]pyridin-5-yl)thio]propanoic acid, 3-{(7-[(E)-2-(6,7-difluoroquinolin-2-yl)vinyl]-5,11-dihydro[1]benzoxepino[3,4-b]pyrindin-5-yl)thio}propanamide, and ethyl 3-{(7-[(E)-2-(6,7-difluoroquinolin-2-yl)vinyl]-5,11-dihydro[1]benzoxepino[3,4-b]pyrindin-5-yl)thio}propanoate.

12. A process for the preparation of a compound of formula (I):

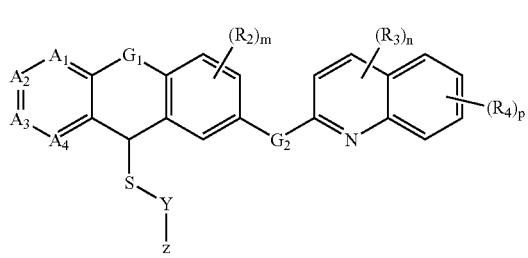

wherein $A_1$, $A_2$, $A_3$, $A_4$, $G_1$, $G_2$, $R_2$, $R_3$, $R_4$ Y and Z are as defined in claim 1, which comprises reacting an alcohol of formula (III):

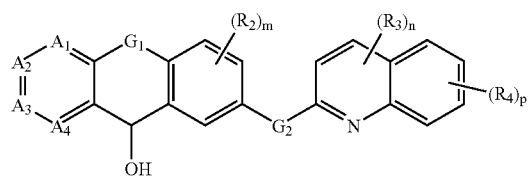

with a mercaptane of formula HS—Y—Z.

13. A compound of formula (III):

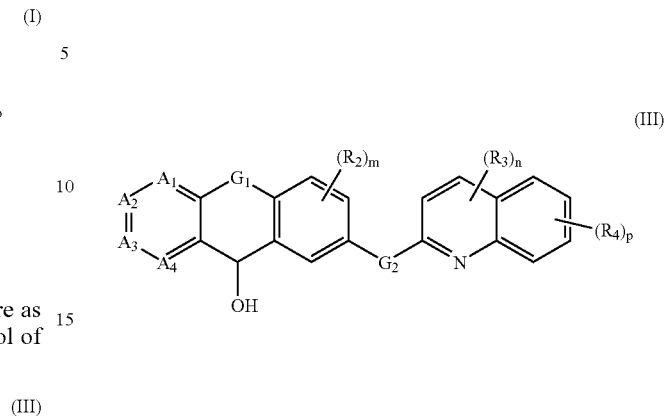

wherein $A_1$, $A_2$, $A_3$, $A_4$, $G_1$, $G_2$, $R_2$, $R_3$, $R_4$ Y and Z are as defined in claim 1.

14. A pharmaceutical composition comprising a compound according to claim 1 and at least one pharmaceutically acceptable diluent or carrier.

* * * * *

UNITED STATES PATENT AND TRADEMARK OFFICE
CERTIFICATE OF CORRECTION

PATENT NO. : 7,557,212 B2
APPLICATION NO. : 10/534487
DATED : July 7, 2009
INVENTOR(S) : Carlos Puig Duran et al.

It is certified that error appears in the above-identified patent and that said Letters Patent is hereby corrected as shown below:

In claim 9, column 93, lines 33-34, "alkylaryl said" should read --alkylaryl, said--.

In claim 10, column 93, line 38, "chosen -$CH_2CH_2$-" should read --chosen from -$CH_2CH_2$- --.

In claim 12, column 95, line 15, "$R_4$ Y" should read --$R_4$, Y--.

In claim 13, column 96, line 21, "$R_4$ Y" should read --$R_4$, Y--.

Signed and Sealed this

Twenty-second Day of September, 2009

David J. Kappos
*Director of the United States Patent and Trademark Office*

UNITED STATES PATENT AND TRADEMARK OFFICE
CERTIFICATE OF CORRECTION

PATENT NO. : 7,557,212 B2
APPLICATION NO. : 10/534487
DATED : July 7, 2009
INVENTOR(S) : Duran et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by (5) days Delete the phrase "by 5 days" and insert -- by 186 days --

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

PATENT NO.       : 7,557,212 B2                                            Page 1 of 1
APPLICATION NO.  : 10/534487
DATED            : July 7, 2009
INVENTOR(S)      : Duran et al.

It is certified that error appears in the above-identified patent and that said Letters Patent is hereby corrected as shown below:

On the Title page,

Item [*] Notice:       Subject to any disclaimer, the term of this patent is extended or adjusted under 35 USC 154(b) by (186) days Delete the phrase "by 186 days" and insert -- by 264 days --

Signed and Sealed this

Eighteenth Day of May, 2010

David J. Kappos
*Director of the United States Patent and Trademark Office*